(12) United States Patent
Tanabe et al.

(10) Patent No.: US 6,281,205 B1
(45) Date of Patent: Aug. 28, 2001

(54) ANTI-ESTROGENIC STEROIDS, AND ASSOCIATED PHARMACEUTICAL COMPOSITIONS AND METHODS OF USE

(75) Inventors: Masato Tanabe, Palo Alto; Richard H. Peters, San Jose; Wan-Ru Chao; Ling Jong, both of Sunnyvale, all of CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 09/220,408

(22) Filed: Dec. 24, 1998

Related U.S. Application Data

(63) Continuation-in-part of application No. 08/998,877, filed on Dec. 24, 1997, now Pat. No. 6,054,446.

(51) Int. Cl.$^7$ .......................... A61K 31/56; A61K 31/58; C07J 5/00; C07J 43/00
(52) U.S. Cl. .......................... 514/176; 514/182; 540/112; 552/558
(58) Field of Search ........................ 552/558; 540/112; 514/176, 182

(56) References Cited

U.S. PATENT DOCUMENTS

| | | |
|---|---|---|
| 2,666,769 | 1/1954 | Colton . |
| 2,840,581 | 6/1958 | Hogg et al. . |
| 3,271,428 | 9/1966 | Villani . |
| 3,291,690 | * 12/1966 | Bertin et al. .......................... 167/65 |
| 3,318,917 | 5/1967 | Benn . |
| 3,318,925 | 5/1967 | Anner et al. . |
| 3,405,147 | 10/1968 | Counsell et al. . |
| 3,431,258 | 3/1969 | Lefebvre et al. . |
| 3,448,126 | 6/1969 | Benn . |
| 3,536,703 | 10/1970 | Colton et al. . |
| 3,716,530 | 2/1973 | Krubiner et al. . |
| 3,859,365 | 1/1975 | Young . |
| 5,274,089 | * 12/1993 | Bundy et al. ........................ 540/112 |
| 5,371,078 | 12/1994 | Clark et al. . |
| 5,554,603 | 9/1996 | Kim et al. . |
| 5,621,123 | * 4/1997 | Johnson et al. ...................... 552/522 |
| 5,679,668 | * 10/1997 | Bonfils et al. ........................ 514/182 |
| 5,679,688 | 10/1997 | Bonfils et al. . |
| 5,866,560 | 2/1999 | Bohlmann et al. . |

FOREIGN PATENT DOCUMENTS

| | | |
|---|---|---|
| 661288 | 3/1965 | (BE) . |
| 3012M | 12/1964 | (FR) . |
| WO8700175 | 1/1987 | (WO) . |
| WO9807740 | 2/1998 | (WO) . |

OTHER PUBLICATIONS

Blickenstaff et al. (1985), "Synthesis of Some Analogs of Estradiol," *Steroids* 46(4,5):889–902.
Nique et al. (1995), "RU 58668, Antineoplastic Pure Antiestrogen," *Drugs of the Future* 20(4):362–366.
Peters et al. (1988), "17–Desoxy Estrogen Analogues," *J. Med. Chem.* 32:1642–1652.
Qian et al. (1988), "Synthesis and Biological Activity of 17β–Substituted Estradiol," *J. Steroid. Biochem.* 29:657–664.
Van de Velde et al. (1994), "RU 58668: Profil Des Activités Pharmacologiques D'un Nouvel Antiestrogéne Pur Susceptible De Traiter Certains Échappements Au Tamoxiféne," *Pathol. Biol.* 42:30.
Van de Velde et al. (1995), "Exploration of the Therapeutic Potential of the Antiestrogen RU 58668 in Breast Cancer Treatment," *Ann. N.Y. Acad. Sci.* 761:164–175.
Wakeling et al. (1988), "Novel Antioestrogens Without Partial Agonist Activity," *J. Steroid Biochem* 31(4B):645–653.
Wakeling (1990), "Therapeutic Potential of Pure Antioestrogens in the Treatment of Breast Cancer," *J. Steroid Biochem. Molec. Biol.* 37(6):771–775.
Wakeling et al. (1991), "A Potent Specific Pure Antiestrogen with Clinical Potential," *Cancer Res.* 51:3867–3873.
Miyairi et al. (1991), "Structure of the Adduct of 16α–Hydroxyestrone with a Primary Amine: Evidence for the Heyns Rearrangement of Steroidal D–Ring α–Hydroxyimines," *Steroids* 56:361–366.
Peters et al. (1989), "11β–Nitrate Estrane Analogues: Potent Estrogens," *J. Med. Chem.* 32:2306–2310.
Rao et al. (1994), "Preparative Chemical Methods for Aromatization of 19–Nor–$\Delta^4$–3–Oxosteroids," *Steroids* 59:621–627.
Rubio–Póo et al. (1997), "Efects of 17β–(N,N–Diethylaminoethyl)Amino–1,3,5(10)–Estratrien–3–OL, and Its Androstane Analog on Blood Clotting Time," *Med. Chem. Res.* 7(2):67–75.
Yuan (1982), "Synthesis of 3,4–$^{13}C_2$ Steroids," *Steroids* 39(3):279–289.
Poirier et al. (1996), "D–Ring Alkylamide Derivatives of Estradiol: Effect on ER–Binding Affinity and Antiestrogenic Activity," *Bioorganic & Medicinal Chemistry Letters* 6(21):2537–2542.

\* cited by examiner

*Primary Examiner*—Barbara P. Badio
(74) *Attorney, Agent, or Firm*—Dianne E. Reed; Reed & Associates

(57) ABSTRACT

Novel anti-estrogenic compounds are provided which are useful to treat a variety of disorders, particularly estrogen-dependent disorders. Preferred compounds have a 1,3,5(10)-estratriene nucleus, and are substituted at the C-17 or C-11 position with a molecular moiety which renders the compounds effective to competitively block the binding of estrogen to its receptor. Particularly preferred compounds are 17-desoxy-1,3,5(10)-estratrienes. Therapeutic methods and pharmaceutical compositions are provided as well.

16 Claims, 3 Drawing Sheets

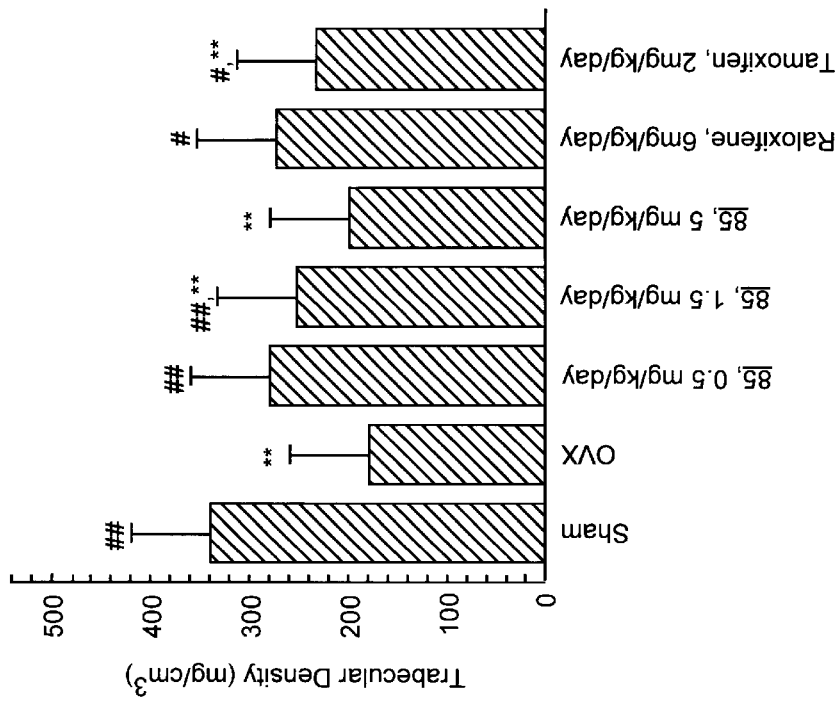
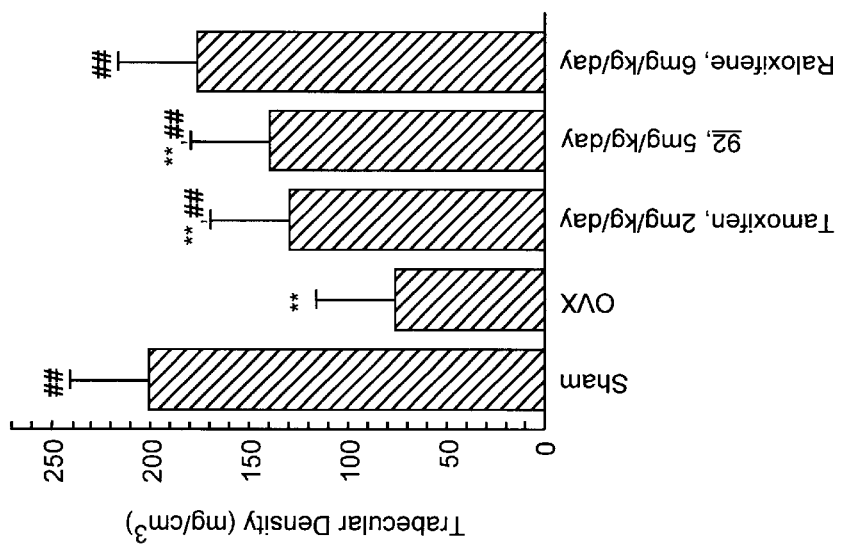
FIG. 1 – Effect of Compounds 85 and 92 on trabecular density in ovariectomized rats after treatment for 26 days.
,##) $P<0.05$, 0.01 (vs OVX)   *,**) $P<P<0.05$, 0.01 (vs Sham)

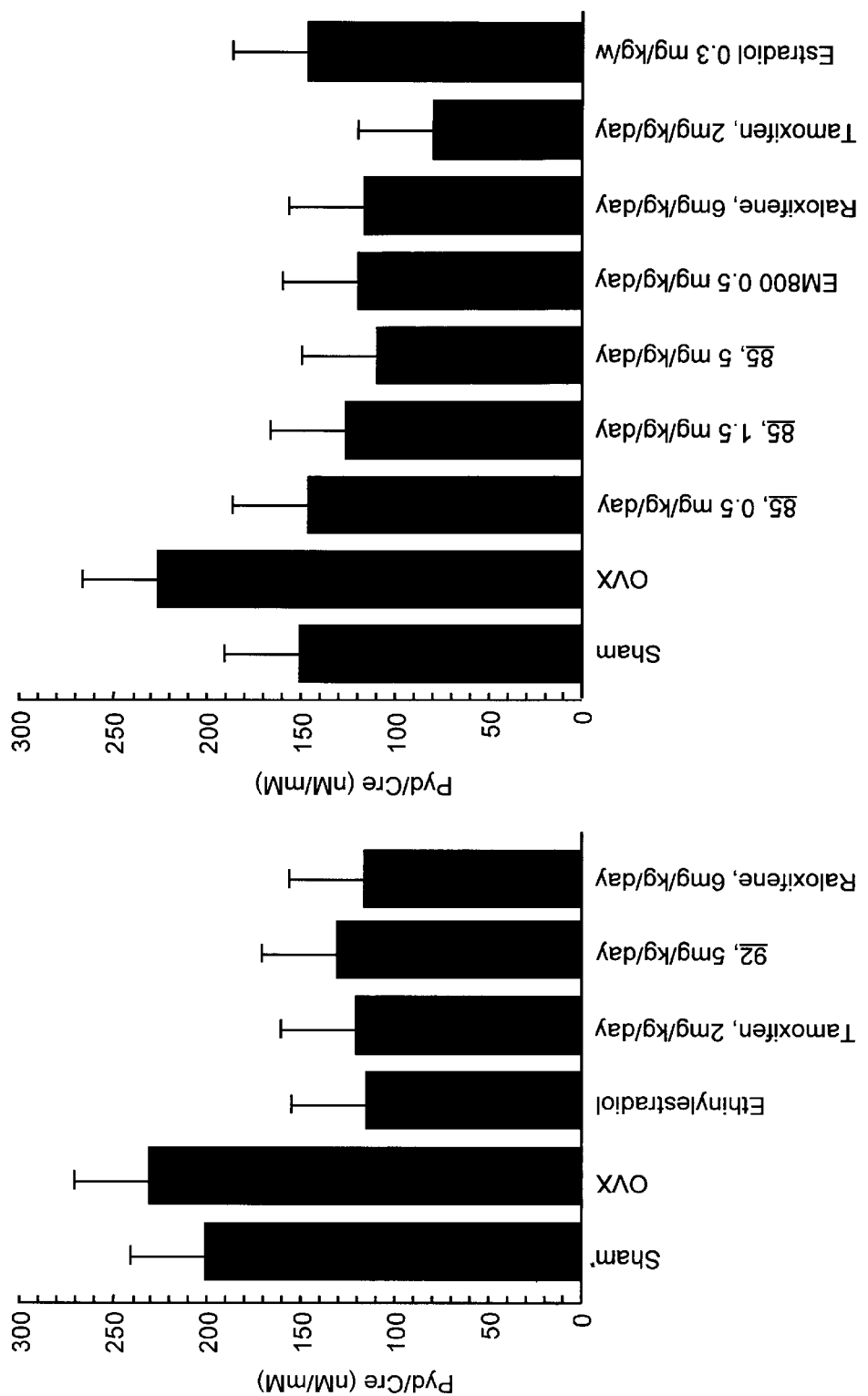
FIG. 2 – Effect of Compounds 85 and 92 on urine levels of pyridinoline and deoxypyridinoline in ovariectomized rats after treatment for 28 days.

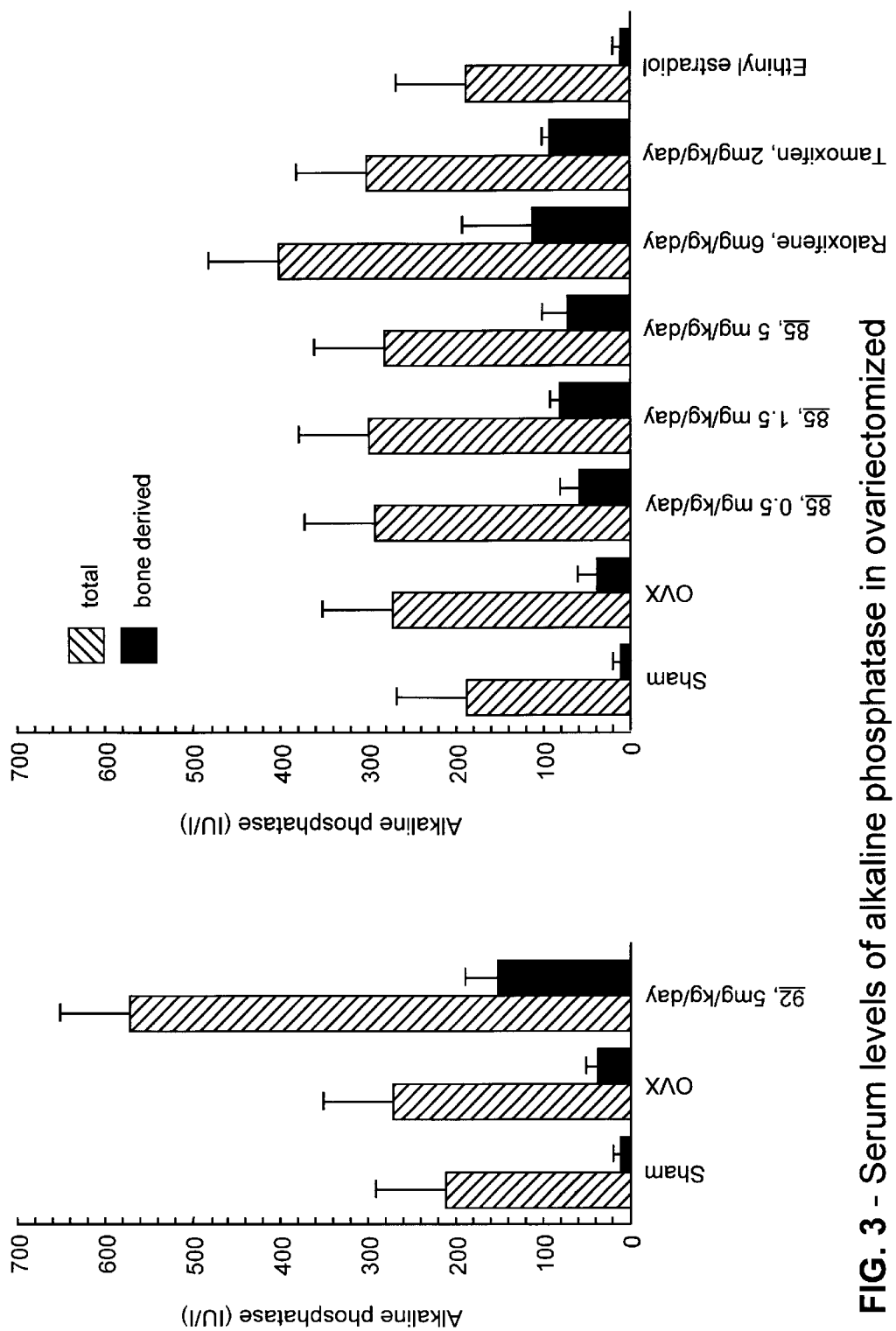
FIG. 3 – Serum levels of alkaline phosphatase in ovariectomized rats treated with Compounds 85 and 92.

ANTI-ESTROGENIC STEROIDS, AND ASSOCIATED PHARMACEUTICAL COMPOSITIONS AND METHODS OF USE

CROSS-REFERENCE TO RELATED APPLICATIONS

This is a continuation-in-part of U.S. patent application Ser. No. 08/998,877, filed Dec. 24, 1997, issued Apr. 25, 2000 as U.S. Pat. No. 6,054,446, the disclosure of which is incorporated by reference herein.

TECHNICAL FIELD

The present invention relates generally to steroid hormones, and more specifically relates to novel steroids which are useful as anti-estrogenic agents. The invention additionally relates to methods for treating various disorders using the novel compounds, particularly conditions or diseases that are estrogen-dependent, i.e., are estrogen-induced or estrogen-stimulated, and to pharmaceutical compositions containing one or more of the novel compounds.

BACKGROUND

Breast cancer is one of the most prevalent types of cancer, and epidemiological and clinical studies have shown that approximately one-third of breast tumors are estrogen-dependent. This means that estrogens are required for the growth of such breast tumors in both premenopausal and postmenopausal patients. In postmenopausal women, in whom breast cancer most commonly occurs, breast tumor concentrations of estrone and estradiol are considerably higher than blood estrogen levels. Although retention of estrogens in breast tumors by high-affinity binding proteins contributes to the level of estrogens in tumors, estrogen concentrations in the breast are higher than plasma levels in breast cancer patients regardless of whether their tumors are estrogen receptor-positive (ER+) or receptor-negative (ER-). In situ formation of estrogen from estrogen biosynthetic precursors within tumors is now known to make a major contribution to the estrogen content of breast tumors.

Numerous other estrogen-dependent conditions, disorders and diseases have been identified as well, including, but not limited to, ovarian, uterine and pancreatic cancers, galactorrhea, McCune-Albright syndrome, benign breast disease, and endometriosis.

Estrogenic effects are mediated by specific receptors located in the nucleus of estrogen-responsive cells. The receptor contains a hormone binding domain for binding estrogen, transcription activating domains, and a DNA binding domain. The binding of the receptor-hormone complex to estrogen response elements (ERE's) in the DNA of target genes is necessary for regulating gene transcription.

Drugs that competitively block estrogen binding to its receptor, termed anti-estrogens, are capable of inhibiting the stimulatory effects of the hormone on cell proliferation and are therefore useful in the clinical treatment of breast cancer. Clinically, estrogen receptor-positive tumors respond with a higher frequency to anti-estrogens than do tumors lacking a significant level of receptors.

Anti-estrogenic drugs fall into two chemical classes: nonsteroidal and steroidal. The nonsteroidal anti-estrogen tamoxifen (Nolvadex®) has been used as an adjunctive treatment for breast cancer following chemotherapy or radiation therapy. However, tamoxifen itself exhibits estrogenic activity in reproductive tissue, resulting in an increased risk of endometrial cancer and possible recurrence of breast cancer after long-term therapy. Furthermore, tamoxifen behaves only as a partial agonist in the uterus.

To date, little work has been done in the development of selective competitive antagonists of estrogen. Several steroidal anti-estrogens have been synthesized which lack estrogenic activity. Included among these are ICI 164,384, ICI 182,780 and RU 58668. See, e.g.: Wakeling et al. *J Steroid Biochem.* 31:645–653 (1988), which pertains to ICI 164,384; Wakeling et al., *Cancer Res.* 51:3867–3873 (1991), and Wakeling et al., *J. Steroid Biochem. Molec. Biol.* 37:771–774 (1990), which pertain to ICI 182,780; and Van de Velde et al., Ann. N.Y. Acad. Sci. 761:164–175 (1995), Van de Velde et al., *Pathol. Biol* 42:30 (1994), and Nique et al., *Drugs Future* 20:362–366 (1995), which relate to RU 58668. Unfortunately, these drugs are not orally active and must be administered in high doses intramuscularly. Furthermore, the manufacture of these drugs is laborious, requiring a complicated, 14–16 step synthesis with very low overall yields. Potent steroidal anti-estrogens that are orally active have not yet been developed or commercialized, although the nonsteroidal mixed agonist/antagonist "raloxifene" is currently available.

Accordingly, the present invention is directed to novel steroidal agents that are extremely effective anti-estrogenic agents, i.e., are potent antagonists of estrogen in breast and/or uterine tissue. The invention thus represents a significant advance in the art, particularly in the treatment of breast cancer and other diseases and conditions that are potentiated by the presence of estrogens.

Significantly, a number of the compounds of the invention that are potent, orally active agents, display tissue-selective pharmacology. That is, the compounds are useful as tissue-selective estrogen agonists/antagonists, also termed "Selective Estrogen Receptor Modulators" or "SERMs." SERMs produce beneficial estrogen-like effects in some respects, notably on bone and lipid metabolism, while nevertheless acting as estrogen antagonists in the breast and/or uterus. The SERM profile may be distinguished from that of a pure estrogen such as 17β-estradiol, which behaves as an estrogen agonist in all tissues, and from that of a pure anti-estrogen, which exhibits an estrogen antagonist profile in all tissue types.

The following references pertain to one or more aspects of the invention and as such may be of background interest to those skilled in the art: U.S. Pat. No. 2,840,581 to Hogg et al., which describes estradiol derivatives substituted at the 17-position with =CH—$CH_2OH$ and having estradiol-like activity; U.S. Pat. No. 3,536,703 to Colton et al., which describes antimicrobial estradiol derivatives substituted at C-3 with methoxy, and at C-17 with various groups, including =C—$CH_2$-$NR_3^+$ (wherein R is hydrogen or lower alkyl or wherein two R groups form a cyclic structure); U.S. Pat. No. 3,716,530 to Krubiner et al., which describes steroids containing various substituents at the C-17 position, including an estradiol derivative substituted at C-17 with =CH—$CH_2X$, wherein X is halogen (stated to be useful as an intermediate in the synthesis of progestational compounds and antifungal agents); Blickenstaff et al., *Steroids* 46 (4,5): 889–902 (1985), which relates to estradiol derivatives having substituents at the 16-position bound to the steroid nucleus through a double bond, synthesized as part of a search for novel anti-cancer agents; French Patent No. 1,453,210, which shows estradiol analogs substituted at the 17β-position with —CH($CH_3$)—O—($CH_2$)$_2$NR'R", wherein R' and R" may be alkyl or aralkyl; French Special Patent for Medications No. M3031, which relates to the synthesis of 3-hydroxy-20α-dimethylaminoethoxy-19-norpregna-1,3,5

(10)-triene; and Qian et al., *J. Steroid Biochem.* 29(6): 657–664 (1988), which evaluates the correlation between substitution at the 17-position of estradiol and possible anti-estrogenic activity, and describes estradiol analogs substituted at the 17β-position with —O—$(CH_2)_2$—$NR_1R_2$, wherein $R_1$ and $R_2$ are methyl, ethyl, cyclopentyl, cyclohexyl, or tetrahydropyranyl (none of the compounds were found to have anti-estrogenic activity).

In addition, the following references discuss tissue-selective anti-estrogens, or SERMs, and as such may be of interest with respect to the present invention as well: Grese et al. (1998), "Synthesis and Pharmacology of Conformationally Restricted Raloxifene Analogues: Highly Potent Selective Estrogen Receptor Modulators," *J. Med. Chem.* 41:1272–1283; Bryant et al. (1998), "Selective Estrogen Receptor Modulators: An Alternative to Hormone Replacement Therapy," *J. Soc. for Exper. Biol. and Medicine*, pp. 45–52; Ke et al. (1998), "Effects of CP-336,156, a New, Nonsteroidal Estrogen Agonist/Antagonist, on Bone, Serum Cholesterol, Uterus and Body Composition in Rat Models," *Endocrinology* 139(4):2068–2076; and Kauffman et al. (1997), "Hypocholesterolemic Activity of Raloxifene (LY139481): Pharmacological Characterization as a Selective Estrogen Receptor Modulator," *J. Pharmacol. Experimental Therap.* 280(1):146–153. Reference may also be had to U.S. Pat. No. 5,447,941 to Zuckerman, U.S. Pat. No. 5,510,370 to Hock, U.S. Pat. No. 5,552,416 to Keohane, U.S. Pat. No. 5,578,613 to Bryant et al., U.S. Pat. No 5,578,614 to Bryant et al., U.S. Pat. No. 5,593,987 to Cullinan et al., U.S. Pat. No. 5,610,167 to Cullinan, U.S. Pat. No. 5,641,790 to Draper, U.S. Pat. No. 5,646,137 to Black et al., U.S. Pat. No. 5,663,184 to Bryant et al., and U.S. Pat. No 5,719,165 to Dodge, each of which pertains to different uses of tissue-selective anti-estrogens, particularly raloxifene.

No art of which applicants are aware, however, describes compounds as provided herein. To the best of applicants' knowledge, the compounds and methods of the invention are previously unknown and completely unsuggested by the art.

SUMMARY OF THE INVENTION

Accordingly, it is a primary object of the invention to address the above-mentioned need in the art by providing novel steroid compounds useful as anti-estrogenic agents.

It is another object of the invention to provide novel compounds that are anti-estrogenic and have reduced estrogenic activity as may be determined by the degree of inhibition and degree of stimulation, respectively, of estradiol-induced alkaline phosphatase activity in human Ishikawa cells.

It is an additional object of the invention to provide such compounds which have substantially no estrogenic activity as may be determined by the aforementioned test.

It is still another object of the invention to provide such compounds in the form of steroidal active agents having a 1,3,5-estratriene nucleus that are preferably "17-desoxy."

It is yet another object of the invention to provide a method for treating an individual with a disorder that is estrogen-dependent, i.e., an estrogen-induced or estrogen-stimulated condition or disease, by administering to the individual a therapeutically effective amount of an anti-estrogenic compound as provided herein, or a pharmaceutically acceptable salt thereof.

It is a further object of the invention to provide a pharmaceutical composition for treating an individual with a disorder that is estrogen-dependent, the composition comprising a therapeutically effective amount of a novel compound as provided herein or a pharmaceutically acceptable salt or ester thereof.

Additional objects, advantages and novel features of the invention will be set forth in part in the description which follows, and in part will become apparent to those skilled in the art upon examination of the following, or may be learned by practice of the invention.

In one embodiment, then, the invention relates to novel compounds having anti-estrogenic activity and reduced estrogenic activity as determined by the degree of inhibition and degree of stimulation, respectively, of estradiol-induced alkaline phosphatase activity in human Ishikawa cells. Preferred compounds of the invention have a 1,3,5-estratriene nucleus, and are substituted at either the C-17 position or the C-11 position with a molecular moiety which renders the compounds effective to competitively block the binding of estrogen to its receptor. Of these, the more preferred compounds are "17-desoxy," i.e., there is no oxygen atom bound directly to the C-17 position. Such compounds are encompassed, for example, by the generic structures of Formula (I) and (III) herein.

The preferred anti-estrogenic compounds of the invention are exemplified by Formula (I), Formula (II) and Formula (III), as follows:

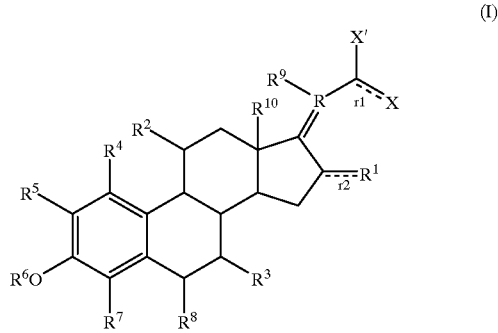

In Formula (I),
R is selected from the group consisting of C and N, and, when R is C, is in either the E or Z configuration;
r1 and r2 are optional double bonds;
X is hydrocarbyl, generally including at least one oxygen atom, sulfur atom, and/or nitrogen atom in the form of an —O—, —S—, —NH— or —N(alkyl)-linkage, and optionally containing additional substituents and functional groups such as hydroxyl, oxo, alkoxy, amino, alkyl-substituted amino, halogeno, aryl, heteroaryl, heterocycloalkyl, or the like;
X' is hydrogen or hydrocarbyl, generally including at least one oxygen atom, sulfur atom, and/or nitrogen atom in the form of an —O—, —S—, —NH— or —N(alkyl)-linkage, and, as for X, optionally including additional substituents and functional groups, or
X and X' may be linked to form a heterocyclic ring, typically a six- to eight-membered heterocycloalkyl ring containing one to four, typically two to three heteroatoms selected from the group consisting of nitrogen, oxygen and sulfur;
when r2 is present, $R^1$ is $CR^{11}R^{12}$ wherein $R^{11}$ and $R^{12}$ are hydrogen or lower alkyl, and when r2 is not present, $R^1$ is hydrogen, alkyl, or halogen;
$R^2$ is selected from the group consisting of hydrogen, hydroxyl, alkyl, alkenyl, aryl, alkaryl, —$ONO_2$, —$OR^{13}$ and —$SR^{13}$ wherein $R^{13}$ is alkyl, acyl or aryl;

$R^3$ is selected from the group consisting of hydrogen, hydroxyl, halogen, alkyl, alkenyl, aryl, alkaryl, cyano, —$OR^{13}$ and —$SR^{13}$ wherein $R^{13}$ is as defined previously;

$R^4$ is hydrogen or lower alkyl;

$R^5$ is selected from the group consisting of hydrogen, lower alkoxy, halogen, cyano, —$CH_2CH=CH_2$, —CHO, —$NR^{14}R^{15}$ and —$(CH_2)NR^{14}R^{15}$ wherein $R^{14}$ and $R^{15}$ may be the same or different and are either hydrogen or alkyl, or together form a five- or six-membered cycloalkyl group optionally containing an additional nitrogen heteroatom;

$R^6$ is selected from the group consisting of hydrogen, alkyl, acyl, —C(O)-aryl, —C(O)-alkyl and —$SO_2NH_2$;

$R^7$ is selected from the group consisting of hydrogen, halogen, —$NO_2$, —CHO, —$CH_2CH=CH_2$, —$NR^{16}R^{17}$ and —$CH_2NR^{16}R^{17}$ wherein $R^{16}$ and $R^{17}$ may the same or different and are hydrogen, alkyl or acetyl;

$R^8$ is selected from the group consisting of hydrogen, hydroxyl, —$OR^{18}$ and —$SR^{18}$ wherein $R^{18}$ is alkyl, acyl or aryl;

$R^9$ is hydrogen or alkyl, with the proviso that when R is N, $R^9$ is not present; and $R^{10}$ is methyl or ethyl.

In another embodiment, the invention relates to novel compounds having the structure of Formula (II)

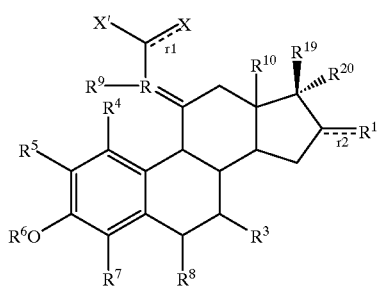

(II)

wherein:

r1, r2, R, $R^1$, $R^3$, $R^4$, $R^5$, $R^6$, $R^7$, $R^8$, $R^9$, $R^{10}$, X and X' as are defined above; and $R^{19}$ and $R^{20}$ are independently selected from the group consisting of hydrogen, hydroxyl, alkyl, alkenyl, alkynyl, alkoxy, and halogen, or $R^{19}$ and $R^{20}$ together form =O.

In a further embodiment, the invention relates to novel compounds having the structure of Formula (III)

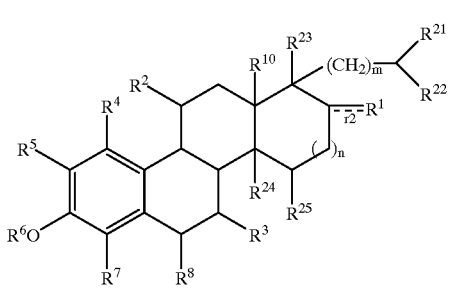

(III)

wherein:

r2, $R^1$ through $R^8$ and $R^{10}$ are as defined above;

m is an integer in the range of 0 to 6 inclusive;

n is 0 or 1;

$R^{21}$ is hydrocarbyl including at least one oxygen atom, sulfur atom, and/or nitrogen atom in the form of an —O—, —S—, —NH— or —N(alkyl)-linkage, and optionally including additional substituents and functional groups such as hydroxyl, oxo, alkoxy, amino, alkyl-substituted amino, halogeno, aryl, heteroaryl, heterocycloalkyl, or the like;

$R^{22}$ is hydrogen or alkyl, or, when m is 0, $R^{21}$ and $R^{22}$ may be linked to form a five- or six-membered cyclic structure which may or may not be aromatic, containing 0 to 3 heteroatoms selected from the group consisting of N, O and S, and substituted with 0 to 4 substituents selected from the group consisting of alkyl, alkenyl, alkynyl, alkoxy, —C(O)-alkyl, —C(O)—O-alkyl, —O—(CO)-alkyl, —C(O)-aryl, hydroxyl, carboxyl, halogen, nitrile, nitrate and fluorinated alkyl;

$R^{23}$ is hydrogen or lower alkyl; and $R^{24}$ and $R^{25}$ are both hydrogen or are both methylene bound to each other through a single covalent bond.

Each of Formula (I), (II) and (III) is intended to encompass pharmaceutically acceptable salts, esters, amides, prodrugs, and other analogs and derivatives of the compounds shown.

In another embodiment, the invention relates to pharmaceutical compositions containing, in combination, a pharmaceutically acceptable carrier and an anti-estrogenic compound of the invention, i.e., an agent that is anti-estrogenic but has reduced estrogenic activity as may be determined by the degree of inhibition and degree of stimulation, respectively, of estradiol-induced alkaline phosphatase activity in human Ishikawa cell. Preferred such compounds are steroids having a 1,3,5-estratriene nucleus that are 17-desoxy, and particularly preferred compounds have the side chain —$(CH_2)_m$—$CHR^{21}R^{22}$ at the 17-position, as shown in structural formula (III), with m, $R^{21}$ and $R^{22}$ as defined above. Typically, the pharmaceutical compositions containing as the active agent a compound defined by structural formula (I), (II) or (III).

In an additional embodiment, the invention relates to methods of using the novel compounds as anti-estrogenic agents. The novel anti-estrogenic compounds find utility in treating individuals with disorders that are estrogen-dependent, i.e., conditions or diseases that are estrogen-induced or estrogen-stimulated. Important examples of such a use include treatment of breast, uterine, ovarian and pancreatic cancers. The compounds my also be used in methods of treating certain conditions and disorders that are not estrogen-dependent, e.g., non-estrogen-dependent cancers, and particularly cancers which are multiple drug-resistant.

In a further embodiment, the invention relates to methods for using the compounds of the invention as tissue-selective anti-estrogenic agents, i.e., as "SERMs," to treat or prevent breast disorders, to increase bone mass and/or inhibit bone loss, to lower serum cholesterol, and the like.

BRIEF DESCRIPTION OF THE FIGURES

FIG. 1 illustrates in graph form the effect of two representative compounds of the invention on trabecular bone density in ovariectomized rats, as evaluated in Example 42 herein.

FIG. 2 illustrates in graph form the effect of two representative compounds of the invention on urine levels of pyridinoline and deoxypyridinoline in ovariectomized rats, as evaluated in Example 42 herein.

FIG. 3 illustrates in graph form the effective of two representative compounds of the invention on serum levels of alkaline phosphatase in ovariectomized rats, as evaluated in Example 42 herein.

DETAILED DESCRIPTION OF THE INVENTION

Definitions and Nomenclature

Before the present compounds, compositions and methods are disclosed and described, it is to be understood that this invention is not limited to specific reagents or reaction conditions, specific pharmaceutical carriers, or to particular administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an anti-estrogenic agent" includes mixtures of anti-estrogenic agents, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of one to six carbon atoms, preferably one to four carbon atoms. The term "cycloalkyl" as used herein refers to a cyclic hydrocarbon of from 3 to 8 carbon atoms, such as cyclopropyl, cyclobutyl, cyclopentyl, cyclohexyl, cycloheptyl and cyclooctyl.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of two to six carbon atoms, preferably two to four carbon atoms. The term "cycloalkenyl" intends a cyclic alkenyl group of three to eight, preferably five or six, carbon atoms.

The term "alkynyl" as used herein refers to a branched or unbranched hydrocarbon group of 2 to 24 carbon atoms containing at least one triple bond, such as ethynyl, n-propynyl, isopropynyl, n-butynyl, isobutynyl, octynyl, decynyl, and the like. Preferred alkynyl groups herein contain 2 to 12 carbon atoms. The term "lower alkynyl" intends an alkynyl group of two to six carbon atoms, preferably two to four carbon atoms.

The term "alkylene" as used herein refers to a difunctional branched or unbranched saturated hydrocarbon group of 1 to 24 carbon atoms, such as methylene, ethylene, n-propylene, n-butylene, n-hexylene, decylene, tetradecylene, hexadecylene, and the like. The term "lower alkylene" refers to an alkylene group of one to six carbon atoms, preferably one to four carbon atoms.

The term "alkenylene" as used herein refers to a difunctional branched or unbranched hydrocarbon group of 2 to 24 carbon atoms containing at least one double bond, such as ethenylene, n-propenylene, n-butenylene, n-hexenylene, and the like. The term "lower alkenylene" refers to an alkylene group of two to six carbon atoms, preferably two to four carbon atoms.

The term "alkoxy" as used herein intends an alkyl group bound through a single, terminal ether linkage; that is, an "alkoxy" group may be defined as —O-alkyl where alkyl is as defined above. A "lower alkoxy" group intends an alkoxy group containing one to six, more preferably one to four, carbon atoms.

The term "acyl" is used in its conventional sense to refer to a substituent alkyl-C–(O)— wherein alkyl is as defined above. The term "lower acyl" refers to an acyl group wherein the alkyl moiety of the group contains one to six, more preferably one to four, carbon atoms.

The term "aryl" as used herein, and unless otherwise specified, refers to an aromatic species containing 1 to 3 aromatic rings, either fused or linked, and either unsubstituted or substituted with 1 or more substituents typically selected from the group consisting of lower alkyl, lower alkoxy, halogen, and the like. Preferred aryl substituents contain 1 aromatic ring or 2 fused or linked aromatic rings. The term "arylene" refers to a difunctional aromatic species containing 1 to 3 aromatic rings substituted with 1 or more substituents as above. Preferred arylene substituents contain 1 aromatic ring (e.g., phenylene) or 2 fused or linked aromatic rings (e.g., biphenylylene).

The term "aralkyl" refers to an aryl group with an alkyl substituent. The term "aralkylene" refers to an arylene group with an alkyl substituent.

The term "alkaryl" refers to an alkyl group that has an aryl substituent. The term "alkarylene" refers to an alkylene group that has an aryl substituent.

The term "heterocyclic" refers to a five- or six-membered monocyclic structure or to an eight- to eleven-membered bicyclic heterocycle. The "heterocyclic" substituents herein may or may not be aromatic, i.e., they may be either heteroaryl or heterocycloalkyl. Each heterocycle consists of carbon atoms and from one to three, typically one or two, heteroatoms selected from the group consisting of nitrogen, oxygen and sulfur, typically nitrogen and/or oxygen.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "hydrocarbyl" is used in its conventional sense to refer to a hydrocarbon group containing carbon and hydrogen, and may be aliphatic, alicyclic or aromatic, or may contain a combination of aliphatic, alicyclic and/or aromatic moieties. Aliphatic and alicyclic hydrocarbyl may be saturated or they may contain one or more unsaturated bonds, typically double bonds. The hydrocarbyl substituents herein generally contain 1 to 24 carbon atoms, more typically 1 to 12 carbon atoms, and may be substituted with various substituents and functional groups, or may be modified so as to contain ether, thioether, —NH—, —NR, —C(O)—, —C(O)—O— and/or other linkages. "Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. Similarly, the phrase an "optionally present" double bond as indicated by a dotted line-----in the chemical formulae herein means that a double bond may or may not be present, and, if absent, a single bond is indicated.

The terms "treating" and "treatment" as used herein refer to reduction in severity and/or frequency of symptoms, elimination of symptoms and/or underlying cause, prevention of the occurrence of symptoms and/or their underlying cause, and improvement or remediaton of damage. Thus, for example, the present method of "treating" an estrogen-dependent disorder, as the term is used herein, encompasses both prevention of the disorder and treatment of the disorder in a clinically symptomatic individual.

By the terms "effective amount" or "pharmaceutically effective amount" or "an effective anti-estrogenic amount" of an agent as provided herein are meant a nontoxic but sufficient amount of the agent to provide the desired prophylactic or therapeutic effect. As will be pointed out below, the exact amount required will vary from subject to subject, depending on the species, age, and general condition of the subject, the severity of the condition being treated, and the particular anti-estrogenic agent and mode of administration, and the like. Thus, it is not possible to specify an exact "effective amount." However, an appropriate "effective" amount in any individual case may be determined by one of ordinary skill in the art using only routine experimentation.

By "pharmaceutically acceptable carrier" is meant a material which is not biologically or otherwise undesirable, i.e., the material may be administered to an individual along with the selected anti-estrogenic agent without causing any undesirable biological effects or interacting in a deleterious manner with any of the other components of the pharmaceutical composition in, which it is contained. Similarly, a "pharmaceutically acceptable" salt or a "pharmaceutically acceptable" ester of a novel compound as provided herein is a salt or ester which is not biologically or otherwise undesirable.

By "anti-estrogenic" as used herein is meant a compound which tends to inhibit the in situ production of estrogens such as estradiol, following administration to a mammalian individual. While not wishing to be bound by theory, the inventors herein believe that the compounds of the invention are anti-estrogenic in nature by virtue of competitively blocking the binding of estrogen to its receptor, particularly in breast and uterine tissue. Anti-estrogenic activity can be evaluated in terms of inhibition of estradiol-induced alkaline phosphatase activity in human Ishikawa cells using for example, the procedures described in Example 40 herein. Typically, the novel anti-estrogenic agents inhibit $10^{-9}$M estradiol-stimulated alkaline phosphatase activity by at least 30%, preferably by at least about 45%, more preferably by at least about 75%, and most preferably by at least about 90%.

By having "substantially no estrogenic activity" as used herein is meant a compound which has less than about 5%, preferably less than about 2%, of the estrogenic activity of estradiol (as may be determined, for example, using the procedures described in Example 40). The term "reduced estrogenic activity" refers to a compound that has 60% or less of the estrogenic activity of estradiol.

The term "tissue selective" as used herein refer to compounds of the invention that act as SERMs, in that they are anti-estrogenic in reproductive tissue, particularly in breast and/or uterine tissue, have reduced or substantially no estrogenic activity in reproductive tissue, but produce beneficial estrogen-like effects in other respects, including, but not limited to, bone and lipid metabolism. That is, such compounds act as estrogen agonists on bone and cholesterol metabolism.

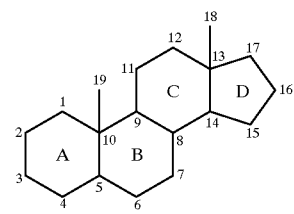

In describing the location of groups and substituents, the above numbering systems will be employed, to conform the numbering of the cyclopentanophenanthrene nucleus to the convention used by the IUPAC or Chemical Abstracts Service. The term "steroid" as used herein is intended to mean compounds having the aforementioned cyclopentanophenanthrene nucleus.

In these structures, the use of bold and dashed lines to denote particular conformation of groups again follows the IUPAC steroid-naming convention. The symbols "α" and "β" indicate the specific stereochemical configuration of a substituent at an asymmetric carbon atom in a chemical structure as drawn. Thus "α," denoted by a broken line, indicates that the group in question is below the general plane of the molecule as drawn, and "β," denoted by a bold line, indicates that the group at the position in question is above the general plane of the molecule as drawn.

In addition, the five- and six-membered rings of the steroid molecule are often designated A, B, C and D as shown.

The Novel Compounds

The novel compounds provided herein are anti-estrogenic agents that have both anti-estrogenic activity and reduced estrogenic activity, as may be determined by the degree of inhibition and degree of stimulation, respectively, of estradiol-induced alkaline phosphatase activity in human Ishikawa cells. The compounds of the invention have anti-estrogenic activity effective to inhibit $10^{-9}$M estradiol-stimulated alkaline phosphatase activity by at least 30% and estrogenic activity of less than about 5% relative to the stimulation of alkaline phosphatase activity by $10^{-9}$M estradiol. Preferred compounds of the invention have a 1,3,5-estratriene nucleus, and are substituted at either the C-17 position or the C-11 position with a molecular moiety which renders the compounds effective to competitively block the binding of estrogen to its receptor. Of these, the more preferred compounds are the 17-substituted, "17-desoxy" compounds, i.e., there is no oxygen atom bound directly to the C-17 position. Particularly preferred compounds are 17-desoxy-1,3,5-estratrienes that display tissue-selective pharmacology, i.e., compounds that act as SERMs by virtue of displaying estrogen antagonism in reproductive tissue but producing beneficial estrogen-like effects elsewhere in the body, particularly on bone and lipid metabolism.

Formula (I) represents a first group of exemplary compounds of the invention

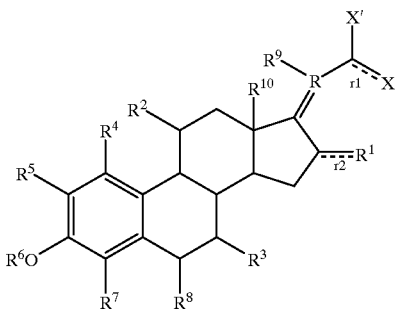

(I)

in which r1 and r2 represent optional double bonds, and R is selected from the group consisting of C and N, and, when R is C, is in either the E or Z configuration. In preferred compounds herein, R is C.

The other substituents, X, X' and $R^1$ through $R^{10}$, are defined as follows.

X is hydrocarbyl generally and preferably including at least one oxygen atom, sulfur atom, and/or nitrogen atom in the form of an —O—, —S—, —NH— or —N(alkyl)-, preferably an —N(lower alkyl)-, linkage, and optionally containing additional substituents and functional groups such as hydroxyl, oxo, alkoxy, amino, alkyl-substituted amino, halogeno, aryl, heteroaryl, heterocycloalkyl, or the like. When r1 is present, such that the linkage to X is through a double bond, preferred X moieties are CH—Y and N—Y. When r1 is not present, such that the linkage to X is through a single bond, preferred X moieties are represented by —Z—Y, —CH—$Y^1Y^2$ or —$NR^{26}$Y, wherein Y, $Y^1$ and $Y^2$ are as defined below, Z is oxygen or sulfur, and $R^{26}$ is hydrogen or lower alkyl. In preferred structures herein, r1 is not present.

X' is either hydrogen or hydrocarbyl, wherein, if hydrocarbyl, generally and preferably including at least one oxygen atom, sulfur atom, and/or nitrogen atom in the form of an —O—, —S—, —NH— or —N(alkyl)-linkage, and optionally containing additional substituents and functional groups, as explained above with respect to X. X and X' may be the same or they may be different. Alternatively, X and X' may be linked to form a heterocyclic ring, typically a six- to eight-membered heterocycloalkyl ring containing one to three, preferably two or three, heteroatoms selected from the group consisting of nitrogen, oxygen, and sulfur, with nitrogen and oxygen preferred. The heterocycloalkyl group may, for example, have the structure —$Z^1$—$(CH_2)_{n1}$—$N(R^{27})$—$(CH_2)_{n2}$—$Z^2$— wherein n1 and n2 are 1 or 2, and are preferably although not necessarily the same, $R^{27}$ is hydrogen or lower alkyl, and $Z^1$ and $Z^2$ are independently oxygen or sulfur.

Y is hydrogen, —$(R^{28})_{n3}$—J$R^{29}R^{30}$ or —$(R^{31})_{n4}$—$Z^3$—$(R^{32})_{n5}$—[L—$(R^{33})_{n6}]_{n7}$—[$Z^4$—$(R^{34})_{n8}]_{n9}$—J$R^{29}R^{30}$ wherein $R^{28}$, $R^{31}$, $R^{32}$, $R^{33}$ and $R^{34}$ are alkylene or alkenylene, typically alkylene, preferably lower alkylene, and $Z^3$ and $Z^4$ are independently oxygen or sulfur. L is —C(O)—, O, S or —$NR^{35}$—, wherein $R^{35}$ is hydrogen or lower alkyl, or L may be a five- or six-membered cyclic structure, optionally containing 1 to 4 heteroatoms selected from the group consisting of N, O and S and combinations thereof and optionally substituted with one or more substituents selected from the group consisting of alkyl, alkenyl, alkoxy, halogenated alkyl, alkenyl, and alkoxy (preferably lower alkyl, lower alkenyl, lower alkoxy, halogenated lower alkyl, halogenated lower alkenyl, and halogenated lower alkoxy), carboxyl, hydroxy, amino, nitro, cyano, halogen, halogenated alkyl, alkenyl, and alkoxy, and L may, optionally, be an arylene ring, and if arylene, is preferably phenylene, halo-substituted phenylene, lower alkyl-substituted phenylene, lower alkoxy-substituted phenylene, or biphenylene, more preferably phenylene, methoxy-substituted phenylene or iodo-substituted phenylene (with $R^{33}$ bound to any one of the ring carbon atoms). J is N or CH, n3 and n4 are 0 or 1, but are necessarily 1 when Y is bound to an oxygen, sulfur or nitrogen atom, n5, n6, n7, n8 and n9 are independently 0 or 1, and $R^{29}$ and $R^{30}$ may be the same or different and are independently selected from the group consisting of hydrogen, lower alkyl, and haloalkyl, or together form a monocyclic or polycyclic substituent, with a preferred monocyclic substituent represented as J', below,

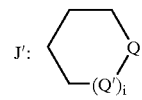

wherein Q is $NR^{36}$, O or $CH_2$, Q' is oxo or $CH_2$, and i is 0 or 1. Y is optionally substituted at one or more available carbon atoms with halogen, oxo, hydroxyl, lower alkyl, lower alkoxy or lower haloalkyl, with the provisos that when X is O—Y and R is C, Y is other than hydrogen, and when J is CH, $R^{29}$ and $R^{30}$ together form J'.

$Y^1$ and $Y^2$ may be the same or different and are defined by —Z—Y. Alternatively, $Y^1$ and $Y^2$ may be linked to form a heterocyclic ring, typically a heterocycloalkyl ring as explained with respect to X and X', above.

The identity of $R^1$ is dependent on the presence or absence of a double bond at r2. When r2 is present, such that there is a double bond linking $R^1$ to the carbon atom at the 16-position of the estratriene nucleus, then $R^1$ is $CR^{11}R^{12}$, wherein $R^{11}$ and $R^{12}$ are independently either hydrogen or lower alkyl. The preferred $R^1$ group when r2 is present is $CH_2$. When r2 is absent, such that there is a single bond linking $R^1$ to the carbon atom at the 16-position, then $R^1$ is hydrogen, alkyl (preferably lower alkyl) or halogen, preferably hydrogen.

$R^2$ is selected from the group consisting of hydrogen, hydroxyl, alkyl, alkenyl, (preferably lower alkyl and alkenyl), aryl, alkaryl, —$ONO_2$, —$OR^{13}$ and —$SR^{13}$, wherein $R^{13}$ is alkyl (preferably lower alkyl), lower acyl or aryl. Preferably, although not necessarily, $R^2$ is hydrogen.

$R^3$ is selected from the group consisting of hydrogen, hydroxyl, halogen, alkyl alkenyl (preferably lower alkyl or alkenyl), aryl, alkaryl, —$OR^{13}$ and —$SR^{13}$, wherein $R^{13}$ is as defined above. Preferred $R^3$ substituents are hydrogen and lower alkyl.

$R^4$ is hydrogen or lower alkyl, preferably hydrogen.

$R^5$ is selected from the group consisting of hydrogen, lower alkoxy, halogen, cyano, —$CH_2CH=CH_2$, —CHO, —$NR^{14}R^{15}$ and —$(CH_2)NR^{14}R^{15}$ wherein $R^{14}$ and $R^{15}$ may be the same or different and are either hydrogen or lower alkyl, or together form a five- or six-membered cycloalkyl group optionally containing an additional nitrogen heteroatom. Preferably, $R^5$ is hydrogen, methoxy, —$NR^{14}R^{15}$ or —$(CH_2)NR^{14}R^{15}$ wherein $R^{14}$ and $R^{15}$ are lower alkyl, particularly methyl or ethyl.

$R^6$ is selected from the group consisting of hydrogen, alkyl, acyl (preferably lower alkyl or lower acyl), —C(O)-aryl, —C(O)-alkyl and —$SO_2NH_2$ (sulfamate). Preferred $R^6$ substituents are hydrogen, sulfamate, —C(O)—$C_6H_5$, and —C(O)-t-butyl, with hydrogen and sulfamate particularly preferred.

$R^7$ is selected from the group consisting of hydrogen, halogen, —$NO_2$, —CHO, —$CH_2CH=CH_2$, —$NR^{16}R^{17}$ and —$(CH_2)NR^{16}R^{17}$ wherein $R^{16}$ and $R^{17}$ may be the same or different and are either hydrogen, lower alkyl or acetyl. Preferably, $R^7$ is hydrogen.

$R^8$ is selected from the group consisting of hydrogen, hydroxyl, —$OR^{18}$ and —$SR^{18}$ wherein $R^{18}$ is alky, acyl (preferably lower alkyl or lower acyl) or aryl. In preferred compounds, $R^8$ is hydrogen.

$R^9$ is hydrogen or lower alkyl, with the proviso that when R is N, $R^9$ is not present. When $R^9$ is present, it is preferably hydrogen or methyl.

$R^{10}$ is methyl or ethyl, typically ethyl.

Formula (II) represents a second group of exemplary compounds of the invention

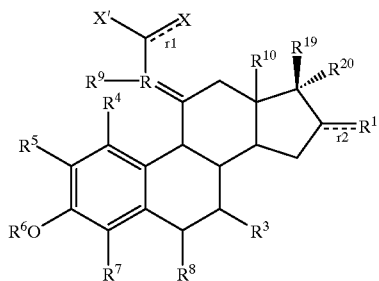

(II)

in which:

r1, r2, R, $R^1$, $R^3$, $R^4$, $R^5$, $R^6$, $R^7$, $R^8$, $R^9$, $R^{10}$, X and X' are as defined above with respect to formula (I) compounds; and $R^{19}$ and $R^{20}$ are independently selected from the group consisting of hydrogen, hydroxyl, alkyl, alkenyl, alkynyl, alkoxy (preferably lower alkyl, lower alkenyl, lower alkynyl, and lower alkoxy), and halogen, or $R^{19}$ and $R^{20}$ together form =O.

Preferred compounds of structural formulae (I) and (II) are compounds wherein r1 is not present, R is C, $R^3$ is hydrogen or methyl, X is —O—Y or —S—Y, Y is —$(CH_2)_{m1}$—$NR^{29}R^{30}$ or —$(CH_2)_{m2}$—O—$(CH_2)_{m3}$—[L—$(CH_2)_{m4}]_{n7}$—[O—$(CH_2)_{m5}]_{n9}$—$NR^{29}R^{30}$ wherein L is phenylene, methoxy-substituted phenylene, iodo-substituted phenylene, —NH—, —$N(CH_3)$— or —O—, m1 through m5 are 1, 2, 3 or 4, $R^{29}$ and $R^{30}$ are hydrogen, lower alkyl, haloalkyl (preferably lower haloalkyl), or are linked together to form a heterocycloalkyl ring such as defined by J' earlier herein, together representing, for example, —$CH_2CH_2$—NH—$CH_2CH_2$—, —$CH_2CH_2$—O—$CH_2CH_2$—, —$(CH_2)_4$—, —$(CH_2)_5$—, or the like, and $R^6$ is hydrogen or sulfamate. Preferred compounds of structural formula (II), in particular, are wherein one of $R^{19}$ and $R^{20}$ is hydrogen and the other is hydroxyl, lower alkyl or lower alkynyl, or wherein $R^{19}$ and $R^{20}$ together form =O.

Formula (III) represents a third group of exemplary compounds of the invention

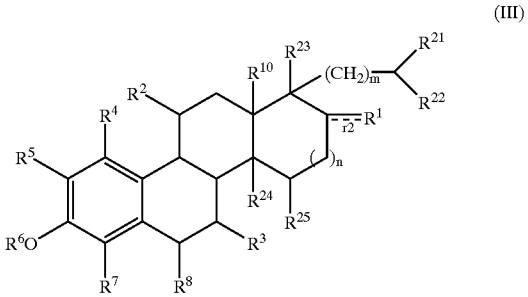

(III)

in which r2 and $R^1$ through $R^8$ and $R^{10}$ are as defined above with respect to Formulae (I) and (II), and the remaining substituents are as follows:

$R^{21}$ is hydrocarbyl generally and preferably including at least one oxygen atom, sulfur atom, and/or nitrogen atom in the form of an —O—, —S—, —NH— or —N(alkyl)-preferably —N(lower alkyl)-) linkage, and optionally including additional substituents and functional groups such as hydroxyl, oxo, alkoxy, amino, substituted amino, halogeno, aryl, heteroaryl, heterocycloalkyl, or the like. Typical $R^{21}$ substituents are represented by —$(R^{28})_{n3}$—$JR^{29}R^{30}$ and —$(R^{31})_{n4}$—$Z^3$—$(R^{32})_{n5}$—[L—$(R^{33})_{n6}]_{n7}$—[$Z^4$—$(R^{34})_{n8}]_{n9}$—$JR^{29}R^{30}$ wherein $R^{28}$, $R^{29}$, $R^{30}$, $R^{31}$, $R^{32}$, $R^{33}$, $R^{34}$, $Z^3$, $Z^4$, L, J, and n3 through n9 are as defined above. Examples of $R^{21}$ substituents within the aforementioned group are —$(CH_2)_{m1}$—$NR^{29}R^{30}$ and —$(CH_2)_{m2}$—O—$(CH_2)_{m3}$—[L—$(CH_2)_{m4}]_{n7}$—[(O—$(CH_2)_{m5}]_{n9}$—$NR^{29}R^{30}$ wherein L is phenylene, methoxy-substituted phenylene, iodo-substituted phenylene, —NH—, —$N(CH_3)$— or —O—, m1 through m5 are 1, 2, 3 or 4, $R^{29}$ and $R^{30}$ are hydrogen, lower alkyl, haloalkyl (typically lower haloalkyl), or are linked together to form a heterocycloalkyl ring as explained above, but preferably $R^{29}$ and $R^{30}$ are lower alkyl, most preferably methyl or ethyl.

$R^{22}$ is hydrogen or alkyl, or, when m is 0, $R^{21}$ and $R^{22}$ may be linked to form a five- or six-membered cyclic structure which may or may not be aromatic, contains 0 to 3 heteroatoms selected from the group consisting of N, O and S, and is substituted with 0 to 4 substituents selected from the group consisting of alkyl, alkenyl, alkynyl, alkoxy (preferably lower alkyl, alkenyl, alkynyl and alkoxy), —C(O)-alkyl, —C(O)—O-alkyl, —O—(CO)-alkyl (preferably —C(O)-lower alkyl, —C(O)—O-lower alkyl, and —O—(CO)-lower alkyl), —C(O)-aryl, hydroxyl, carboxyl, halogen, nitrile, nitrate and fluorinated alkyl. Preferably, $R^{22}$ is hydrogen or methyl.

$R^{23}$ is hydrogen or lower alkyl, typically hydrogen or methyl.

$R^{24}$ and $R^{25}$ are both hydrogen or are both methylene bound to each other through a single covalent bond.

In addition, m is an integer in the range of 0 to 6 inclusive, preferably 1, 2, 3 or 4, and n is 0 or 1.

Preferred compounds of structural formula (I) have the formula (Ia), as follows:

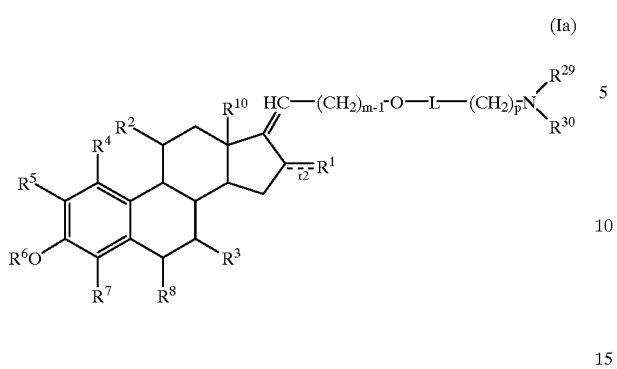

(Ia)

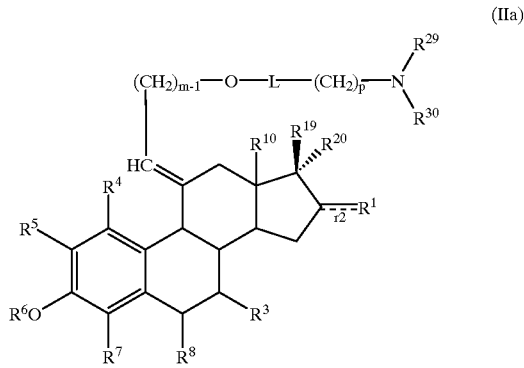

(IIa)

In structural formula (Ia), r2, $R^1$ through $R^8$ and $R^{10}$ are as defined with respect to the substituents of structural formula (I), the subscript "m" is an integer in the range of 0 to 6 inclusive, preferably 1, 2, 3 or 4, the subscript "p" is an integer in the range of 0 to 6 inclusive, preferably 1, 2, 3 or 4, $R^{29}$ and $R^{30}$ are lower alkyl, preferably methyl or ethyl, or are linked together to form a heterocycloalkyl ring, together representing, for example, —$CH_2CH_2$—NH—$CH_2CH_2$—, —$CH_2CH_2$—O—$CH_2CH_2$—, —$(CH_2)_4$—, —$(CH_2)_5$—, or the like, and L is a five- or six-membered cyclic structure that may or may not be aromatic, and optionally contains 1 to 4 heteroatoms selected from the group consisting of N, O and S and combinations thereof, and optionally substituted with one or more substituents selected from the group consisting of alkyl, alkenyl, alkoxy, halogenated alkyl, alkenyl, and alkoxy (preferably lower alkyl, lower alkenyl, lower alkoxy, halogenated lower alkyl, halogenated lower alkenyl, and halogenated lower alkoxy), carboxyl, hydroxy, amino, nitro, cyano, and halogen.

In structure (IIa), r2, $R^1$, $R^3$ through $R^8$, $R^{10}$, $R^{19}$ and $R^{20}$ are as defined with respect to compounds of structure (II), and m, p, L, $R^{29}$ and $R^{30}$ are as defined with respect to compounds of structure (Ia).

Particularly preferred compounds of structural formula (II) have the structure (IIb)

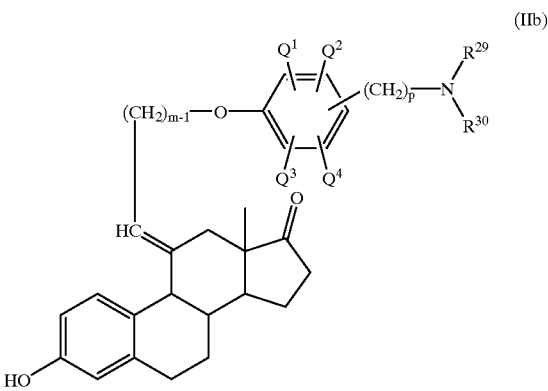

(IIb)

Particularly preferred compounds encompassed by structural formula (I) are those having the formula (Ib), as follows:

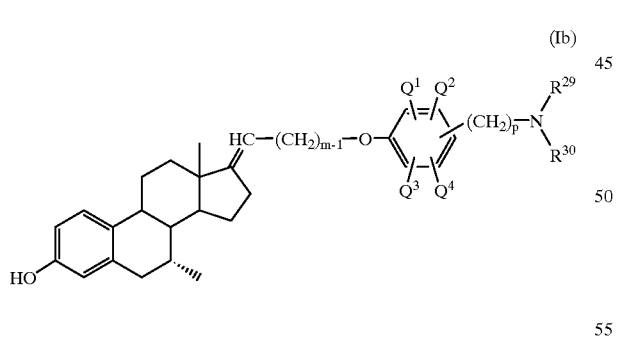

(Ib)

in which m, p, $R^{29}$ and $R^{30}$ are as defined above with respect to structure (Ia), and $Q^1$, $Q^2$, $Q^3$, $Q^4$ are as defined with respect to compounds of structural formula (Ib).

Preferred compounds of structural formula (III) have the structure (IIIa)

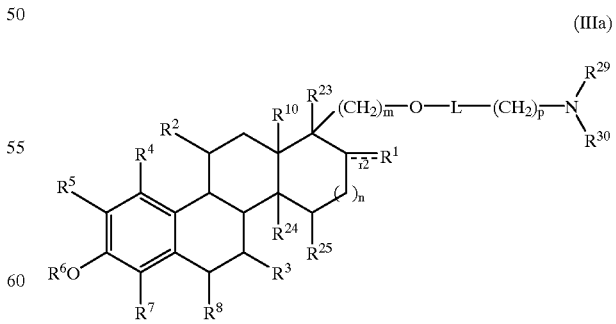

(IIIa)

wherein m, p, $R^{29}$ and $R^{30}$ are as defined above with respect to structure (Ia), and $Q^1$, $Q^2$, $Q^3$ and $Q^4$ are independenty selected from the group consisting of hydrogen, hydroxyl, carboxyl, alkoxy (preferably lower alkoxy), alkyl (preferably lower alkyl), halogen, amino, and lower alkyl-substituted amino.

Similarly, preferred compounds of structural formula (II) have the formula (IIa), as follows:

while particularly preferred compounds of formula (III) have the structure (IIIb), with all substituents as defined above with respect to compounds (Ia) and (Ib), respectively.

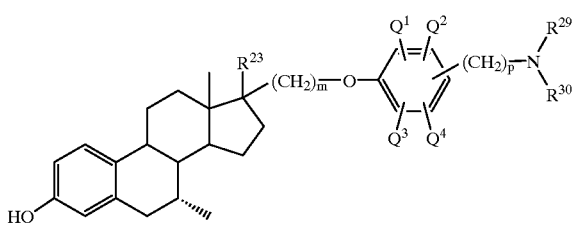

(IIIb)

at the C-11 or C-17 position, as well as 17-desoxy-1,3,5-estratrienes having the moiety

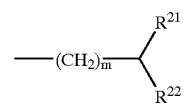

preferably

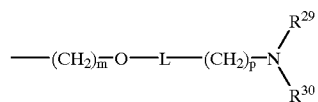

Thus, it will be appreciated by those skilled in the art that the preferred compounds of the invention are 17-desoxy-1,3,5-estratrienes having the moiety

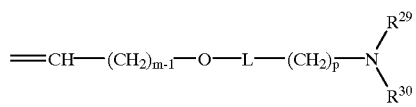

preferably

and most preferably

and most preferably

present at C-17.

Importantly, the novel compounds of this invention in which $R^6$ is —$SO_2NH_2$ are potent anti-estrogenic agents as well as prodrugs for the parent anti-estrogenic compounds which are generated in vivo by hydrolysis of the —$SO_2NH_2$ group at the C-3 position.

Examples of specific compounds of the invention include, but are not limited to, the following:

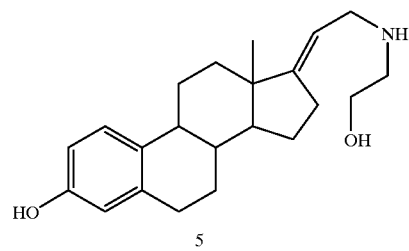

5

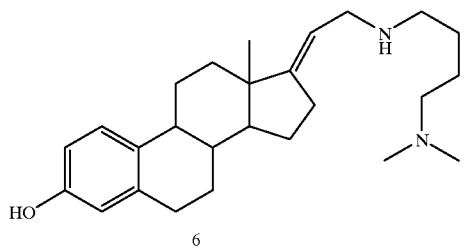

6

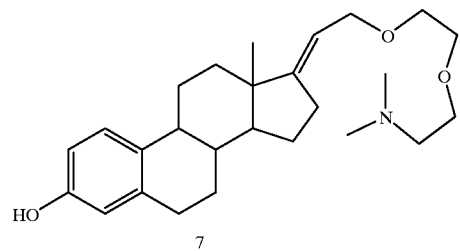

7

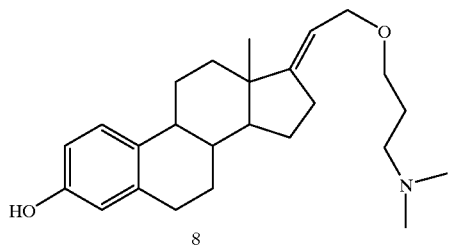

8

-continued
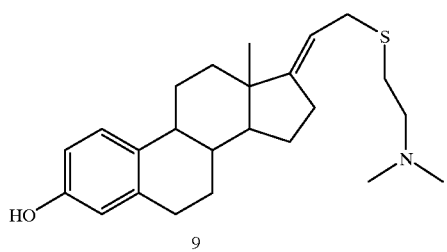
9
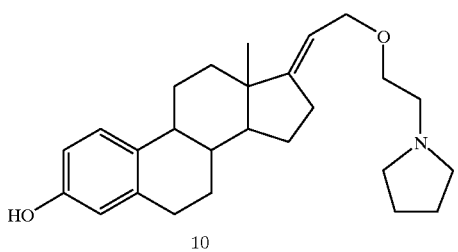
10
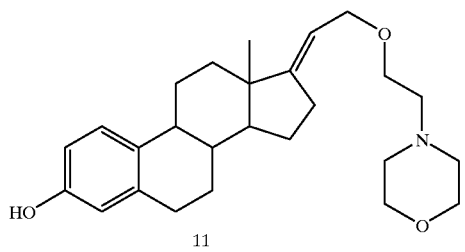
11
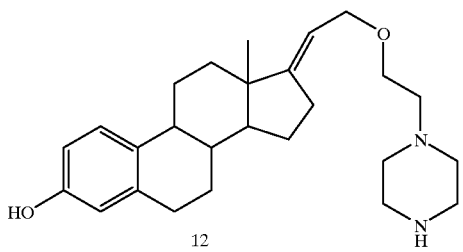
12
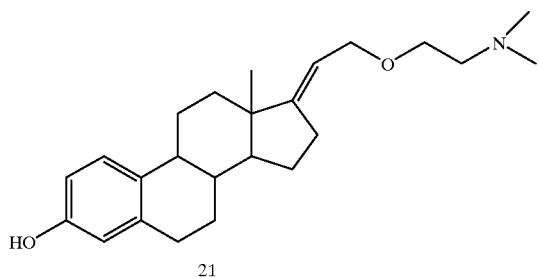
21
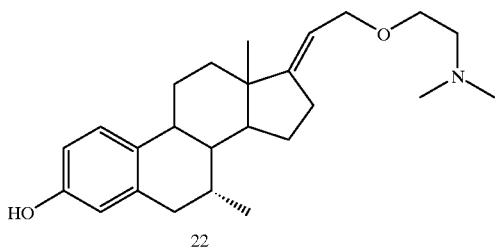
22
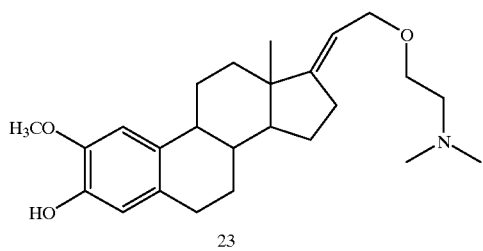
23
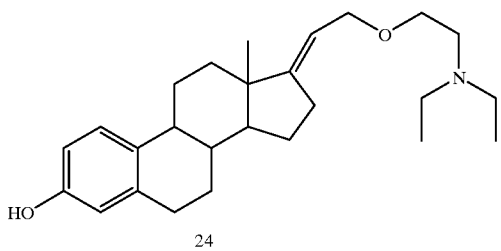
24
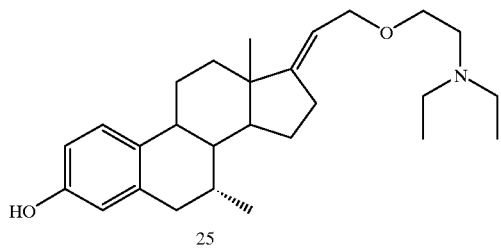
25
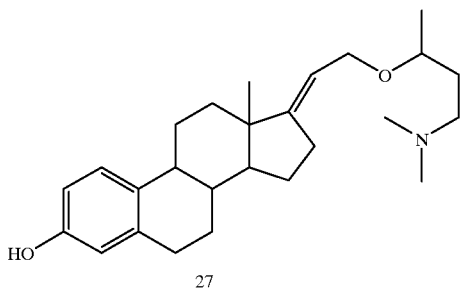
27
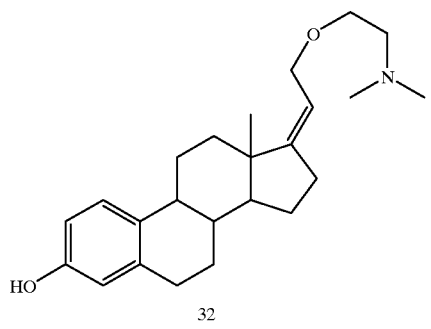
32
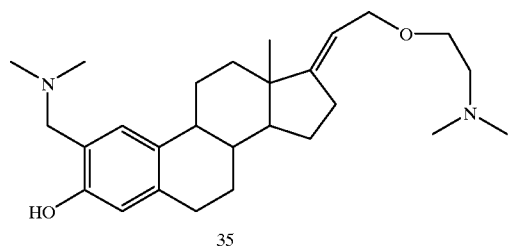
35

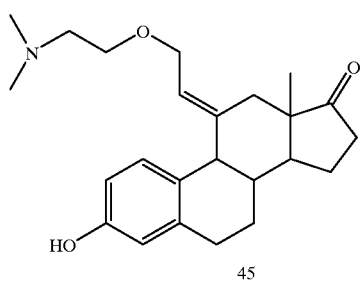
45
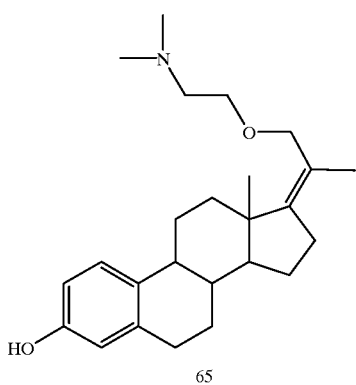
65
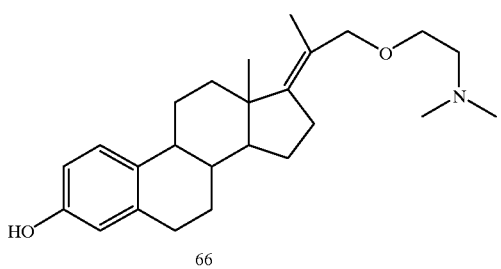
66
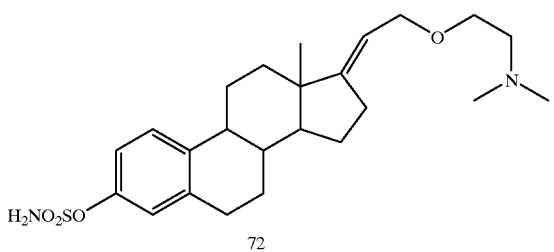
72
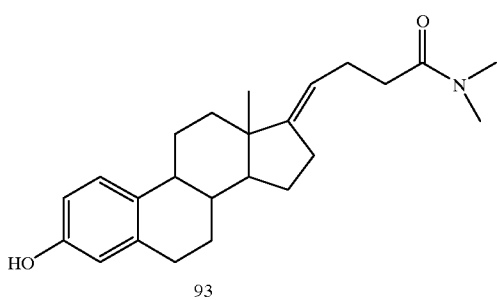
93
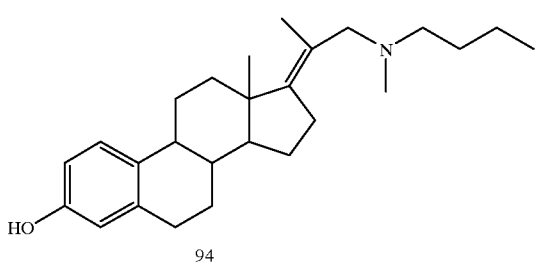
94
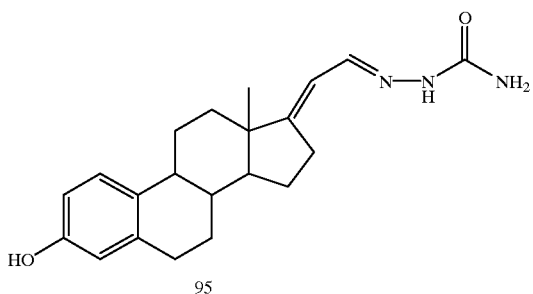
95
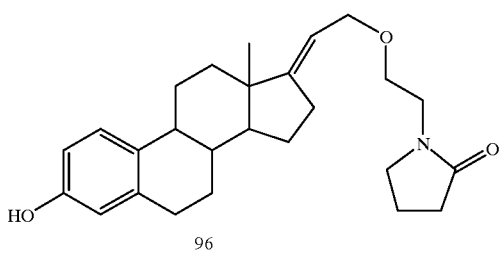
96
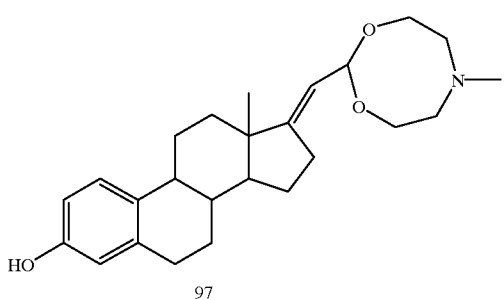
97
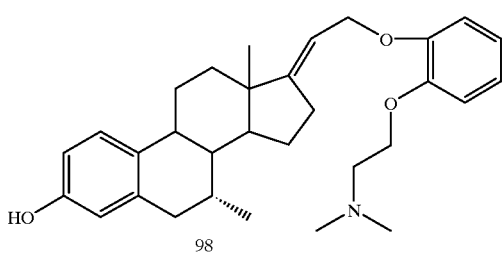
98

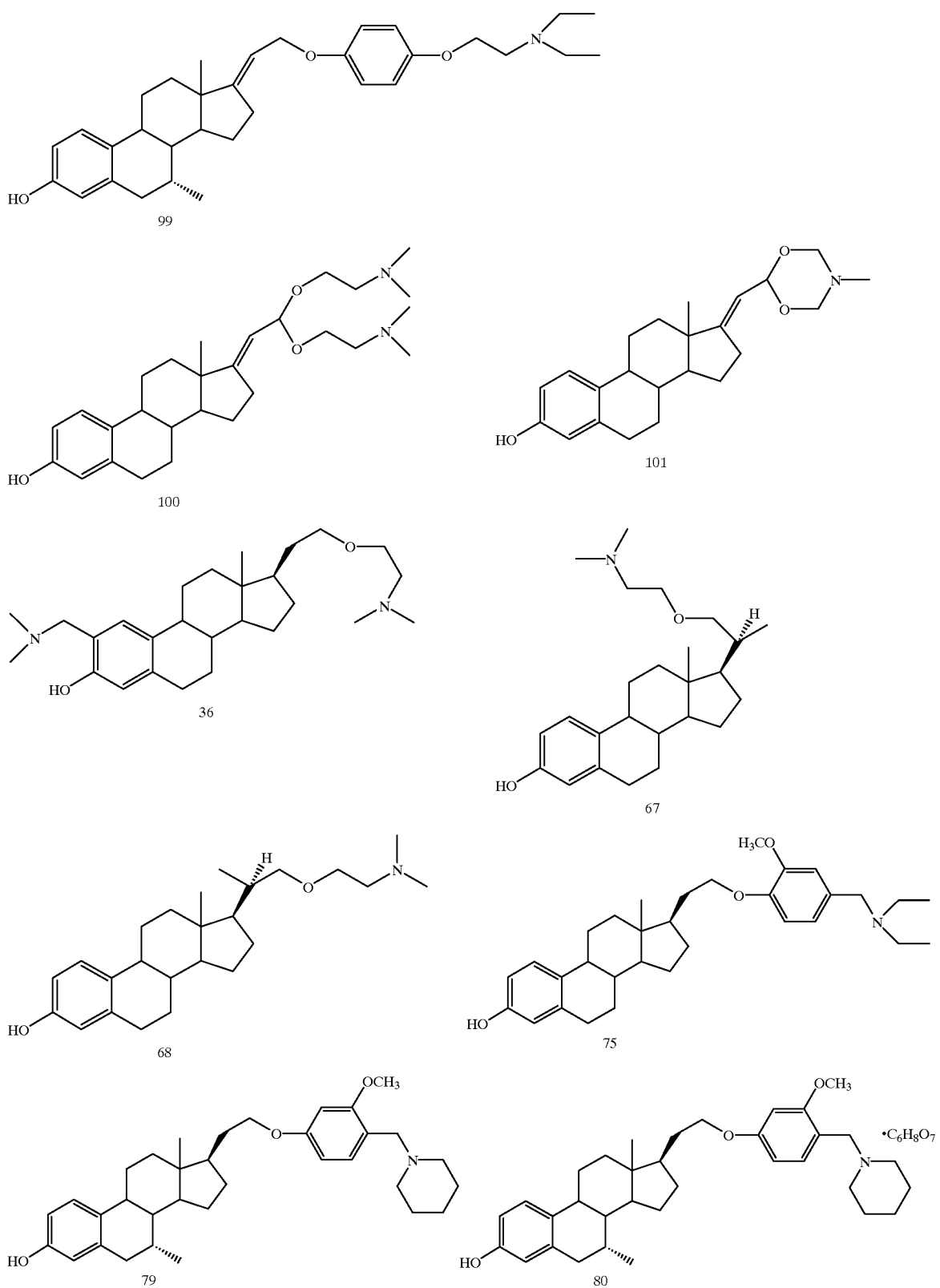

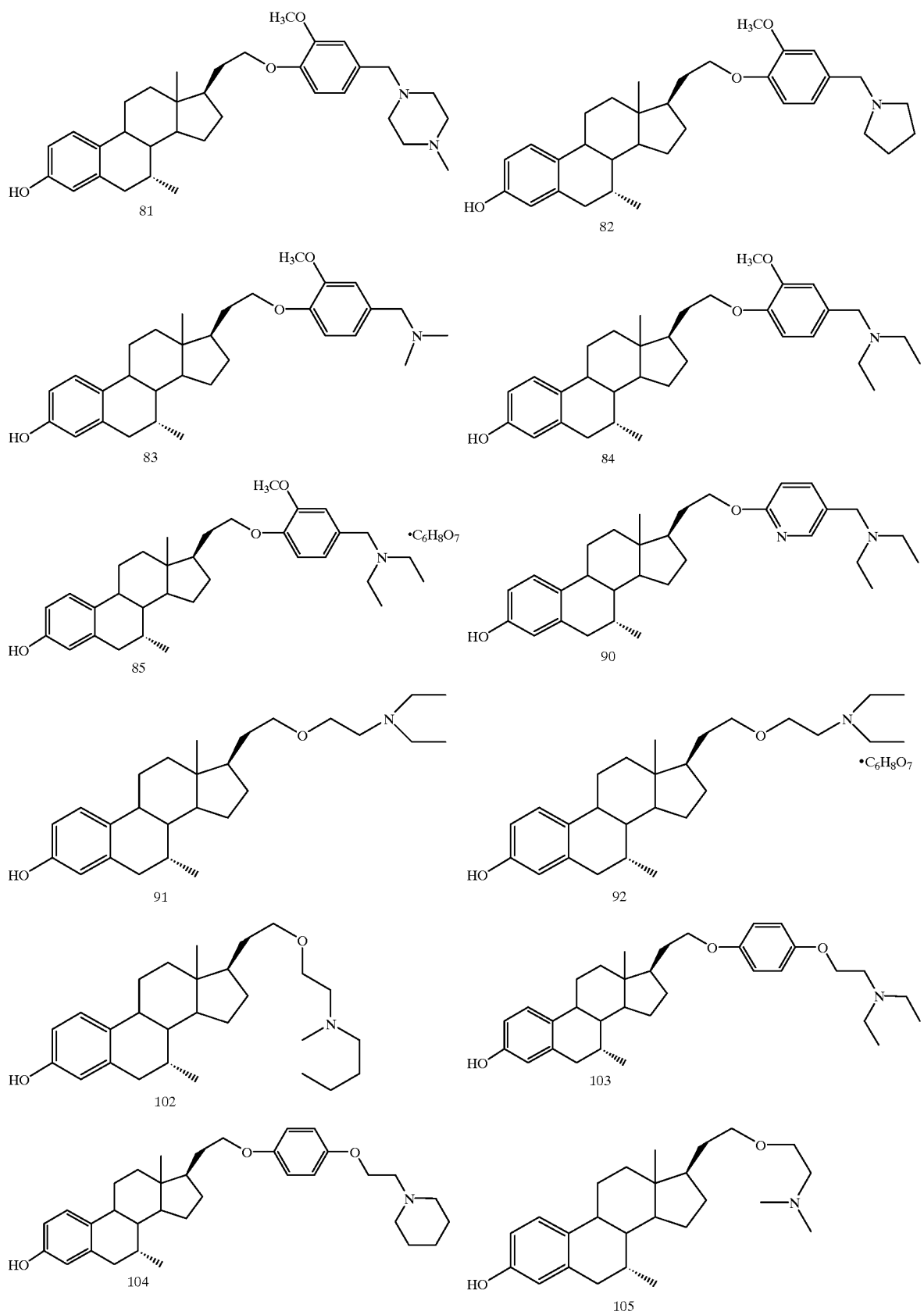

-continued

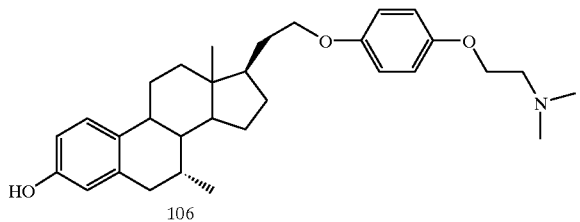
106

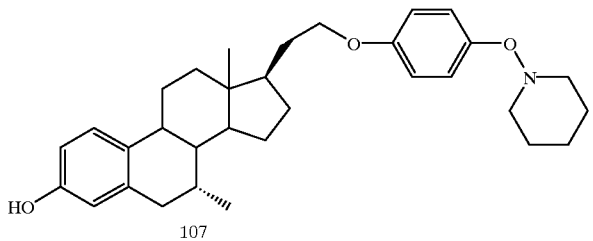
107

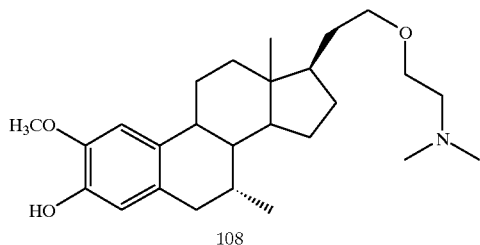
108

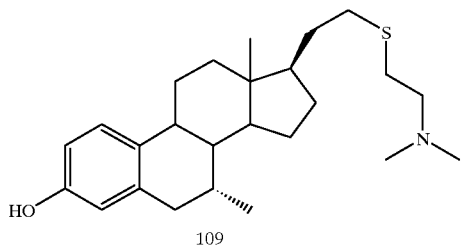
109

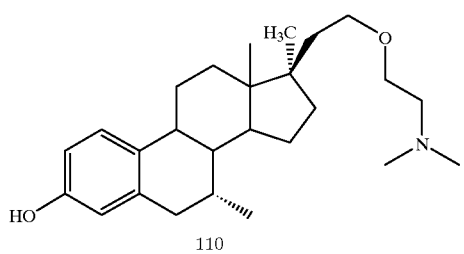
110

The compounds may be in the form of pharmaceutically acceptable salts, esters, amides, prodrugs or other derivatives or analogs, or they may be modified by appending one or more appropriate functionalities to enhance selected biological properties. Such modifications are known in the art and include those which increase biological penetration into a given biological system increase oral bioavailability, increase solubility to allow administration by injection, and the like.

Salts of the compounds can be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Acid addition salts are prepared from the free base (e.g., compounds having a neutral —$NH_2$ or cyclic amine group) using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fbmaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preferred acid addition salts of the present compounds are the citrate, fumarate, succinate, benzoate and malonate salts.

Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trinmethylamine, or the like.

Preparation of esters involves functionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Esters can be reconverted to the free acids, if desired, by using conventional hydrogenolysis or hydrolysis procedures. Methods for preparing amides, prodrugs, and other analogs and derivatives of the present compounds, are, similarly, within the knowledge of one skilled in the art and/or described in the pertinent literature and texts.

Certain of the novel compounds are chiral in nature and can thus be in enantiomerically pure form or in a racemic mixture. In some cases, i.e., with regard to certain specific compounds illustrated herein, chirality is indicated. In other cases, it is not, and the invention is intended to encompass both the isomerically pure forms of the compounds shown and the racemic or diastereomeric mixtures thereof. For example, compounds of structural formula (III) are shown as having two substituents at the 17-position of the steroid nucleus without an indication of which substituent is 17α and which is 17β. It is intended that either possibility is encompassed by the generic structure, i.e., $R^{23}$ may be α and —$(CH_2)_n$—$CHR^{21}R^{22}$ may be β or $R^{23}$ may be β and —$(CH_2)_n$—$CHR^{21}R^{22}$ may be α. Furthermore, certain compounds are stereoisomers which are asymmetric with respect to a C=C bond. In such a case, as indicated above with respect to the structures of formulae (I) and (II), the invention encompasses both such structures, i.e., both the "E" and "Z" isomers and mixtures thereof.

Utility and Administration

The novel compounds can be used to treat a variety of disorders; primarily, the compounds are useful to treat estrogen-dependent disorders, i.e., conditions or diseases that are estrogen-induced or estrogen stimulated. The present compounds are capable of inducing remissions in breast cancer, including metastatic tumors. Furthermore, the present compounds have utility in the treatment of ovarian, uterine and pancreatic tumors as well as disease conditions such as galactorrhea, McCune-Albright syndrome, benign breast disease, and endometriosis. The compounds are also useful for treating certain conditions and disorders which are not estrogen-dependent, e.g., non-estrogen-dependent cancers, particularly cancers which are multiple drug-resistant. The latter advantage of the novel compounds represents an important advance in the art, as a major problem affecting the efficacy of chemotherapy regimens is the evolution of cells which, upon exposure to a chemotherapeutic drug, become resistant to a multitude of structurally unrelated drugs and therapeutic agents.

As explained elsewhere herein, certain of the novel compounds display tissue-selective pharmacology and act as SERMs. That is, the compounds are estrogen antagonists in reproductive tissue, including breast and/or uterine tissue, while giving rise to estrogen-like effects elsewhere in the body, particularly in the bone and lipid metabolism. A number of compounds of the invention, particularly those compounds defined by structural formula (III) herein, are tissue-selective anti-estrogenic agents as just defined. Other compounds within the scope and substance of the invention may display tissue-selective pharmacology as well, and those skilled in the art may carry out conventional procedures, not involving excessive or undue experimentation, in order to ascertain a compound's potential tissue selectivity.

Those compounds useful as SERMs can be used to treat all of the estrogen-dependent disorders discussed above, i.e., breast cancer, ovarian, uterine and pancreatic tumors, galactorrhea, McCune-Albright syndrome, benign breast disease, and endometriosis. In addition, the novel compounds herein that are tissue selective in nature may also be used as follows:

(1) to inhibit pulmonary hypertensive diseases, as described in U.S. Pat. No. 5,447,941 to Zuckerman;

(2) to inhibit dysfunctional uterine bleeding, as described in U.S. Pat. No. 5,552,416 to Keohane;

(3) to inhibit weight gain or induce or facilitate weight loss, as described in U.S. Pat. Nos. 5,578,613 and 5,578,614 to Bryant et al.;

(4) to inhibit breast disorders such as gynecomastia, hypertrophy, polythelia, mastodynia/mastalgia, hyperprolactinemia, and non-fibrocystic, non-cancerous mastopathias, as described in U.S. Pat. No. 5,593,987 to Cullinan et al.;

(5) to inhibit atrophy of the skin and vagina, as described in U.S. Pat. No. 5,610,167 to Cullinan;

(6) to inhibit bone loss and lower serum cholesterol, as described in U.S. Pat. No. 5,641,790 to Draper;

(7) to increase bone mass, as described in U.S. Pat. No. 5,510,370 to Hock;

(8) to treat osteoporosis, as described in U.S. Pat. No. 5,646,137 to Black et al.;

(9) to inhibit CNS problems in post-menopausal women, as described in U.S. Pat. No. 5,663,184 to Bryant et al.; and

(10) to inhibit ovarian dysgenesis, delayed puberty or sexual infantilism, as described in U.S. Pat. No. 5,719,165 to Dodge.

It will be appreciated by those skilled in the art that numerous other uses of the present compounds are possible as well.

In addition to the novel compounds described above, the invention further encompasses methods of using certain known compounds as anti-estrogenic agents, i.e., compounds which were previously known to be useful only for purposes unrelated to the treatment of estrogen-dependent disorders. These compounds include

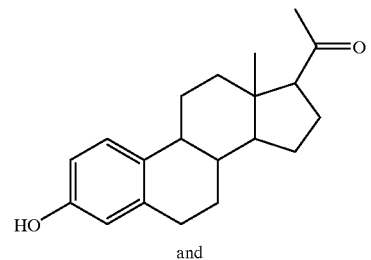

and

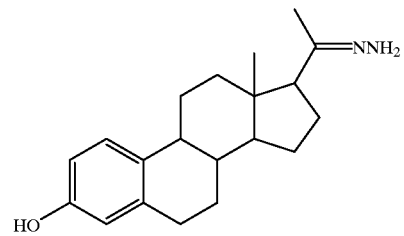

The anti-estrogenic agents of the invention may be conveniently formulated into pharmaceutical compositions composed of one or more of the compounds in association with a pharmaceutically acceptable carrier. See Remington: The Science and Practice of Pharmacy, 19th Ed. (Easton, Pa.: Mack Publishing Co., 1995), which discloses typical carriers and conventional methods of preparing pharmaceutical compositions which may be used as described or modified to prepare pharmaceutical formulations containing the compounds of the invention. The compounds may also be administered in the form of pharmaceutically acceptable salts, or as pharmaceutically acceptable esters, as described in the preceding section.

The compounds may be administered orally, parenterally, transdermally, rectally, nasally, buccally, vaginally or via an implanted reservoir in dosage formulations containing conventional non-toxic pharmaceutically acceptable carriers, adjuvants and vehicles. The term "parenteral" as used herein is intended to include subcutaneous, intravenous, and intramuscular injection. The amount of active compound administered will, of course, be dependent on the subject being treated, the subject's weight, the manner of administration and the judgment of the prescribing physician. Generally, however, dosage will be in the range of approximately 0.01 mg/kg/day to 10.0 mg/kg/day, more preferably in the range of about 1.0 mg/kg/day to 5.0 mg/kg/day.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* referenced above.

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent is combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringers solution and isotonic sodium chloride solution. In addition, sterile, fixed oils are conventionally employed as a solvent or suspending medium. A more recently revised approach for parenteral administration involves use of a slow release or sustained release system, such that a constant level of dosage is maintained. See, e.g., U.S. Pat. No. 3,710,795.

The compounds of the invention may also be administered through the skin or mucosal tissue using conventional transdermal drug delivery systems, wherein the agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present; the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery devices may be fabricated using conventional techniques, known in the art, for example by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by soaking in a drug/vehicle mixture.

The laminated transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well know in the art and include, for example, dixnethylsulfoxide (DMSO), dimethyl formamide (DHMF), N,N-dimethylacetamide (DMA), decylmethylsulfoxide ($C_{10}$MSO), $C_2$–$C_6$ alkanediols, and the 1-substituted azacycloheptan-2-ones, particularly 1-n-dodecylcyclaza-cycloheptan-2-one (available under the trademark Azone® from Whitby Research Incorporated, Richmond, Va.), alcohols, and the like. However, it should be emphasized that an advantage of the present invention is the potential for transdermal delivery of an active agent as provided herein without need for a skin permeation enhancer; this is particularly true, for example, with compounds of structural formulae (I) and (III) wherein a nitrato (—$ONO_2$) group is present at the 11-position.

Alternatively, the pharmaceutical compositions of the invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferred formulations for vaginal drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

The specific ointment or cream base to be used, as will be appreciated by those skilled in the art, is one that will provide for optimum drug delivery. As with other carriers or vehicles, an ointment base should be inert, stable, nonirritating and nonsensitizing. Also preferred are vaginal suppositories. Suppositories may be formulated using conventional means, e.g., compaction, compression-molding or the like, and will contain carriers suited to vaginal drug delivery, typically a bioerodible material which provides for the desired drug release profile.

Formulations for buccal administration include tablets, lozenges, gels and the like. Alternatively, buccal administration can be effected using a transmucosal delivery system.

Process for Preparation

The compounds of the invention may be prepared in high yield using relatively simple, straightforward methods as exemplified in the experimental section herein. Syntheses of representative compounds are detailed in Examples 1 through 39. For further information concerning the synthesis of compounds having a sulfamate group at the 3-position, reference may be had to co-pending, commonly assigned U.S. Patent Application Ser. No. 08/997,416, entitled "Estrone Sulfamate Inhibitors of Estrone Sulfatase, and Associated Pharmaceutical Compositions and Methods of Use," inventors Tanabe et al., filed on Dec. 24, 1997.

Experimental

The practice of the present invention will employ, unless otherwise indicated, conventional techniques of synthetic organic chemistry, biological testing, and the like, which are within the skill of the art. Such techniques are explained fully in the literature. See, e.g., Fieser et al., *Steroids* (New York: Reinhold, 1959), Djerassi, *Steroid Reactions: An Outline for Organic Chemists* (San Francisco: Holden-Day, 1963), and Fried et al., *Organic Reactions in Steroid Chemistry*, vols. 1 and 2 (New York: Reinhold, 1972), for detailed information concerning steroid-related synthetic procedures. Reference may be had to Littlefield et al., *Endocrinology* 127: 2757–2762 (1990) and Wakeling et al., *Endocrinology* 99: 447–453 (1983) for a description of the biological testing procedures useful to evaluate compounds such as those described and claimed herein. All patents, patent applications, and publications mentioned herein, both supra and infra, are hereby incorporated by reference.

It is to be understood that while the invention has been described in conjunction with the preferred specific embodiments thereof that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to insure accuracy with respect to numbers used (e.g., amounts, temperature, etc.) but some experimental error and deviation should be accounted for. Unless indicated otherwise, temperature is in degrees C. and pressure is at or near atmospheric. All solvents were purchased as HPLC grade, and all reactions were routinely conducted under an inert atmosphere of argon unless otherwise indicated. All reagents were obtained commercially unless otherwise indicated. Estrone and estrdiol were purchased from Berlichem U.S.; ethynyl estradiol was purchased from Akzo Nobel. NMR analyses were conducted on a Varian Gemini 300 and were referenced to chloroform at δ7.27. FTIR spectra were recorded on a Perkin-Elmer 1610.

EXAMPLE 1

Preparation of (E)-3-tert-Butyldimethylsilyloxy-21-bromo-19-norpregna-1,3,5(10),17(20)-tetraene (4)

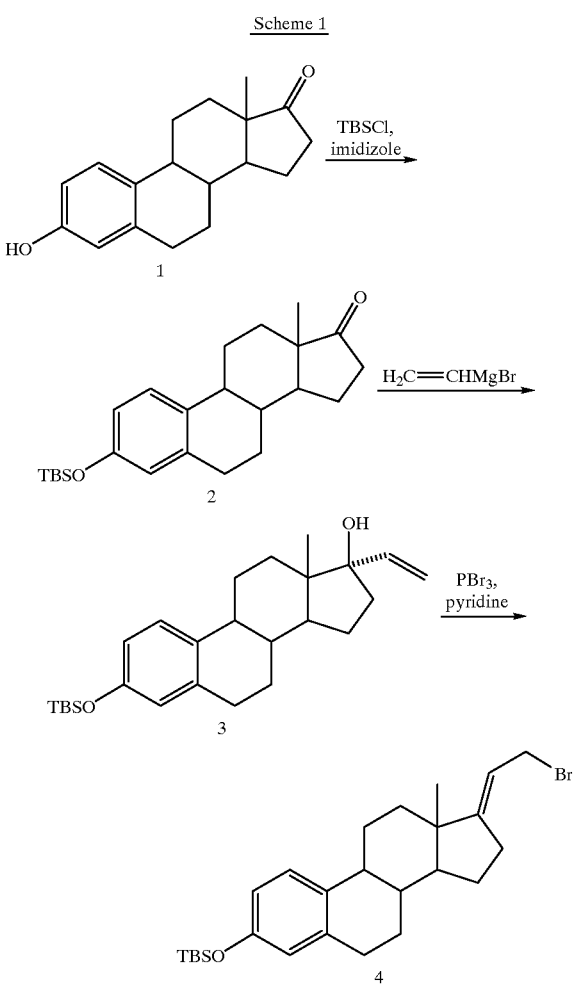

Scheme 1

(a) Synthesis of 3-tert-Butyldimethylsilyloxy-estra-1,3,5 (10)-triene-17-one (2)

To a mixture of estrone (1, 29 g, 107.3 mmol) and tert-butyldimethylsilyl chloride (18 g 118 mmol) in THF (350 mL) at room temperature under argon was added imidazole (18 g, 264 mmol) in DMF (350 mL). After stirring the reaction mixture overnight, the THF was evaporated and the reaction mixture was poured onto ice water. The resulting white precipitate was collected by filtration, dissolved in $CH_2Cl_2$, and the solution was dried ($MgSO_4$). The desiccant was filtered and the solvent was evaporated under reduced pressure to afford 38.8 g of 2 as a white, crystalline solid (94% yield), m.p. 171–172 ° C.

¹H NMR (300 MHz, CDCl₃): δ0.19 (s, 6, Si(CH₃)₂), 0.91 (s, 3, CH₃), 0.98 (s, 9, SiC(CH₃)₃), 1.24–2.57 (m, 13), 2.85 (m, 2), 6.57 (d, J=2.4 Hz, 1, ArH), 6.62 (dd, J=2.4, 8.4 Hz, 1, ArH), 7.12 (d, J=8.4 Hz, 1, ArH).

(b) Synthesis of 3-tert-Butyldimethylsilyloxy-19-nor-17α-pregna-1,3,5(10),20-tetraen-17-ol (3)

To a solution of 3-tert-butyldimethylsilyloxy-estra-1,3,5(10)-triene-17-one (2, 4.0 g, 10.4 mmol) in THF (40 mL) at 0° C. under argon was added a solution of vinylmagnesium bromide in THF (15 mL, 15 mmol). The resulting mixture was then warmed to room temperature for 2 h. The reaction mixture was quenched by pouring into saturated aqueous NH₄Cl, then extracted with 40% ethyl acetate/hexane. The combined organic layers were dried (MgSO₄). The desiccant was filtered and the solvent was evaporated at reduced pressure. Flash chromatography (5% ethyl acetate/hexane) afforded 2.23 g of 3 as a white solid (52% yield), m.p. 127–128° C.

¹H NMR (300 MHz, CDCl₃): δ0.18 (s, 6, Si(CH₃)₂), 0.95 (s, 3, CH₃), 0.97 (s, 9, SiC)CH₃)₃), 1.25–2.3 (m, 13), 2.80 (m, 2), 5.16 (m, 2), 6.10 (dd, J=10.8, 17.1 Hz, 1), 6.54 (d, J=2.5 Hz, 1, ArH), 6.60 (dd, J=2.5, 8.3 Hz, 1, ArH), 7.10 (d, J=8.3 Hz, 1, ArH).

(c) Synthesis of (E)-3-tert-butyldimethylsilyloxy-21-bromo-19-norpregna-1,3,5(10),17(20)-tetraene (4)

To a solution of PBr₃ (0.3 mL, 2.0 mmol) in toluene (5 mL) was added a solution of 3-tert-butyldimethylsilyloxy-19-nor-17α-pregna-1,3,5(10),20-tetraen-17-ol (3, 1.46 g, 3.54 mmol) and pyridine (0.1 mL) in toluene (5 mL) at 0° C. under argon. The resulting mixture was stirred at 0° C. for 1 h, then warmed to room temperature for 1 h. The reaction mixture was quenched by pouring into ice water, then extracted with 40% ethyl acetate/hexane. The organic layer was washed with saturated aqueous NaHCO₃, then with brine, and dried (MgSO₄). The desiccant was filtered, and the solvent was concentrated to afford a gum. Quick filtration through a short plug of silica gel (2% ethyl acetate/hexane) afforded 1.2 g of 4 as a pale yellow gum (71% yield).

¹H NMR (300 MHz, CDCl₃): δ0.18 (s, 6, SiCH₃)₂), 0.81 (s, 3, CH₃), 0.98 (s, 9, SiC(CH₃)₃), 1.20–1.60 (m, 6), 1.80–1.98 (m, 3), 2.16–2.55 (m, 4), 2.82 (m, 2), 4.02 (d, J=8.5 Hz, 2), 5.41 (m, 1), 6.55 (d, J=2.7 Hz, 1, ArH), 6.61 (dd, J=2.7, 8.2 Hz, 1, ArH), 7.12 (d, J=8.2 Hz, 1, ArH).

The following scheme illustrates the synthetic steps carried out in Examples 2 through 5 to make the anti-estrogenic compounds (5), (6), (7) and (8):

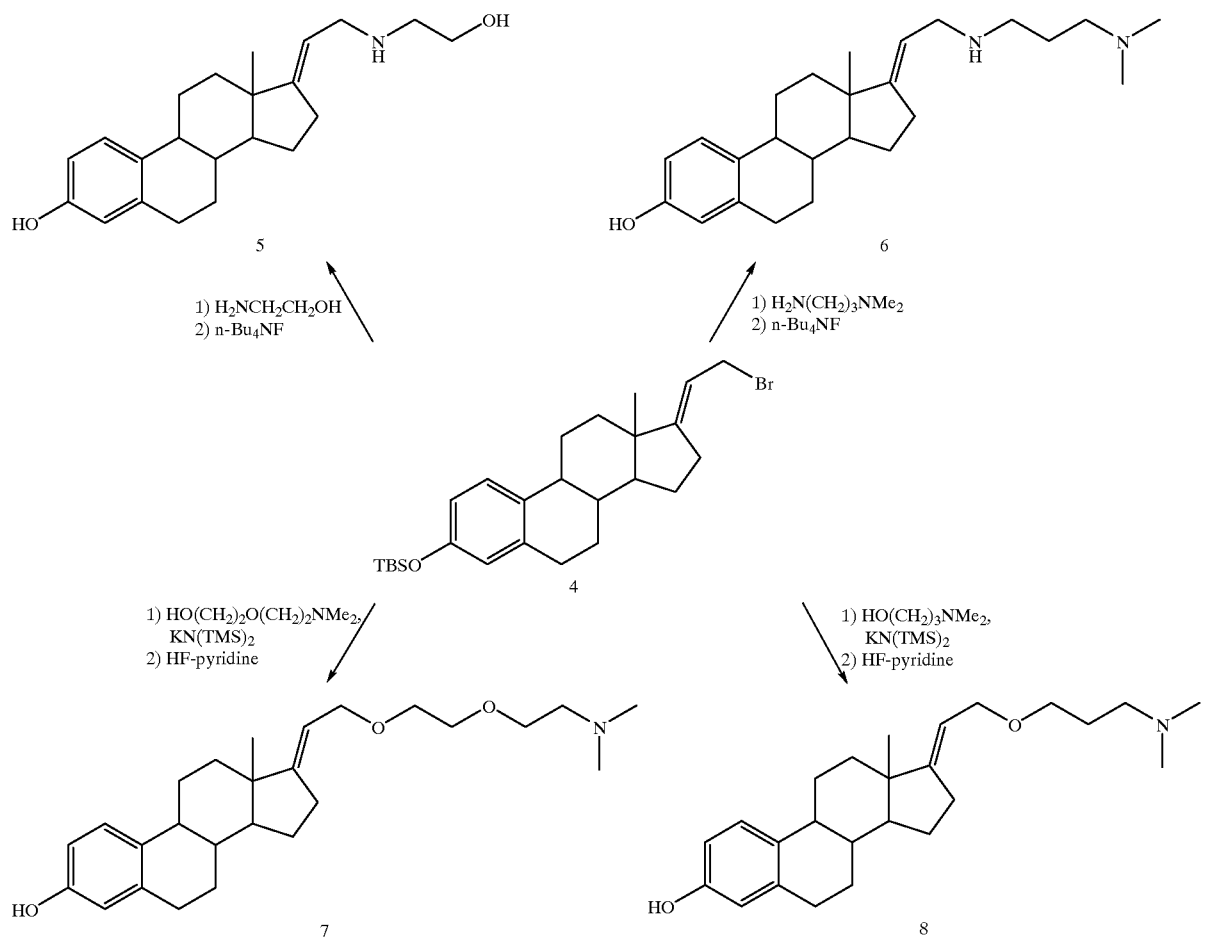

Scheme 2

EXAMPLE 2

Preparation of (E)-3-Hydroxy-21-(2'-hyroxylethylamino)-19-norpregna-1,3,5(10),17(20)-tetraene (5)

To a solution of ethanolamine (0.5 mL, 8.3 mmol) in THF (0.5 mL) at room temperature under argon was added allylic bromide 4 (0.1 g, 0.21 mmol) in THF (1 mL). The reaction mixture was stirred for 20 min., then poured into saturated aqueous NaHCO$_3$ and extracted with 80% ethyl acetate/hexane. The combined organic layers were dried (MgSO$_4$). The desiccant was filtered, and the solvent was concentrated to afford an oil. The crude product was dissolved in THF (3 mL) and a solution of tetrabutylammonium fluoride in THF (0.5 mL, 0.5 mmol) was added at 0° C. and stirred for 30 min. The reaction mixture was poured into saturated aqueous NaHCO$_3$ and extracted with 80% ethyl acetate/hexane. The combined organic layers were dried (MgSO$_4$), the desiccant was filtered, and the solvent was concentrated to afford a gum. Flash chromatography (5% methanol/chloroform) afforded 0.044 g of 5 as a white solid (61% yield), m.p. 203–205° C.

$^1$H NMR (300 MHz, CD$_3$OD): δ0.84 (s, 3, CH$_3$), 2.78 (m, 4), 3.30 (m, 2), 3.69 (t, J=5.5 Hz, 2), 5.17 (m, 1), 6.47 (d, J=2.6 Hz, 1, ArH), 6.53 (dd, J=2.6, 8.5 Hz 1, ArH), 7.07 (d, J=8.5 Hz, 1, ArH). HRMS calcd. for C$_{22}$H$_{31}$NO$_2$ (M$^+$), 341.2355; found, 341.2355.

EXAMPLE 3

Preparation of (E)-3-Hydroxy-21-[3'-(N,N-dimethylamino)-propylamino]-19-norpregna-1,3,5(10),17(20)-tetraene (6)

To a solution of 3-dimethylaminopropylamine (0.5 mL, 4.0 mmol) in THF (0.5 mL) at room temperature under argon was added allylic bromide 4 (0.1 g, 0.21 mmol) in THF (1 mL). The procedure described in Example 2 was used to afford 0.015 g of 6 as a white powder (19% yield).

$^1$H NMR (300 MHz, DMSO-d$_6$): δ0.81 (s, 3, CH$_3$), 2.97 (s, 6, N(CH$_3$)$_2$), 3.85 (m, 2), 5.28 (m, 1), 6.46 (d, J=2.6 Hz, 1, ArH), 6.52 (dd, J=2.6, 8.5 Hz, 1, ArH), 7.08 (d, J=8.5 Hz, 1, ArH).

EXAMPLE 4

Preparation of (E)-3-Hydroxy-21-{2'-[2"-(N,N-dimethylamino)ethoxy]-ethoxy}-19-norpregna-1,3,5(10), 17(20)-tetraene (7)

To a solution of 2-[2-(dimethylamino)ethoxy]ethanol (0.5 g, 3.75 mmol) in THF (8 mL) at room temperature under argon was added a solution of potassium hexamethyldisilazide in toluene (7.0 mL, 3.5 mmol). The resulting solution was stirred for 5 minutes, then a solution of allylic bromide 4 (0.13 g, 0.27 mmol) in THF (1.5 mL) was added. After stirring for 5 min., the reaction mixture was poured into saturated aqueous NaHCO$_3$, and extracted with 80% ethyl acetate/hexane. The combined organic layers were dried (MgSO$_4$). The desiccant was filtered, and the solvent was concentrated to afford an oil. To a solution of the oil in pyridine (1 mL) and CH$_3$CN (2 mL) was added hydrogen fluoride-pyridine (1 mL) at 0° C. The resulting cloudy solution was stirred for 2 h, then poured into water, and extracted with 80% ethyl acetate/hexane. The combined organic layers were dried (MgSO$_4$). The dessicant was filtered, and the solvent was concentrated to afford an oil. Flash chromatography (ethyl acetate; 5% methanol/chloroform) afforded 0.032 g of 7 as a gum (29% yield).

$^1$H NMR (300 MHz, CDCl$_3$): δ0.79 (s, 3, CH$_3$), 1.12–1.56 (m, 6), 1.79–1.98 (m, 3), 2.11–2.40 (m, 4), 2.45 (s, 6, N(CH$_3$)$_2$), 2.74 (t, J=5.6 Hz, 2), 2.83 (m,2), 3.56–3.67 (m, 4), 3.69 (t, J=5.6 Hz, 2), 4.01 (m, 2), 5.22 (m, 1), 6.56 (d, J=2.4 Hz, 1, ArH), 6.63 (dd, J=2.4, 8.7 Hz, 1, ArH), 7.15 (d, J=8.7 Hz, 1, ArH). HRMS calcd. for C$_{26}$H$_{39}$NO$_3$ (M$^+$), 413.2930; found, 413.2930.

EXAMPLE 5

Preparation of (E)-3-Hydroxy-21-[3'-(N,N-dimethylamino)propoxy]-19-norpregna-1,3,5(10),17(20)-tetraene (8)

To a solution of 3-dimethylamino-1-propanol (0.15 mL, 1.27 mmol) in THF (0.5 mL) at room temperature under argon was added allylic bromide 4 (0.1, g 0.21 mmol) in THF (1 mL). The procedure described in Example 2 was used to afford 0.032 g of 8 as a white powder (40% yield), m.p. 159–161° C.

$^1$H NMR (300 MHz, CDCl$_3$): δ0.79 (s, 3, CH$_3$), 2.38 (s, 6, N(CH$_3$)$_2$), 2.58 (m, 2), 2.81 (m, 2), 3.48 (m, 2), 3.95 (m, 2), 5.19 (m, 1), 6.56 (d, J=2.5 Hz, 1, ArH), 6.61 (dd, J=2.5, 8.5 Hz, 1, ArH), 7.14 (d, J=8.5 Hz, 1, ArH. HRMS calcd. for C$_{25}$H$_{37}$NO$_2$ (M$^+$), 383.2824; found, 383.2825.

The following scheme illustrates the synthetic steps carried out in Examples 6 through 9 to make the anti-estrogenic compounds (9), (10), (11) and (12):

Scheme 3

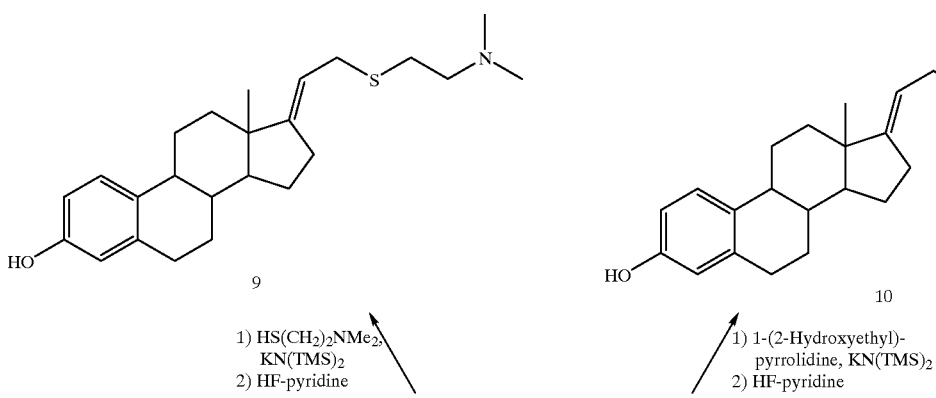

-continued

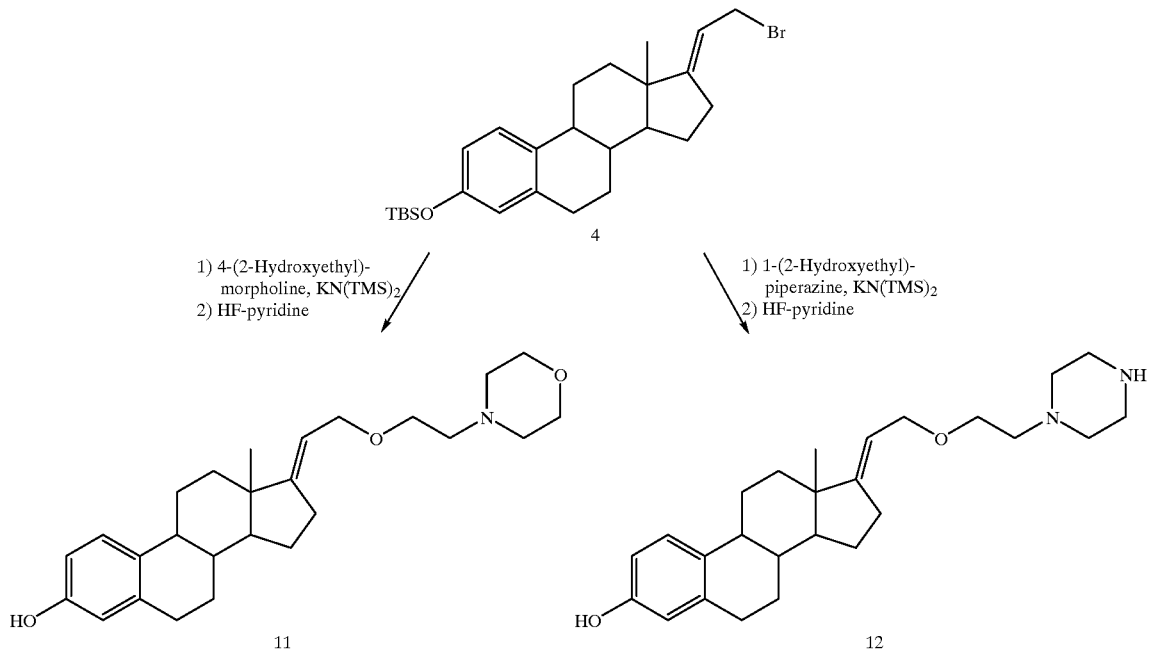

EXAMPLE 6

Preparation of (E)-3-Hydroxy-21-[2'-(N,N-dimethylamino)-ethanethio]-19-norpregna-1,3,5(10),17(20-tetraene (9)

To a suspension of 2-dimethylaminoethanethiol-HCl (86 mg, 0.6 mmol) in THF (3 mL) at −78° C. under argon was added a solution of n-butyllithium in hexane (0.7 mL, 1.1 mmol). The resulting mixture was warmed to room temperature until the white solid had dissolved to form a light yellow solution, and the solution was then cooled to −78° C. To the cooled solution was added allylic bromide 4 (0.1 g, 0.21 mmol) in THF (1.5 mL). After warming the reaction mixture to room temperature, and stirring for 10 min., the mixture was poured into saturated aqueous $NaHCO_3$, and extracted with 80% ethyl acetate/hexane. The combined organic layers were dried ($MgSO_4$), the desiccant was filtered, and the solvent was concentrated to afford an oil. The oil was dissolved in $CH_3CN$ (2 mL) and pyridine (1 mL). HF-pyridine (1 mL) was added at 0° C., the solution was stirred for 2 h, and was then extracted with 80% ethyl acetate/hexane. The combined organic layers were dried ($MgSO_4$), the desiccant was filtered, and the solvent was concentrated to afford a gum. Flash chromatography (ethyl acetate; 5% methanol/chloroform) afforded 0.065 g of 9 as a white solid (80% yield), m.p. 138–140° C.

$^1$H NMR (300 MHz, $CDCl_3$): δ0.74 (s, 3, $CH_3$), 1.01–1.55 (m, 6), 1.75–2.01 (m, 4), 2.32 (s, 6, $N(CH_3)_2$), 2.61 (m, 4), 2.79 (m, 2), 3.31 (m, 2), 5.09 (m, 1), 6.52 (d, J=2.7 Hz, 1, ArH), 6.56 (dd, J=2.7, 8.3 Hz, 1, ArH), 7.09 (d,J=8.3 Hz, 1, ArH). HRMS calcd. for $C_{24}H_{35}NOS$ ($M^+$), 385.2439; found, 385.2436.

EXAMPLE 7

Preparation of (E)-3-Hydroxy-21-[2'-(pyrrolidinyl) thoxy]-19-norpregna-1,3,5(10),17(20)-tetraene (10)

To a solution of 1-(2-hydroxyethyl)-pyrrolidine (0.15 mL, 1.3 mmol) in THF (2 mL) at 0° C. under argon was added a solution of potassium hexamethyldisilazide in toluene (2.0 mL, 1.0 mmol). After stirring for 5 min., the reaction mixture was cooled to −78° C., and a solution of allylic bromide 4 (0.1 g, 0.21 mmol) in THF (2 mL) was added. After warming the reaction mixture to 0° C. for 20 min., the mixture was poured into saturated aqueous $NaHCO_3$, and extracted with 80% ethyl acetate/hexane. The combined organic layers were dried ($MgSO_4$), the desiccant was filtered, and the solvent was concentrated to afford a gum. The gum was dissolved in $CH_3CN$ (2 mL) and pyridine (1 mL). HF-pyridine (1.0 mL) was added at 0° C., the solution was stirred for 2 h and was then poured into water and extracted with 80% ethyl acetate/hexane. The combined organic layers were dried ($MgSO_4$), the dessicant was filtered, and the solvent was concentrated to afford an oil. Flash chromatography (ethyl acetate; 5% methanol/ chloroform) afforded 0.039 g of 10 as a white solid (47% yield), m.p. 149–152° C.

$^1$H NMR (300 MHz, $CDCl_3$): δ0.77 (s, 3, $CH_3$), 1.12 (m, 1), 1.22–158 (m, 5), 1.75–1.94 (m, 7), 2.11 (m, 1), 2.33 (m, 3), 2.72–2.90 (m, 8), 3.65 (m, 2), 3.99 (m, 2), 5.19 (m, 1), 6.54 (d, J=2.3 Hz, 1, ArH), 6.60 (dd, J=2.3, 8.0 Hz, 1, ArH), 7.13 (d, J=8.0 Hz, 1, ArH). HRMS calcd. for $C_{26}H_{37}NO_2$ ($M^+$), 395.2824; found, 395.2823.

EXAMPLE 8

Preparation of (E)-3-Hydroxy-21-[2'-(morpholinyl) ethoxy]-19-norpregna-1,3,5(10),17(20)-tetraene (11)

To a solution of 4-(2-hydroxyethyl)morpholine (0.15 mL, 1.2 mmol) in THF (0.5 mL) at room temp under argon was added allylic bromide 4 (0.1 g, 0.21 mmol) in THF (1 mL). The procedure described in Example 7 was used to afford 0.062 g of 11 as a white powder (72% yield), m.p. 140–142° C.

$^1$H NMR (300 MHz, $CDCl_3$): δ0.79 (s, 3, $CH_3$), 1.18 (m, 1), 1.28–1.60 (m, 5), 1.77–1.98 (m, 3), 2.15 (m, 1), 2.35 (m, 3), 2.53 (m, 4), 2.62 (t, J=5.8 Hz, 2), 2.82 (m, 2), 3.57 (m, 2), 3.74 (m, 4), 3.99 (m, 2), 5.21 (m, 1), 6.55 (d, J=2.6 Hz,

1, ArH), 6.61 (dd, J=2.6, 8.8 Hz, 1, ArH), 7.15 (d, J=8.8 Hz, 1, ArH). HRMS calcd. for $C_{26}H_{37}NO_3$ (M+), 411.2773; found, 411.2774.

EXAMPLE 9

Preparation of (E)-3-Hydroxy-21-[2'-(piperazinyl)ethoxy]-19-norpregna-1,3,5(10),17(20)-tetraene (12)

To a solution of 1-(2-hydroxyethyl)piperazine (0.15 mL, 1.22 mmol) in THF (0.5 mL) at room temperature under argon was added allylic bromide 4 (0.1 g, 0.21 mmol) in THF (1 mL). The procedure described in Example 7 was used to afford 0.031 g of 12 as a white powder (36% yield), m.p. 198–200° C.

$^1$H NMR (300 MHz $CDCl_3$): δ0.79 (s, 3, $CH_3$), 1.15 (m, 1), 1.22–1.60 (m, 5), 1.75–1.98 (m, 3), 2.16 (m, 1), 2.32 (m, 3), 2.48–2.70 (m, 10), 2.81 (m, 2), 3.01 (m, 2), 3.64 (m, 2), 5.17 (m, 1), 6.54 (d,J=2.3 Hz, 1, ArH), 6.61 (dd, J=2.3, 8.0 Hz, 1, ArH), 7.13 (d,J=8.0 Hz, 1, ArH). HRMS calcd. for $C_{26}H_{38}N_2O_2$ (M+), 410.2933; found, 410.2928.

The following scheme illustrates the synthetic steps carried out in Examples 10 through 14 to make the anti-estrogenic compounds (21), (22), (23), (24), (25) and (27):

Scheme 4

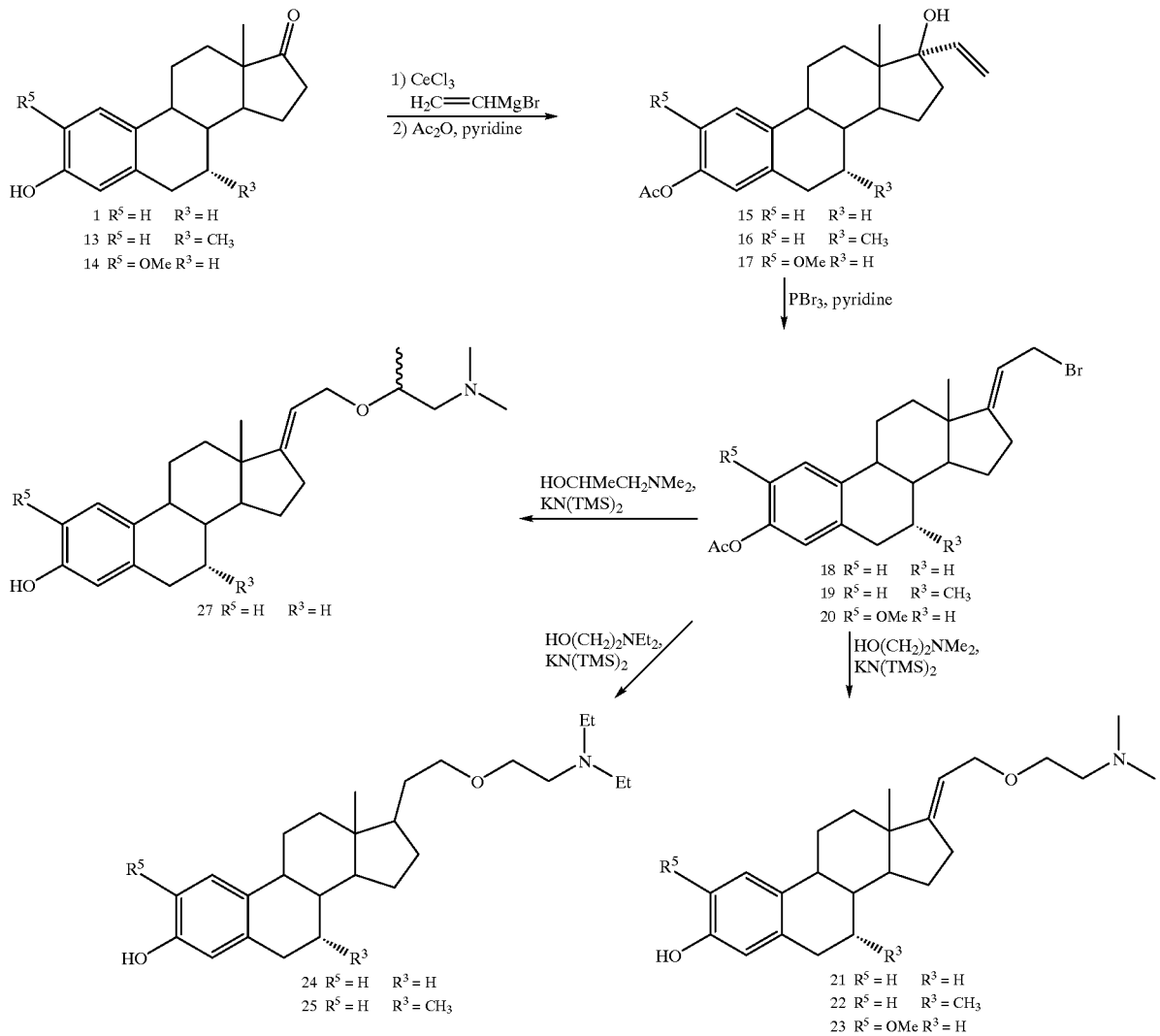

EXAMPLE 10

Preparation of (E)-3-Hydroxy-21-[2'(N,N-dimethylamino)ethoxy]-19-norpregna-1,3,5(10),17(20)-tetraene (21)

(a) Synthesis of 3-acetoxy-19-nor-17α-pregna-1,3,5(10),20-tetraen-17-ol (15)

A mixture of estrone 1 (10.0 g, 37 mmol) and $CeCl_3$ (18.2 g, 74 mmol) in THF (400 mL) at room temperature under argon was stirred for 16 h. To this mixture was added a solution of vinylmagnesium bromide in THF (160 mL, 160 mmol). After stirring at room temperature for 30 min., the reaction mixture was quenched by pouring into saturated aqueous $NaHCO_3$, and extracted with 80% ethyl acetate/hexane. The combined organic layers were dried ($MgSO_4$), the desiccant was filtered and the solvent was concentrated to afford 3-hydroxy-19-nor-17α-pregna-1,3,5(10),20-tetraen-17-ol as a solid.

$^1$H NMR (300 MHz, $CDCl_3$): δ0.93 (s, 3, $CH_3$), 2.80 (m, 2), 5.20 (m, 2), 6.09 (dd, J=10.7, 17.3 Hz, 1), 6.54 (d, J=2.6 Hz, 1, ArH), 6.60 (dd, J=2.6, 8.5 Hz, 1, ArH), 7.10 (d, J=8.5 Hz 1, ArH).

To a solution of 3-hydroxy-19-nor-17α-pregna-1,3,5(10),20-tetraen-17-ol in THF (150 mL) were added pyridine (10 mL) and $Ac_2O$ (5 mL) at room temperature under argon. The resulting mixture was stirred at room temperature for 5 h, then diluted with 80% ethyl acetatelhexane and washed with aqueous HCl, $NaHCO_3$ and brine. The organic layer was dried ($MgSO_4$), the desiccant was filtered and the solvent was concentrated to afford a solid. Flash chromatography (15% ethyl acetate/hexane) afforded 11.7 g of 15 as a white solid (93% yield).

$^1$H NMR (300 MHz, $CDCl_3$): δ0.95 (s, 3, $CH_3$), 2.28 (s, 3, OAc), 2.86 (m, 2), 5.18 (m, 2), 6.11 (dd, J=10.7, 17.3 Hz, 1), 6.79 (d, J=2.3 Hz, 1, ArH), 6.83 (dd, J=2.3, 8.3 Hz, 1, ArH), 7.27 (d, J=8.3 Hz, 1, ArH).

(b) Synthesis of (E)-3-Acetoxy-21-bromo-19-norpregna-1,3,5(10),17(20)-tetraene (18)

To a solution of $PBr_3$ in $CH_2Cl_2$ (0.7 mg, 0.7 mmol) and toluene (5 mL) was added a mixture of 3-acetoxy-19-nor-17α-pregna-1,3,5(10),20-tetraen-17-ol (15) (0.25 g 0.73 mmol) and pyridine (0.06 mL, 0.74 mmol) in toluene (3 mL). The resulting mixture was stirred at 0° C. for 1.5 h, then quenched by pouring into cold water, and extracted with 40% ethyl acetate/hexane. The organic layer was washed with saturated aqueous $NaHCO_3$ and brine, and was dried ($MgSO_4$). The desiccant was filtered and the solvent was concentrated to afford a white solid. Quick filtration through a plug of silica gel in 10% ethyl acetate/hexane yielded 0.25 g of 18 as a white solid (85% yield), m.p. 142–145° C.

$^1$H NMR (300 MHz, $CDCl_3$): δ0.81 (s, 3, $CH_3$), 2.29 (s, 3, $COCH_3$), 2.88 (m, 2), 4.02 (d, J=8.5 Hz, 2), 5.43 (m, 1), 6.80 (d,J=2.3 Hz, 1, ArH), 6.85 (dd, J=2.3, 8.3 Hz, 1, ArH), 7.30 (d, J=8.3 Hz, 1, ArH). HRMS calcd. for $C_{22}H_{27}BrO_2$ ($M^+$), 402.1195; found, 402.1203.

(c) Synthesis of (E)-3-Hydroxy-21-[2'-(N,N-dimethylamino)ethoxy]-19-norpregna-1,3,5(10),17(20)-tetraene (21)

To a solution of N,N-dimethylethanolamine (0.6 mL, 6.0 mmol) in THF (8 mL) at 0° C. under argon was added potassium hexamethyldisilazide in toluene (11.5 mL, 5.75 mmol). The solution was stirred for 5 min., then cooled to −78° C. (E)-3-acetoxy-21-bromo-19-norpregna-1,3,5(10),17(20)-tetraene (18) (0.2 g, 0.5 mmol) in THF (3 mL) was added, and the reaction mixture was warmed to 0° C. for 30 min. The resulting yellow cloudy solution was poured into saturated aqueous $NaHCO_3$ and extracted with 80% ethyl acetate/hexane. The combined organic layers were dried ($MgSO_4$), the desiccant was filtered, and the solvent was concentrated to afford an oil. Flash chromatography (5% methanol/chloroform) afforded 0.11 g of 21 as a white solid (60% yield), m.p. 123–124° C.

$^1$H NMR (300 MHz, $CDCl_3$): δ0.75 (s, 3, $CH_3$), 1.04 (m, 1), 1.20–1.56 (m, 5), 1.72–1.92 (m, 3), 2.04 (m, 1), 2.30 (m, 3), 2.33 (s, 6, $N(CH_3)_2$), 2.60 (t, J=5.7, Hz, 2), 2.80 (m, 2), 3.56 (m, 2), 3.98 (m, 2), 5.19 (m, 1), 6.53 (d, J=2.7 Hz, 1, ArH), 6.58 (dd, J=2.7, 8.3 Hz, 1, ArH), 7.11 (d, J=8.3 Hz, 1, ArH). Anal. calcd. for $C_{24}H_{35}NO_2$: C, 78.0; H, 9.55; N, 3.79; found: C, 77.9; H, 9.50; S, 3.80. HRMS calcd. for $C_{24}H_{35}NO_2(M^+)$, 369.2667; found, 369.2666.

EXAMPLE 11

Preparation of (E)-3-Hydroxy-7α-methyl-21-[2'-(N,N-dimethylamino)ethoxy]-19-norpregna-1,3,5(10),17(20)-tetraene (22)

(a) Synthesis of(E)-3-acetoxy-7α-methyl-21-bromo-19-norpregna-1,3,5(10),17(20)-tetraene (19)

By the procedure described in Example 10, step (a), with 7α-methyl estrone (13), 0.93 g, 3.27 mmol) substituted for estrone, 3-hydroxy-7α-methyl-19-nor-17α-pregna-1,3,5(10),20-tetraen-17-ol was obtained as an oil.

$^1$H NMR (300 MHz, $CDCl_3$): δ0.82 (d,J=7.0 Hz, 3, $CH_3$), 0.95 (s, 3, $CH_3$), 2.50 (d, J=17.0 Hz, 1), 3.04 (dd, J=6.6, 17.0 Hz, 1), 5.19 (m, 2), 6.12 (dd, J=10.7, 17.3 Hz, 1), 6.54 (d, J=2.5 Hz, 1, ArH), 6.61 (dd, J=2.5, 8.5 Hz, 1, ArH), 7.14 (d, J=8.5 Hz, 1, ArH).

3-Hydroxy-7α-methyl-19-nor-17α-pregna-1,3,5(10),20-tetraen-17-ol was acetoxylated as described in Example 10, step (a) to afford 16 (pale yellow form).

$^1$H NMR (300 MHz, $CDCl_3$): δ0.83 (d, J=7.1 Hz, 3, $CH_3$), 0.95 (s, 3, $CH_3$), 2.27 (s, 3, $COCH_3$), 2.55 (d, J=17.0 Hz, 1), 3.09 (dd, J=6.7, 17.0 Hz, 1), 5.18 (m, 2), 6.12 (dd, J=10.7, 17.3 Hz, 1), 6.77 (d, J=2.5 Hz, 1, ArH), 6.83 (dd, J=2.5, 8.5 Hz, 1, ArH), 7.27 (d, J=8.5 Hz, 1, ArH).

By the procedure described in Example 10, step (b), 0.98 g of(E)-3-acetoxy-7α-methyl-21-bromo-19-norpregna-1,3,5 (10), 17(20)-tetraene (19) was obtained from 16 as a gum (72% yield).

$^1$H NMR (300 MHz, $CDCl_3$): δ0.81 (s, 3, $CH_3$), 0.85 (d, J=7.1 Hz, 3, $CH_3$), 2.27 (s, 3, $COCH_3$), 2.57 (d, J=16.8 Hz, 1), 3.10 (dd, J=6.6, 16.8 Hz, 1), 4.02 (d, J=8.5 Hz, 2), 5.42 (m, 1), 6.78 (d, J=2.3 Hz, 1, ArH), 6.84 (dd, J=2.3, 8.8 Hz, 1, ArH), 7.29 (d, J=8.8 Hz, 1, ArH).

(b) Synthesis of (E)-3-Hydroxy-7α-methyl-21-[2'-(N,N-dimethylamino)ethoxy]-19-norpregna-1,3,5(10),17(20)-tetraene (22)

By the procedure described in Example 10, step (c), 0.11 g of 22 was obtained as a white solid (60% yield), m.p. 129–132° C.

$^1$H NMR (300 MHz, $CDCl_3$): δ0.78 (s, 3, $CH_3$), 0.81 (d, J=7.2 Hz, 3, $CH_3$), 2.32 (s, 6, $N(CH_3)_2$), 2.50 (d, J=16.8 Hz, 2), 2.59 (t, J=5.7 Hz, 2), 3.04 (dd, J=6.6, 16.8 Hz, 1), 3.56 (m, 2), 3.99 (m, 2), 5.22 (m, 1), 6.53 (d, J=2.5 Hz, 1, ArH), 6.61 (dd, J=2.5, 8.4 Hz, 1, ArH), 7.15 (d, J=8.4Hz, 1, ArH).

EXAMPLE 12

Preparation of (E)-3-hydroxy-2-methoxy-21-[2'-(N,N-dimethylamino)ethoxy]-19-norprega-1,3,5(10)-17(20)-tetraene (23)

(a) Synthesis of 3-acetoxy-2-methoxy-19-nor-17α-pregna-1,3,5(10),20-tetraen-17-ol (20)

By the procedure described in Example 10, step (a), with 2-methoxyestrone (14), 0.6 g, 2.0 mmol) substituted for estrone, 3-hydroxy-2-methoxy-19-nor-17α-pregna-1,3,5 (10),20-tetraen-17-ol, was obtained as an oil.

¹H NMR (300 MHz, CDCl₃): δ0.95 (s, 3, CH₃), 3.84 (s, 3, OCH₃), 5.17 (m, 2), 6.10 (dd, J=10.8, 17.4 Hz, 1), 6.63 (s, 1, ArH), 6.77 (s, 1, ArH).

3-Hydroxy-2-methoxy-19-nor-17α-pregna-1,3,5(10),20-tetraen-17-ol was acetoxylated as described in Example 10, step (a) to afford 17 as a gum.

¹H NMR (300 MHz, CDCl₃): δ0.96 (s, 3, CH₃), 2.30 (s, 3, OAc), 3.80 (s, 3, OCH₃), 5.18 (m, 2), 6.11 (dd, J=10.7, 17.3 Hz, 1), 6.73 (s, 1, ArH), 6.88 (s, 1, ArH).

By the procedure described in Example 10, step (b), 0.3 g of 20 was obtained from 17 as a gum (35% yield).

¹H NMR (300 MHz, CDCl₃): δ1.00 (s, 3, CH₃), 2.29 (s, 3, COCH₃), 3.80 (s, 3, OCH₃), 5.30 (m, 2), 6.14 (m, 1), 6.73 (s, 1, ArH), 6.86 (s, 1, ArH).

(b) Preparation of (E)-3-hydroxy-2-methoxy-21-[2'-(N,N-dimethylamino)ethoxy]-19-norpregna-1,3,5(10),17(20)-tetraene (23)

By the procedure described in Example 10, step (c), 0.15 g of 23 was obtained as a white solid (54% yield), m.p. 94–95° C.

¹H NMR (300 MHz, CDCl₃): δ0.81 (s, 3, CH₃), 2.29 (s, 6, N(CH₃)₂), 2.53 (t, J=5.8 Hz, 2), 2.77 (m, 2), 3.53 (t, J=5.8 Hz, 2), 3.86 (s, 3, OCH₃), 4.00 (m, 2), 5.24 (m,1), 6.64 (s, 1, ArH), 6.80 (s, 1, ArH). HRMS calcd. for C₂₅H₃₇NO₃(M⁺), 399.2773; found, 399.2771.

EXAMPLE 13

Preparation of (E)-3-Hydroxy-21-[2'-(N,N-diethylamino)ethoxy]-19-norpregna-1,3,5(10),17(20)-tetraene (24)

The amine 24, which was prepared from allylic bromide 18 (0.11 g, 0.26 mmol) and N,N-dimethylethanolamine (0.2 mL, 1.5 mmol) using the same prodedure as described for amine 21, was obtained as a white solid (0.074 g, 72%): ¹H NMR (300 MHz, CDCl₃) δ0.78 (s, 3, CH3), 1.24 (t, J=7.1 Hz, 6, N(CH₂CH)₂), 2.78 (m, 2) 3.00 (m,6), 3.70 (m, 2), 3.96 (m, 2), 5.14 (m, 1), 6.54 (d, J=2.5 Hz, 1, ArH), 6.60 (dd, J=2.5, 8.5 Hz, 1, ArH), 7.11 (d, J=8.5 Hz, 1, ArH). HRMS for C₂₅H₃₇NO₂ (M⁺) calcd. 397.2981 found 397.2985.

EXAMPLE 14

Preparation of (E)-3-Hydroxy-21-[2'(N,N-dimethylamino)-2-propoxy]-19-norpregna-1,3,5(10),17(20)-tetraene (27)

By the procedure of described in Example 10, step (c), (E)-3-acetoxy-21-bromo-19-norpregna-1,3,5(10),17(20)-tetraene (18, 0.15 g, 0.37 mmol) was reacted with 1-dimethylamino-2-propanol (0.3 mL, 2.4 mmol) to afford 0.075 g of a 1:1 diastereomeric mixture of 27 as a white powder (53% yield).

(diastereomer A) ¹H NMR (300 MHz, CDCl₃): δ0.75 (s, 3, CH₃), 1.17 (d, J=6.2 Hz, 3, CH₃), 2.33 (s, 6, N(CH₃)₂), 2.79 (m, 2), 3.68 (m, 1), 4.01 (m, 2), 5.20 (m, 1), 6.54 (d, J=3.0 Hz, 1, ArH), 6.60 (dd, J=3.0, 8.3 Hz, 1, ArH), 7.10 (d,J=8.3 Hz, 1, ArH);

(diastereomer B) ¹H NMR (300 MHz, CDCl₃): δ0.75 (s, 3, CH₃), 1.18 (d,J=6.2 Hz, 3, CH₃), 2.33 (s, 6, N(CH₃)₂), 2.79 (m, 2), 3.68 (m, 1), 3.90 (dd,J=5.6, 11.5 Hz, 1), 4.12 (dd,J=7.7, 11.5 Hz, 1), 5.20 (m, 1), 6.54 (d, J=3.0 Hz, 1, ArH), 6.61 (dd, J=3.0, 8.3 Hz, 1, ArH), 7.12 (d, J=8.3 Hz, 1, ArH).

EXAMPLE 15

Preparation of (Z)-3-Hydroxy-21-[2'-(N,N-dimethylamino)ethoxy]-19-norpregna-1,3,5(10),17(20)-tetraene (32)

Scheme 5

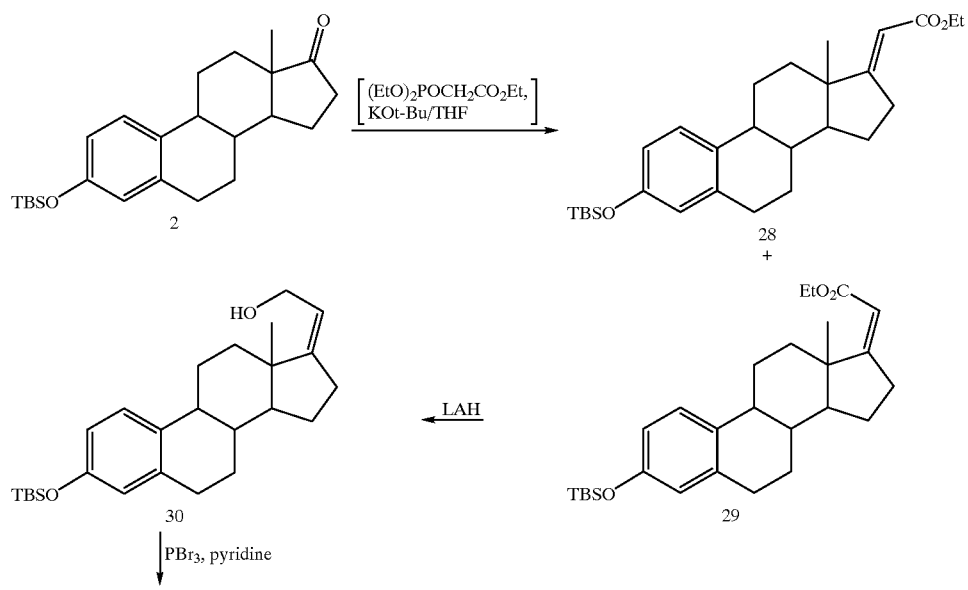

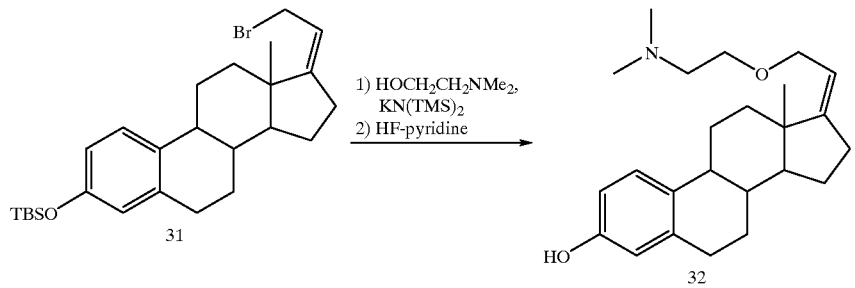

(a) Preparation of ethyl (E)- and (Z)-3-tert-butyldimethylsilyloxy-19-norpregna-1,3,5(10),17(20)-tetraen-21-oate (28) and (29)

To a solution of triethyl phosphonoacetate (2.24 g, 10.1 mmol) in THF (30 mL) under argon at room temperature was added a potassium t-butoxide in THF (9.1 mL, 9.1 mmol). After stirring for 1.0 h, 3-tert-butyl dimethylsilyloxy estrone (2, 1.75 g, 4.55 mmol) in THF (10 mL) was added, and the solution was heated to reflux overnight. The reaction mixture was poured into saturated aqueous NaHCO$_3$ and extracted with 40% ethyl acetate/hexane. The combined organic layers were dried (MgSO$_4$), the desiccant was filtered, and the solvent was concentrated to afford the mixture of E and Z isomers, 28 and 29, as a yellow solid. Chromatography (hexane; 2.5% EtOAc) afforded 1.4 g of the E isomer 28 (68% yield), and 0.2 g of the Z isomer 29 (10% yield).

(28): m.p. 109–110° C.; R$_f$ 0.56 (10% EtOAc/hexane): $^1$H NMR (300 MHz, CDCl$_3$): δ0.19 (s, 6, Si(CH$_3$)$_2$), 0.86 (s, 3, CH$_3$), 0.98 (s, 9, SiC(CH$_3$)$_3$), 1.29 (t, J=7.1 Hz, 3, CO$_2$CH$_2$CH$_3$), 4.16 (q, J=7.1 Hz, 2, CO$_2$CH$_2$CH$_3$), 5.59 (t, J=2.4 Hz 1), 6.56 (d, J=2.6 Hz, 1, ArH), 6.61 (dd, J=2.6, 8.3 Hz, 1, ArH), 7.12 (d, J=8.3 Hz, 1, ArH).

(29): m.p. 154–156° C.; R$_f$ 0.5 (10% EtOAc/hexane): $^1$H NMR (300 MHz, CDCl$_3$): δ0.18 (s, 6, Si(CH$_3$)$_2$), 0.98 (s, 9, SiC(CH$_3$)$_3$), 1.04 (s, 3, CH$_3$), 1.29 (t,J=7.1 Hz, 3,CO$_2$CH$_2$CH$_3$), 4.14 (q, J=7.1 Hz, 2, CO$_2$CH$_2$CH$_3$), 5.68 (t, J=2.0 Hz, 1), 6.55 (d, J=2.0 Hz 1, ArH), 6.61 (dd, J=2.0, 8.6 Hz, 1, ArH), 7.12 (d, J=8.6 Hz, 1, ArH).

(b) Preparation of (Z)-3-tert-butyldimethylsilyloxy-21-hydroxy-19-norpregna-1,3,5(10),17(20)-tetraene (30)

To a solution of (Z)-3-tert-butyldimethylsilyloxy-19-norpregna-1,3,5(10),17(20)-tetraen-21-oate (29, 0.1 g, 0.22 mmol) in THF (5 mL) was added lithium aluminum hydride (0.015 g, 0.4 mmol) at 0° C. After stirring for 1 h under argon, the reaction mixture was quenched with water. The white precipitate was removed by filtration and washed several times with 80% EtOAc/hexane. The filtrate was dried (MgSO$_4$), the desiccant was filtered, and the solvent was concentrated to afford 30 as a solid.

$^1$H NMR (300 MHz, CDCl$_3$): δ0.18 (s, 6, Si(CH$_3$)$_2$), 0.93 (s, 3, CH$_3$), 0.98 (s, 9, SiC(CH$_3$)$_3$), 4.20 (m, 1), 4.34 (m, 1), 5.35 (m, 1), 6.55 (d, J=2.7 Hz, 1, ArH), 6.61 (dd, J=2.7, 8.3 Hz, 1, ArH), 7.11 (d, J=8.3 Hz 1, ArH).

(c) Preparation of (Z)-3-tert-butyldimethylsilyloxy-21-bromide-19-norpregna-1,3,5(10,17(20)-tetraene (31)

To a solution of (Z)-3-tert-butyldimethylsilyloxy-21-hydroxy-19-norpregna-1,3,5(10),17(20)-tetraene (30) in toluene (10 mL) was added pyridine (0.04 mL, 0.49 mmol) and PBr$_3$ in CH$_2$Cl$_2$ (0.24 mL, 0.24 mmol) at −78° C. under argon. After stirring for 2 h, the reaction mixture was quenched by pouring into ice water, and extracted with 40% ethyl acetate/hexane. The organic layer was washed with saturated aqueous NaHCO$_3$ and with brine, and dried (MgSO$_4$). The desiccant was filtered and the solvent was concentrated to afford 31 as a gum.

$^1$H NMR (300 MHz, CDCl$_3$): δ0.18 (s, 6, Si(CH$_3$)$_2$), 0.85 (s, 3, CH$_3$), 0.98 (s, 9, SiC(CH$_3$)$_3$), 4.19 (m, 2), 5.48 (m, 1), 6.55 (d, J=2.5 Hz, 1, ArH), 6.61 (dd, J=2.5, 8.5 Hz, 1, ArH), 7.12 (d, J=8.5 Hz 1, ArH).

(d) Preparation of (Z)-3-Hydroxy-21-[2'-(N,N-dimethylamino)ethoxy]-19-norpregna-1,3,5(10),17(20)-tetraene (32)

To a solution of N,N-dimethylethanolamine (0.15 mL, 1.3 mmol) in THF (2 ml) at 0° C. under argon was added potassium hexamethyldisilazide in toluene (2.0 mL, 1.0 mmol). After stirring for 5 min., the reaction mixture was cooled to −78° C. and (Z)-3-tert-butyldimethylsilyloxy-21-bromide-19-norpregna-1,3,5(10,17(20)-tetraene (31, 0.1 g, 0.21 mmol) in THF (2 mL) was added. The solution was warmed to 0° C. for 20 min., then poured into saturated aqueous NaHCO$_3$ and extracted with 80% ethyl acetate/hexane. The combined organic layers were dried (MgSO$_4$), the desiccant was filtered and the solvent was concentrated to afford a gum. To a solution of the gum in CH$_3$CN (2 mL) and pyridine (1 mL) was added HF-pyridine (1.0 mL) at 0° C. After stirring for 2 h, the cloudy solution was poured into water and extracted with 80% ethyl acetate/hexane. The combined organic layers were dried (MgSO$_4$), the desiccant was filtered and the solvent was concentrated to afford an oil. Flash chromatography (ethyl acetate; 5% methanol/chloroform) afforded a white solid. Recrystallization (CH$_2$Cl$_2$) 0.023 g of 32 as white solid (28% yield from 29).

$^1$H NMR (300 MHz, CDCl$_3$): δ0.88 (s, 3, CH$_3$), 2.38 (s, 6, N(CH$_3$)$_2$), 2.66 (t, J=5.8 Hz, 2), 2.79 (m, 2), 3.58 (t, J=5.8 Hz, 2), 4.06 (m, 1), 4.17 (m, 1), 5.22 (m, 1), 6.53 (d, J=2.4 Hz, 1, ArH), 6.59 (dd, J=2.4, 8,2 Hz 1, ArH), 7.09 (d, J=8.2 Hz, 1, ArH).

The following scheme illustrates preparation of compounds (33) and (34) as described in Examples 16 and 17:

Scheme 6

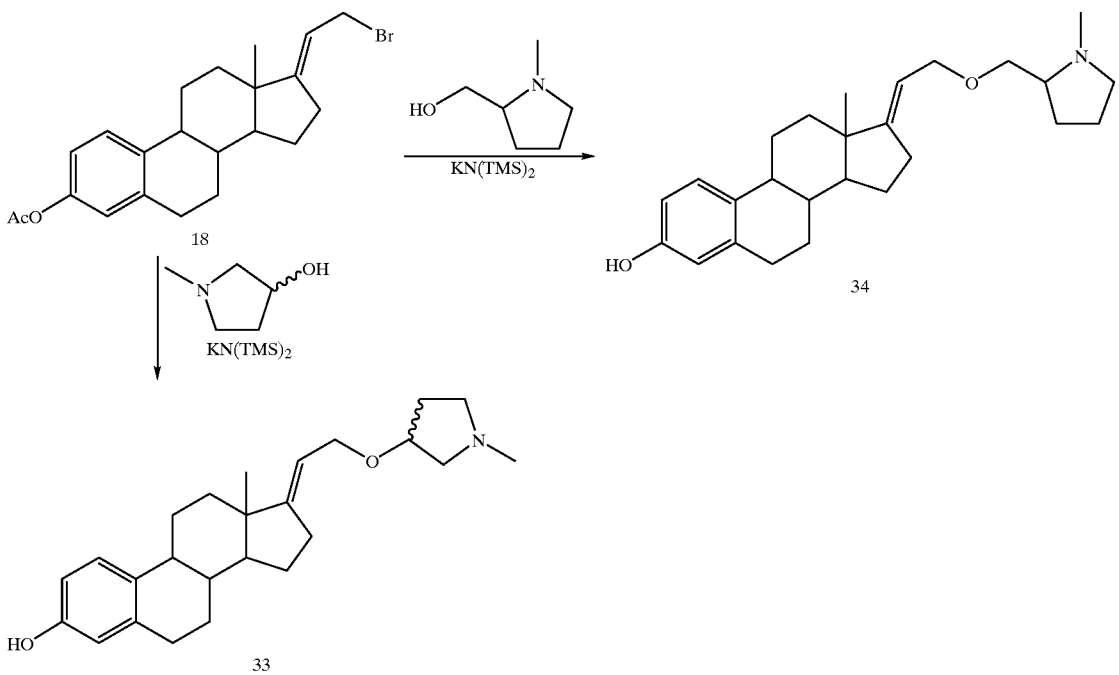

EXAMPLE 16

Preparation of (E)-3-Hydroxy-21-N-methyl-3-(R,S)-pyrrolidinoxy)-19-norpregna-1,3,5(10),17(20)-tetraene (33)

To a solution of 1-methyl-3-pyrrolidinol (500 μL, 4.55 mmol) in dry THF (6 mL) at 0° C. under argon was added a 0.5 M solution of potassium bis(trimethylsilyl)-amide in toluene (8.3 mL, 4.15 mmol), and stirred for 5 min. The solution was cooled to −78° C. and a solution of the allylic bromide, (E)-3-acetoxy-21-bromo-19-norpregna-1,3,5(10),17(20)-tetraene (18, 333 mg, 823 μmol) in dry THF (5 mL) was added, and the reaction mixture was warmed to 0° C. for 30 min. The cloudy yellow solution was poured into saturated aqueous $NaHCO_3$ and extracted with ethyl acetate. The organic layer was dried ($Na_2SO_4$) and evaporated to an oil. Flash chromatography (5–10% methanol/dichloromethane) yielded the desired amine 33 as an off-white foam, 0.025 g (7.9%).

$^1$H NMR (300 MHz, $CDCl_3$): δ0.73 (s, 3, $CH_3$), 1.10–1.54 (m, 7), 1.72 –2.38 (m, 8), 2.56 (s, 3, $NCH_3$), 2.67–2.91 (m, 4), 3.02 (m, 1), 3.21 (m, 1), 3.7 (br s, 1), 3.89 (m, 2), 4.12 (m, 1), 5.11 (m, 1), 6.49 (d, J=2.6 Hz, 1, ArH), 6.57 (dd, J=2.6, 8.3 Hz, 1, ArH), 7.04(d, J=8.3 Hz, 1, ArH).

EXAMPLE 17

Preparation of (E)-3-Hydroxy-21-[N-methyl-2(S)-pyrrolidinylmethoxy]-19-norpregna-1,3,5(10),17(20)-tetraene (34)

The amine 34 was prepared from the allylic bromide (E)-3-acetoxy-21-bromo-19norpregna-1,3,5(10),17(20)-tetraene (0.2 g, 496 μmol) and (S)-1-methyl-2-pyrrolidinemethanol (314 mg, 2.73 mmol) using the same procedure as described in Example 16 for the preparation of amine 33 to give a white solid (0.070 g 36%): m.p. 175–177° C.

$^1$H NMR (300 MHz, $CDCl_3$): δ0.72 (s, 3, $CH_3$), 1.07–1.98 (m, 13), 2.05–2.45 (m, 9, includes s, 2.35, $NCH_3$), 276 (m, 2), 2.97 (m, 1), 3.30 (dd, J-6, 8 Hz), 3.43 (dd, J-6, 12 Hz), 3.6 (br s, 1), 3.91 (m, 2), 5.12 (m, 1), 6.48 (d, J=2.6 Hz, 1, ArH), 6.52 (dd, J-2.6, 8.3 Hz, 1, ArH), 7.05 (d,J=8.3 Hz, 1, ArH.

The following scheme illustrates preparation of compounds (35) and (36) as described in Examples 18 and 19:

Scheme 7

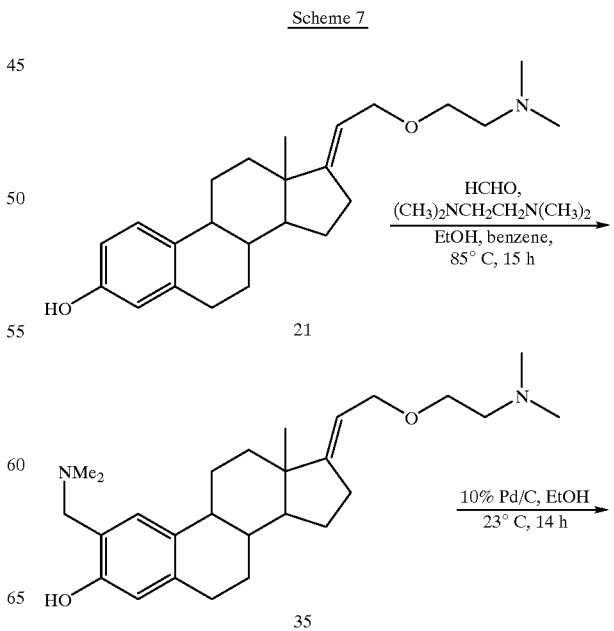

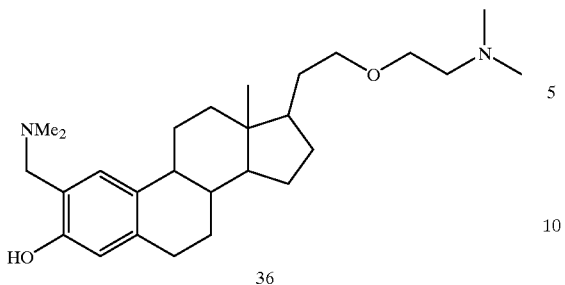

36

EXAMPLE 18

Preparation of (E)-3-Hydroxy-2-N,N-dimethylaminomethyl-21-[2'-(N',N'-dimethylamino)-ethoxy]-19-norpregna-1,3,5(10),17(20)-tetraene (35)

To a stirred solution of 100 mg (0.271 mmol) of (E)-3-Hydroxy-21-[2-(dimethylamino)ethoxy]-19-norpregna-1,3, 5(10),17(20)-tetraene 21 in 3 mL of benzene and 5 mL of ethanol was added 10 mg paraformaldehyde, and 0.054 g (0.528 mmol) of N,N,N',N'-tetramethyldiaminoethane, and the mixture was heated at 85° C. for 15 h under argon. Then, the reaction mixture was cooled, volatiles were removed under high vacuum, and the residue was subjected to chromatography (silica gel, 5–10% MeOH/CHCl₃) to afford 0.077 g (67%) of 35.

¹H NMR (CDCl₃, 300 MHz): δ0.80 (s, 3H), 2.32 (2, 12H), 2.57 (t, 2H, J=5.8 Hz), 2.82 (brd, 2H), 3.50–3.70 (m, 4H), 4.00 (t, 2H, J=5.8 Hz), 5.22 (m, 1H), 6.56 (2, 1H), 6.89 (s, 1H). MS (DCI) calculated for CHNO, 427; found, 427 (M+H; 100%).

EXAMPLE 19

Preparation of 3-Hydroxy-2-N,N-dimethylaminomethyl-21-[2'-(N',N'-dimethylamino)ethoxy]-19-norpregna-1,3,5(10)triene (36)

To a stirred solution of 0.040 g (0.09 mmol ) of (E)-3-hydroxy-2-dimethylaminomethyl-21-[2-(dimethylamino)ethoxy]-19-norpregna-1,3,5(10,17(20)-tetraene 35 in 4 mL of ethanol was added 5 mg of 10% palladium on carbon, and the mixture was stirred at room temperature under hydrogen for 14 h, filtered over celite pad, washed with ethylacetate, and the filtrate evaporated at room temperature to furnish a residue which was chromatographed (10% MeOH/CHCl₃) to afford 0.039 g (96%) of the product 36.

¹H NMR (CDCl₃, 300 MHz): δ0.62 (s, 3H), 2.32 (s, 6H), 2.42 (s, 6H), 2.65 (t, 2H, J=5.8 Hz), 3.40–3.70 (m, 6H), 6.57 (s, 1H), 6.88 (s, 1H). MS (DCI) calculated for CHNO, 429; found, 429 (M+H, 100%).

The following scheme illustrates the preparation of compound 45 as described in Example 20.

Scheme 8

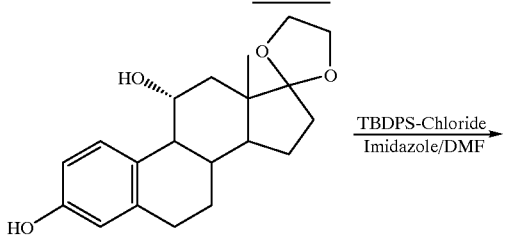

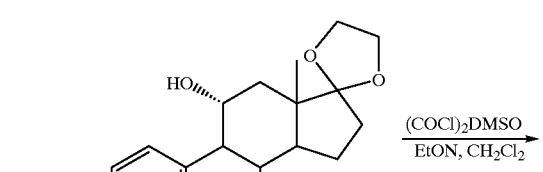

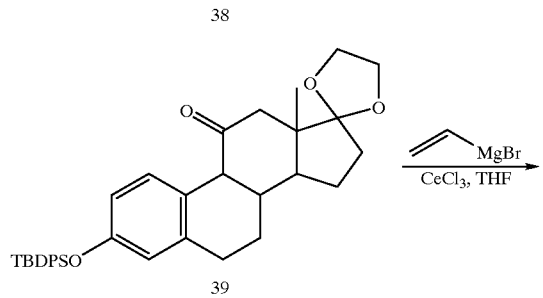

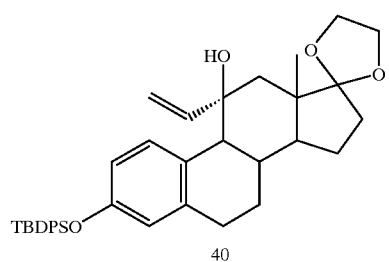

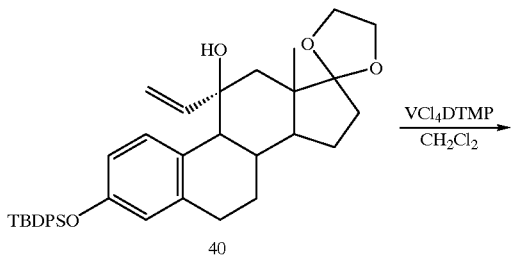

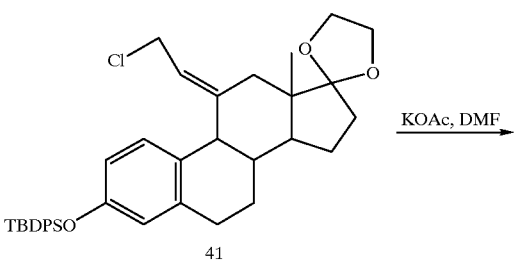

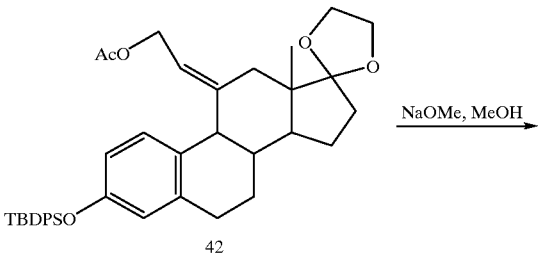

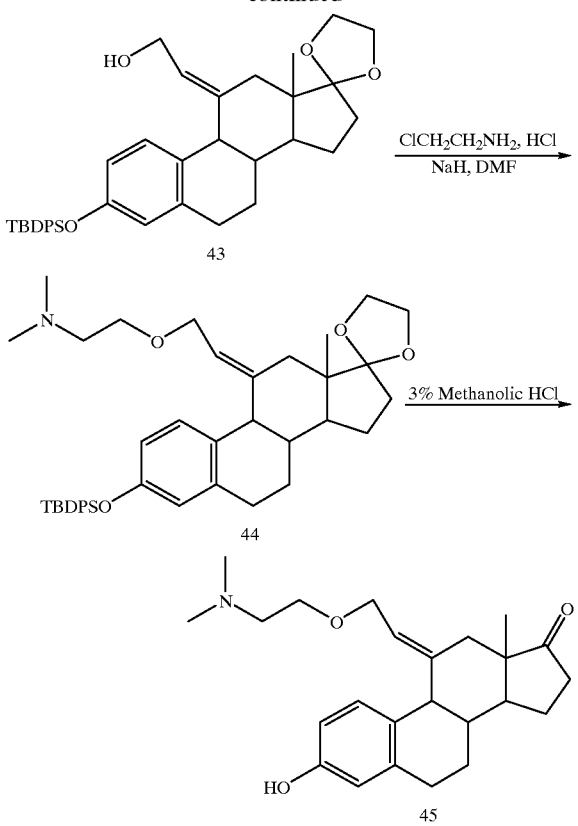

EXAMPLE 20

Preparation of 3-Hydroxy-11E-[2'-(2"-N,N-dimethylaminoethoxy-ethylidene)-1,3,5(10)-17-estrone (45)

(a) Preparation of 3-tert-butyldiphenylsilyloxy-17-ethylenedioxyestra-1,3,5(10)-trien-11-ol (38)

To a stirred solution of 6.3 g (0.019 mol) of 3-hydroxy-17-ethylenedioxyestra-1,3,5(10)-11-ol (37) in 20 mL anhydrous DMF were added 2.86 gm (0.042 mol) of imidazole, and 5.46 gm (0.021 mol) of tert-butyldiphenylsilyl chloride sequentially at room temperature under argon, and the mixture was stirred at 60° C. for 24 h, cooled to room temperature, diluted with water, and extracted with ether. The combined organic extract was washed with water, brine, and dried (Na$_2$SO$_4$). Evaporation of the solvent furnished a foam, which was chromatographed (30% ethyl acetate/hexanes) to afford the 6.5 gm (60%) of the intermediate 38 as a white solid.

$^1$H NMR (CDCl$_3$, 300 MHz): δ0.87 (s, 3H), 1.17 (s, 9H), 2.69 (brd, 2H), 3.85–3.98 (m, 4H), 4.15 (m, 1H), 6.60 (m, 2H), 7.34–7.48 (m, 6H), 7.69 (d, 1H, J=8.5 Hz), 7.80 (m, 4H).

(b) Preparation of 3-tert-Butyldiphenylsilyloxy-17-ethylenedioxyestra-1,3,5(10)-trien-11-one (39)

To a stirred solution of 1.5 mL (16.5 mmol) of oxalyl chloride in 15 mL of freshly distilled dichloromethane was added dropwise 2.35 mL (33.0 mmol) of dimethyl sufoxide at −65° C. (chloroform/dry ice bath) under argon atmosphere. After 10 minutes, a solution of 6.2 gm (10.9 mmol) of 3-tert-butyldiphenylsilyloxy-17-ethylenedioxyestra-1,3,5 (10)-11-ol 38 in 15 mL of dichloromethane was added dropwise, and the reaction mixture was stirred for 40 minutes at the same temperature. Then, a 12 mL (87.3 mmol) of triethylamine was added at −65° C., slowly allowed to attain room temperature, washed with saturated NH$_4$Cl solution, water, brine, and dried (Na$_2$SO$_4$). Evaporation of the solvent furnished a gum, which was chromatographed (15% ethyl acetate/hexanes) to afford 5.18 g (84%) the product 39.

$^1$H NMR (CDCl$_3$, 300 MHz): δ0.91 (s, 3H), 1.16 (s, 9H), 2.88 (d, 1H, J=12.7 Hz), 3.50 (d, 1H), 3.80–4.00 (m, 4H), 6.59 (brd, 1H), 6.65 (brd, 1H), 7.13 (d, 1H, J=8.5 Hz), 7.40 (m, 6H), 7.70 (m, 4H). MS (DCI) 584 (M+NH$_4$, 100%), 567 (M+H, 30).

(c) 3-tert-Butyldiphenylsilyloxy-11α-(1-ethenyl)-17-ethylenedioxyestra-1,3,5(10)-trien-11β-ol (40)

A 3.28 gm (1.76 mmol) of cerium (III) chloride heptahydrate was taken in a round bottom flask, and was heated under high vacuum at 120° C. for 2 h, cooled to room temperature under argon. Then, a 10 mL of dry THF was added, and the suspension was stirred for 1 h until a milky white suspension persisted. The flask was cooled to −78° C., and a 1 M solution of 5.28 mL (5.28 mmol) of vinylmagnesium bromide was slowly added under argon, and the mixture was stirred for 1 h at the same temperature. Then, a solution of 3.28 gm (8.8 mmol) of 3-tert-butyldiphenyl-silyloxy-17-ethylenedioxyestra-1,3,5(10)-11-one 39 in 20 mL THF was added dropwise at −78° C., the mixture stirred at −40° C. (acetonitrile/dry ice bath) for 3 h, quenched with saturated NH$_4$Cl solution, extracted with ether. The combined ether layers were washed with water, brine and dried (Na$_2$SO$_4$). Evaporation of the solvent furnished 0.860 mg (82%) of the product 40 as a white solid.

$^1$ NMR (CDCl$_3$, 300 MHz) δ: 1.10 (s, 9H), 1.16 (s, 3H), 3.80–3.95 (m, 4H), 5.10 (d, 1H), 6.62 (d, 1H), 7.40 (m, 6), 7.68 (d, 1H), 7.78 (m, 4H). MS (DCI): 612 (M+NH$_4$, 100%), 595 (M+H, 10).

(d) 3-tert-Butyldiphenylsilyloxy-11E-(2'-chloroethylidene)-17-ethylene-dioxyestra-1,3,5(10)-triene (41)

To a stirred solution of 0.80 g (1.34 mmol) of the 3-tert-butyldiphenylsilyloxy-11α-(1-ethenyl)-17-ethylenedioxyestra-1,3,5(10)-trien-11β-ol 40 (0.689 g, 3.35 mmol) of di-tert-butyl-4-methyl pyridine in 15 mL dry dichloromethane was added dropwise 0.17 mL (1.61 mmol) of vanadium tetrachloride at −20° C. under argon. The mixture was stirred for 3 h while allowing it to attain room temperature. The mixture was washed with water, brine, and dried (Na$_2$SO$_4$). Evaporation of the solvent furnished a residue, which was chromatographed (10% ethyl acetate/hexanes) to give 0.263 g (32%) of the product 41: $^1$H NMR(CDCl$_3$, 300MHz): δ0.80 (s, 3H), 1.10 (s, 9H), 3.10 (d, 1H, J=2.7 Hz, 3.92 (m, 4H), 4.00–4.24 (m, 2H), 5.69 (5, 1H, J=8.5 Hz), 6.62 (m, 2H), 6.95 (d, 1H, J=8.5 Hz), 7.40 (m, 6H), 7.72 (m, 4H). MS (DCI): 630 (M+NH4, 20%), 613 (M+H, 40), 577 (M+H−HCl, 100).

(e) Preparation of 3-tert-butyldiphenylsilyloxy-11E-(2'-acetoxyethylidene)-17-ethylenedioxyestra-1,3,5(10)-triene (42)

To a stirred solution of 0.3 g (0.49 mmol) of the 3-tert-butyldiphenylsilyloxy-11E-(2'-chloroethylidene)-17-ethylenedioxyestra-1,3,5(10)-triene 41 in 5 mL anhydrous DMF was added 0.482 g (4.89 mmol) of potassium acetate, and the mixture was stirred at room temperature for 24 h, poured into water, and extracted with ether. The combined organic extract was washed with water, brine, and dried (Na$_2$SO$_4$). Evaporation of the solvent furnished a residue, which was chromatographed (15% ethylacetate/hexanes) to give 0.162 g (52%) of product 42.

$^1$H NMR (CDCl$_3$, 300 MHz): δ0.80 (s, 3H), 1.10 (s, 9H), 2.00 (s, 3H), 2.16 (d, 1H, J=12.2 Hz), 3.07 (d, 1H, J=10.4 Hz), 3.95 (m, 4H), 4.54 (dd, 1H, J=12.4 Hz, J-6.44 Hz), 4.71 (dd, 1H, J=12.4 Hz, J=6.44 Hz), 4.71 (dd, 1H, J=12.4 Hz, J=7.40 Hz), 5.48 (t, 1H, J=6.7 Hz), 6.54 (m, 2H), 6.96 (d, 1H, J=9.5 Hz), 7.40 (m, 6H), 7.74 (m, 4H). MS (DCI): 654 (M+NH$_4$, 100%), 577 (M-HOAc+H, 80).

(f) Preparation of 3-tert-butyldiphenylsilyloxy-11E-(2'-hydroxyethylidene)-17-ethylenedioxyestra-1,3,5(10)-triene (43)

To a stirred solution of 0.06 g (0.094 mmol) of 3-tert-butyldiphenylsilyloxy-11E-(2'-acetoxy ethylidene)-17-ethylenedioxyestra-1,3,5(10)-triene 42 in 3 mL methanol was added few drops of 3% solution of sodium methoxide in methanol, and the mixture was stirred at room temperature for 3 h, quenched with saturated NH$_4$Cl solution, concentrated at room temperature, the residue was suspended in water, and extracted with ethyl acetate. The combined organic extract was washed with water, brine, and dried (Na$_2$SO$_4$). Evaporation of the solvent furnished a residue, which was chromatographed (20% ethyl acetate/hexanes) to give 0.056 g (96%) of the product 43.

$^1$H NMR (CDCl$_3$, 300 MHz): δ0.70 (s, 3H), 0.98 (s, 9H), 2.98 (d, 1H, J 12.7 Hz), 3.80 (m, 4H), 3.95–4.22 (m, 2H), 5.48 (t, 1H, J=6.8 Hz), 6.45 (m, 2H), 6.90 (d, 1H, J-8.5 Hz), 7.30 (m, 6H), 7.65 (m, 4H).

(g) Preparation of 3-hydroxy-11E-[2'-(2''-N,N-dimethylaminoethoxy-ethylidene)-1,3,5(10)-17-estrone (45)

To a suspension of 113 mg (2.83 mmol) of sodium hydride (60% in paraffin) in 3 mL anhydrous DMF was added 40 mg (0.283 mmol) of 2-chloroethylamine hydrochloride at 0° C., and the mixture was stirred for 10 minutes. Then, a solution of 54 mg (0.09 mmol) of 3-tert-butyldiphenylsilyloxy-11E-(2'-hydroxy ethylidene)-17-ethylenedioxyestra-1,3,5(10)-triene 43 in 3 mL of anhydrous DMF was added dropwise, and the mixture was heated at 50° C. under argon for 2 h, cooled, diluted with water, and extracted with ether. The combined organic extract was washed with water, brine, and dried (Na$_2$SO$_4$). Evaporation of the solvent furnished 3-tert-butyldiphenylsilyloxy-11E-[2'-(2''-dimethylaminoethoxyethylidene)-17-ethylenedioxyestra-1,3,5(10)-triene 44, to which was added 10 mL of 3% methanolic hydrogen chloride. The mixture was stirred for 3 h at room temperature, quenched with aqueous NH$_4$Cl solution, concentrated at room temperature, and the residue was partitioned between water and ethyl acetate, and the layers were separated. The aqueous phase was extracted with ethyl acetate, which was washed with water, brine, and dried (Na$_2$SO$_4$). Evaporation of the solvent fished a residue which was chromatographed (10% MeOH/CHCl$_3$) to afford the product 45.

$^1$H NMR (CDCl$_3$, 300 MHz): δ0.87 (s, 3H), 2.35 (s, 6H), 2.75 (t, 2H, J=5.7 Hz), 2.89 (d, 1H, J=12.7 Hz), 3.10 (d, 1H, J=9.77 Hz), 4.04 (dt, 2H, J=5.70 Hz, J=5.7 Hz), 2.89 (d, 1H, J=12.7 Hz), 3.10 (d, 1H, J=9.77 Hz), 4.04 (dt, 2H, J=5.70 Hz, J=1.22 Hz), 4.14 (dd, 1H, J=12.6 Hz, J=6.3 Hz), 4.34 (dd, 1H, J=12.6 Hz, J=7.12 Hz), 5.68 (t, 1H, J=6.8 Hz), 6.7 (d, 1H, J=2.7 Hz), 6.75 (dd, 1H, J=2.7 Hz, J=8.79 Hz). MS (DCI): 384 (M+H, 100%).

The following scheme illustrates the preparation of compounds 46 and 47 as described in Example 21.

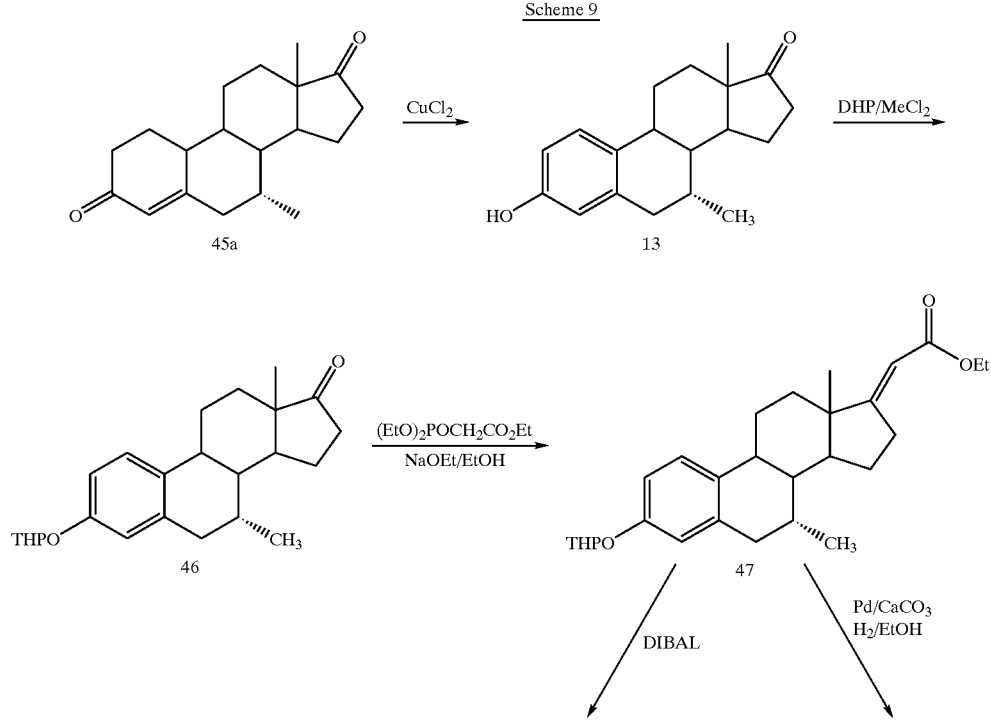

Scheme 9

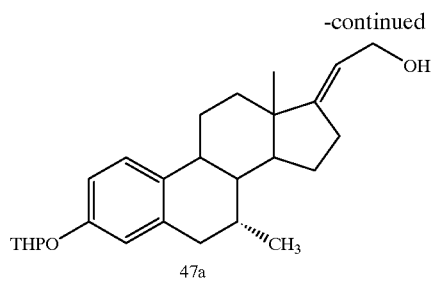
47a

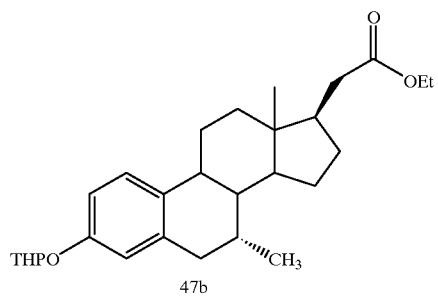
47b

EXAMPLE 21

Preparation of (E)-3-Tetrahydropyranyloxy-7α-methyl-19-norpregna-1,3,5 (10),17(20)-tetraene (47a) and (E)-3-Tetrahydropyranyloxy-7α-methyl-19-norpregna-1,3,5 (10)triene-21-oate (47b)

(a) Preparation of 7α-Methylestrone (13)

To a solution of 114 g of 7α-methylandrost-4ene-3,17-dione 45a in 1,500 mL of glacial acetic acid was added 106 g of $CuCl_2$. The mixture with stirring was heated to 60° C. for 72 h. The reaction mixture was poured into $H_2O$ (500 mL reaction mixture to 3,500 mL $H_2O$) and the precipitate collected by filtration and air dried for 18 h. The solid was dissolved in methylene chloride (2 L) and washed with sat. $NaHCO_3$ (2 L), $H_2O$ (2 L), and sat. NaCl (2 L). The methylene chloride solution was dried over $MgSO_4$, and filtered. The methylene chloride solution was filtered (suction chromatography) through 1.5 kg of flash chromatography silica gel 60 (230–400 mesh). The pad of silica gel was further eluted with additional $MeCl_2$. The $MeCl_2$ solutions were combined and then treated with Norite, filtered through a pad of celite and then after evaporation at reduced pressure there was obtained 91.3 g of pure 13 (82%).

(b) Preparation of 3-Tetrahydropyranyloxy-7α-methylestra-19-norpregna-1,3,5 (10)-trien-17-one (46)

To a mixture of 7α-methyl estrone 13 (8.18 g, 28.8 mmol) and DHP (4.0 mL, 43.9 mmol) in $CH_2Cl_2$ (100 mL) at 0° C. under argon was added a catalytic amount of p-TsOH, and the reaction mixture was stirred for 1 h. The reaction mixture was poured into saturated aqueous $NaHCO_3$ and extracted with $CH_2Cl_2$. The combined organic layers were dried over anhydrous $MgSO_4$, filtered, and concentrated to afford a pale yellow solid. Flash chromatography (5%; 10% EtOAc/hexane) yielded ether 46 as a white solid (10.12 g, 95%): $^1$H NMR (300 MHz, $CDCl_3$): δ0.88 (d, J=7.0 Hz, 3, $CH_3$), 0.90 (s, 3, $CH_3$), 5,39 (m, 1), 6.78 (d, J=2.5 Hz, 1, ArH), 6.85 (dd, J=2.5, 8.5 Hz, 1, ArH), 7.19 (d, J=8.5 Hz, 1, ArH).

(c) Preparation of Ethyl (E)-3-Tetrahydropyranyloxy-7α-methyl-19-norpregna-1,3, 5 (10),17(20)-tetraen-21-oate (47)

To a solution of 46 (10.12 g, 27.46 mmol) and triethyl phosphonoacetate (28 mL, 141.1 mmol) in EtOH (130 mL) and THF (30 mL) under argon at 40–45° C. was slowly added a 21 wt % solution of sodium ethoxide in EtOH (52.3 mL, 140 mmol), and the solution was heated to reflux overnight. The reaction mixture was cooled to room temperature and concentrated under reduced pressure. The mixture was then diluted with water and extracted with ether. The combined organic layers were dried over anhydrous $MgSO_4$, filtered, and concentrated to afford a yellow gum. Chromatography (5%; 10% EtOAc/hexane) gave ester 47 as a white foam (11 g, 91%): $^1$H NMR (300 MHz, $CDCl_3$): δ0.85 (d, J=7.0 Hz, 3, $CH_3$), 0.87 (s, 3, $CH_3$), 1.30 (t, J=7.1 Hz, 3 $CO_2CH_2CH_3$), 2,89 (m, 2), 3.10 (m, 1), 3.60 (m, 1), 3.94 (m, 1), 4.17 (q, J=7.1 Hz, 2, $CO_2CH_2CH_3$), 5.40 (m, 1), 5.59 (m, 1), 6.77 (d, J=2.5 Hz, 1, ArH), 6.86 (dd, J=2.5, 8.7 Hz, 1, ArH), 7.21 (d, J=8.7 Hz, 1, ArH).

(d) Synthesis of (E)-3-Tetrahydropyranyloxy-7α-methyl-21-hydroxy-19-norpregna-1,3,5(10),17(20)-tetraene (47a)

To a solution of ester 47 (11 g, 25 mmol) in THF (200 ml) was added a 1.0 M solution of diisobutylaluminum hydride ("DIBAL") in heptane (60 mL, 60 mmol) at −78° C. under argon, and the reaction mixture was warmed to 0° C. and stirred for 1.5 h. Methanol (5 mL) and water were added at 0° C., and the solution was warmed to room temperature and stirred for 30 min. The cloudy solution was extracted with EtOAc. The combined organic layers were dried over anhydrous $MgSO_4$, filtered, and concentrated to afford allylic alcohol 47a as a white solid (9.63 g, 97%): $^1$H NMR (300 MHz, $CDCl_3$): δ0.82 (s, 3, $CH_3$), 0.85 (d, J=7.0 Hz, 3, $CH_3$), 3.09 (m, 1), 3.60 (m, 1), 3.95 (m, 1), 4.15 (m, 2), 5.30 (m, 1), 5.39 (m, 1), 6.78 (d, J=2.2 Hz, 1, ArH), 6.85 (dd, J=2.2, 8.4 Hz, 1, ArH), 7.22 (d, J=8.4 Hz, 1, ArH).

(e) Preparation of Ethyl (E)-3-tetrahydropyranyloxy-7α-methyl-19-norpregna-1,3,5 (10)-trien-21-oate (47b)

A solution of 33.4 g of 47 in 450 mL of ethanol containing 25 mL of triethylamine and 2.0 g of 5% palladium of calcium carbonate in a 1 L flask was hydrogenated on a Parr shaker for 18 h. The catalyst was removed by filtration through a bed of celite. Additional ethanol was used to wash the bed of celite. The ethanol solutions were combined and evaporated to dryness under vacuum to afford 33.5 g (quantitative) of 47b as a clear oil.

The following scheme illustrates the preparation of compounds 48, 50 and 51 as described in Examples 23–25.

Scheme 10

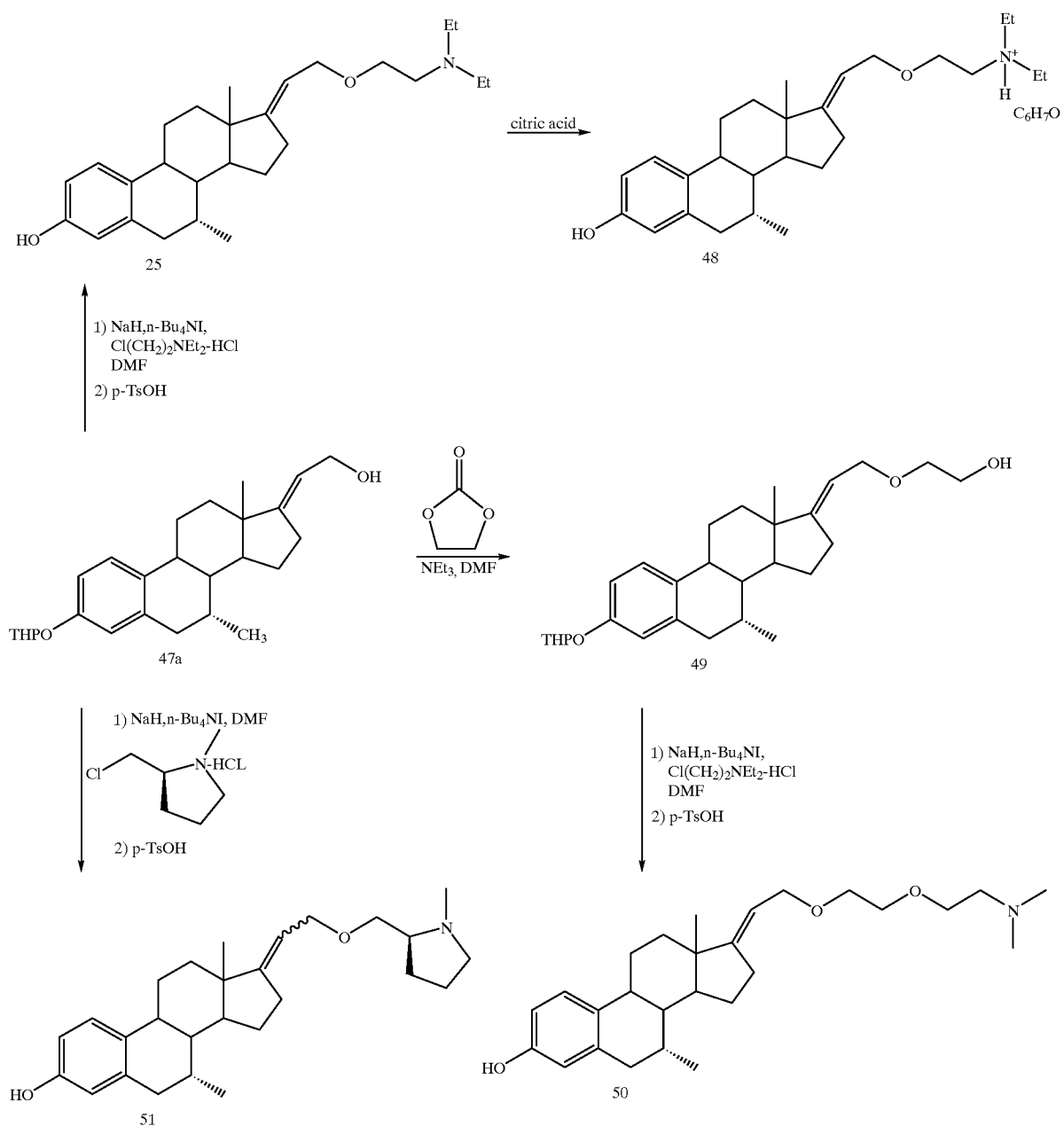

EXAMPLE 22

Preparation of the citrate of (E)-3-hydroxy-7α-methyl-21-[2'-(N,N-diethylamino)ethoxy]-19-norpregna-1,3,5 (10),17(20)-tetraene (48)

(a) Preparation of (E)-3-Hydroxy-7α-methyl-21-[2'-(N,N-diethylamino)-ethoxy]-19-norpregna-1,3,5 (10),17(20)-tetraene (25)

To a suspension of NaH (25.0 g, 625 mmol) in DMF (50 mL) at 0° C. under argon was added 2-N,N-diethylaminoethyl chloride hydrochloride (8.5 g, 49.4 mmol) in portion and stirred until no hydrogen was released. The reaction mixture was warmed to room temperature and allylic alcohol 47a (6.5 mL, 16.5 mmol) in DMF (30 mL) was added, and stirred for 10 min. n-Bu$_4$NI (0.7 g, 1.9 mmol) was added and the reaction mixture was heated to 70° C. for 2.5 h. The reaction mixture was slowly quenched with H$_2$O at room temperature and extracted with ethyl acetate. The combined organic layers were dried over anhydrous MgSO$_4$, filtered, and concentrated to afford THP ether of 25 as a crude gum (8.5 g).

To a solution of THP ether (8.5 g) in MeOH (80 ml) at room temperature was added p-TsOH (3.4 g, 18 mmol) and stirred for 10 min. The reaction mixture was diluted with water (150 mL) and methanol was evaporated under reduced pressure. The cloudy mixture was poured into saturated aqueous NaHCO$_3$ and extracted with ethyl acetate. The combined organic layers were dried over anhydrous MgSO$_4$, filtered, and concentrated to afford a white solid. Flash chromatography (5% methanol/chloroform) yielded amine 25 as a white solid (5.76 g, 85% for two steps): $^1$H NMR (300 MHz, CDCl$_3$) δ0.79 (s, 3, CH$_3$), 0.82 (d, J=7.0 Hz, 3, CH$_3$), 1.08 (t, J=7.2 Hz, 6, N(CH$_2$CH$_3$)$_2$), 2.50 (d, J=16.5 Hz, 1), 2.68 (t, J=7.2 Hz, 4, N(CH$_2$CH$_3$)$_2$), 2.76 (t, J=6.3 Hz, 2), 3.05 (dd, J=5.5, 16.5 Hz, 1), 3.59 (m, 2), 3.99 (m, 2), 5.21 (m, 1), 6.54 (d, J=2.7 Hz, 1, ArH), 6.62 (dd, J=2.7, 8.3 Hz, 1, ArH), 7.15 (d, J=8.3 Hz, 1, ArH).

(b) Preparation of the citrate of (E)-3-hydroxy-7α-methyl-21-[2'-(N,N-diethylamino)-ethoxy]-19-norpregna-1,3,5 (10),17(20)-tetraene (48)

To a solution of amine 25 (0.13 g, 0.32 mmol) in 10 mL of MeOH at room temperature under argon was added citric acid (0.61 g, 0.32 mmol) and stirred for 15 min. The solvent was evaporated under reduced presure and dried on pump overnight to afford the citrate salt 48 as a white solid in quantitative yield: $^1$H NMR (300 MHz, CD$_3$OD) δ0.83 (d, J=7.0 Hz, 3, CH$_3$), 0.85 (s, 3, CH$_3$), 1.31 (t, J=7.1 Hz, 6, N(CH$_2$CH$_3$)$_2$), 2.72 (d, J=15.4 Hz, 2), 2.82 (d, J=15.4 Hz, 2), 3.01 (dd, J=5.7, 16.5 Hz, 1), 3.25 (t, J=7.2 Hz, 4, N(CH$_2$CH$_3$)$_2$), 3.73 (m, 2), 4.07 (m, 2), 5.24 (m, 1), 6.46 (d, J=2.5 Hz, 1, ArH), 6.54 (dd, J=2.5, 8.8 Hz, 1, ArH), 7.09 (d, J=8.8 Hz, 1, ArH).

EXAMPLE 23

Preparation of (E)-3-Hydroxy-7α-methyl-21-{2'-[2"-(N,N-dimethylamino)-ethoxy]ethoxy}-19-norpregna-1,3,5 (10),17(20)-tetraene (50)

(a) Preparation of (E)-3-Tetrahydropyranyloxy-7α-methyl-21-[2'-(hydroxy)-ethoxy]-19-norpregna-1,3,5 (10),17(20)-tetraene (49)

A mixture of allylic alcohol 47a (1.0 g, 2.52 mmol), ethylene carbonate (0.33 g, 3.78 mmol), and triethylamine (0.26 g, 2.52) mmol in DMF (0.6 mL) was heated to 120° C. for overnight. The reaction mixture was cooled to room temperature and subjected to flash chromatography (30% EtOAc/hexane). The starting material 47a was recovered as a white solid (0.6 g), and the desired alcohol 49 was observed as a white foam (0.14 g, 32% based on recovered starting material): $^1$H NMR (300 MHz, CDCl$_3$) δ0.82 (s, 3, CH$_3$), 0.85 (d, J=7.0 Hz, 3, CH$_3$), 2.55 (dd, J=5.5, 17.0 Hz, 1), 3.09 (m, 1), 5.25 (m, 1), 5.39 (m, 1), 6.77 (d, J=2.5 Hz, 1, ArH), 6.85 (dd, J=2.5, 8.7 Hz, 1, ArH), 7.21 (d, J=8.7 Hz, 1, ArH).

(b) Preparation of (E)3-Hydroxy-7α-methyl-21-{2'-[2"-(N,N-dimethylamino)ethoxy]ethoxy}19-norpregna-1,3,5 (10),17(20)-tetraene (50)

The amine 50, which was prepared from alcohol 49 (0.13 g, 0.30 mmol) and 2-dimethylaminoethyl chloride hydrochloride (0.15 g, 1.0 mmol) and deprotected using the same procedure as described for amine 25, was obtained as a white solid (0.11 g, 85% for two steps): $^1$H NMR (300 MHz, CDCl$_3$) δ0.80 (s, 3, CH$_3$), 0.83 (d, J=7.0 Hz, 3, CH$_3$), 2.34 (s, 6, N(CH$_3$)$_2$), 3.05 (dd, J=6.2, 16.4 Hz, 1), 3.62 (m, 6), 3.96 (m, 2), 5.22 (m, 1), 6.54 (d, J=2.5 Hz, 1, ArH), 6.63 (dd, J=2.5, 8.0 Hz, 1, ArH), 7.16 (d, J=8.0 Hz, 1, ArH).

EXAMPLE 24

Preparation of (E)- and (Z)-3-Hydroxy-7α-methyl-21-[2'-(pyrrolidinyl)methoxy]-19-norpregna-1,3,5 (10),17(20)-tetraene (51)

To a suspension of NaH (1.0 g, 25 mmol) in DMF (30 mL) at 0° C. under argon was added 2-pyrrolidinemethyl chloride hydrochloride (1.29 mL, 7.56 mmol) in portion and stirred until no hydrogen was released. The reaction mixture was warmed to rt and allylic alcohol 46 (1.0 g, 2.52 mmol) in DMF (10 mL) was added, and stirred for 10 min. n-Bu$_4$NI (0.22 g, 0.6 mmol) was added and the reaction mixture was heated to 120° C. overnight. The reaction mixture was slowly quenched with H$_2$O at room temperature and extracted with ethyl acetate. The combined organic layers were dried over anhydrous MgSO$_4$, filtered, and concentrated to afford black gum. The crude mixture was dissolved in MeOH and p-TsOH was added until the solution was acidic. The reaction mixture was diluted with water and the methanol was evaporated under reduced pressure. The cloudy mixture was poured into saturated aqueous NaHCO$_3$ and extracted with ethyl acetate. The combined organic layers were dried over anhydrous MgSO$_4$, filtered, and concentrated to afford a white solid. Flash chromatography (5% methanol/chloroform) yielded the E and Z isomeric mixture (4:1) as a pale yellow solid (0.26 g, 25%): E isomer of 51: $^1$H NMR (300 MHz, CDCl$_3$) δ0.79 (s, 3, CH$_3$), 0.81 (d, J=7.0 Hz, 3, CH$_3$), 2.46 (s, 6, N(CH$_3$)$_2$), 3.08 (m, 2), 3.40 (m, 1), 3.52 (m, 1), 4.00 (m, 2), 5.22 (m, 1), 6.53 (d, J=2.5 Hz, 1, ArH), 6.62 (dd, J=2.5, 8.6 Hz, 1, ArH), 7.15 (d, J=8.6 Hz, 1, ArH). Z isomer of 51: $^1$H NMR (300 MHz, CDCl$_3$) δ0.76 (s, 3, CH$_3$), 0.86 (d, J=7.0 Hz, 3, CH$_3$), 2.45 (s, 6, N(CH$_3$)$_2$), 3.59 (m, 1), 5.36 (m, 1), 6.53 (d, J=2.5 Hz, 1, ArH), 6.63 (dd, J=2.5, 9.0 Hz, 1, ArH), 7.14 (d, J=9.0 Hz, 1, ArH).

The following scheme illustrates the preparation of compound 59 as described in Example 25.

Scheme 11

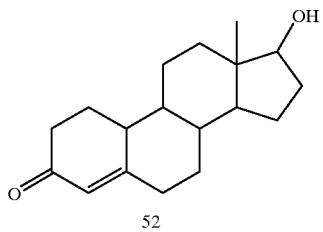

52

CrO$_3$, acetic acid →

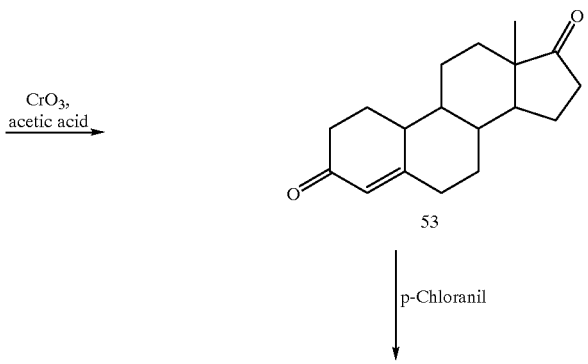

53

↓ p-Chloranil

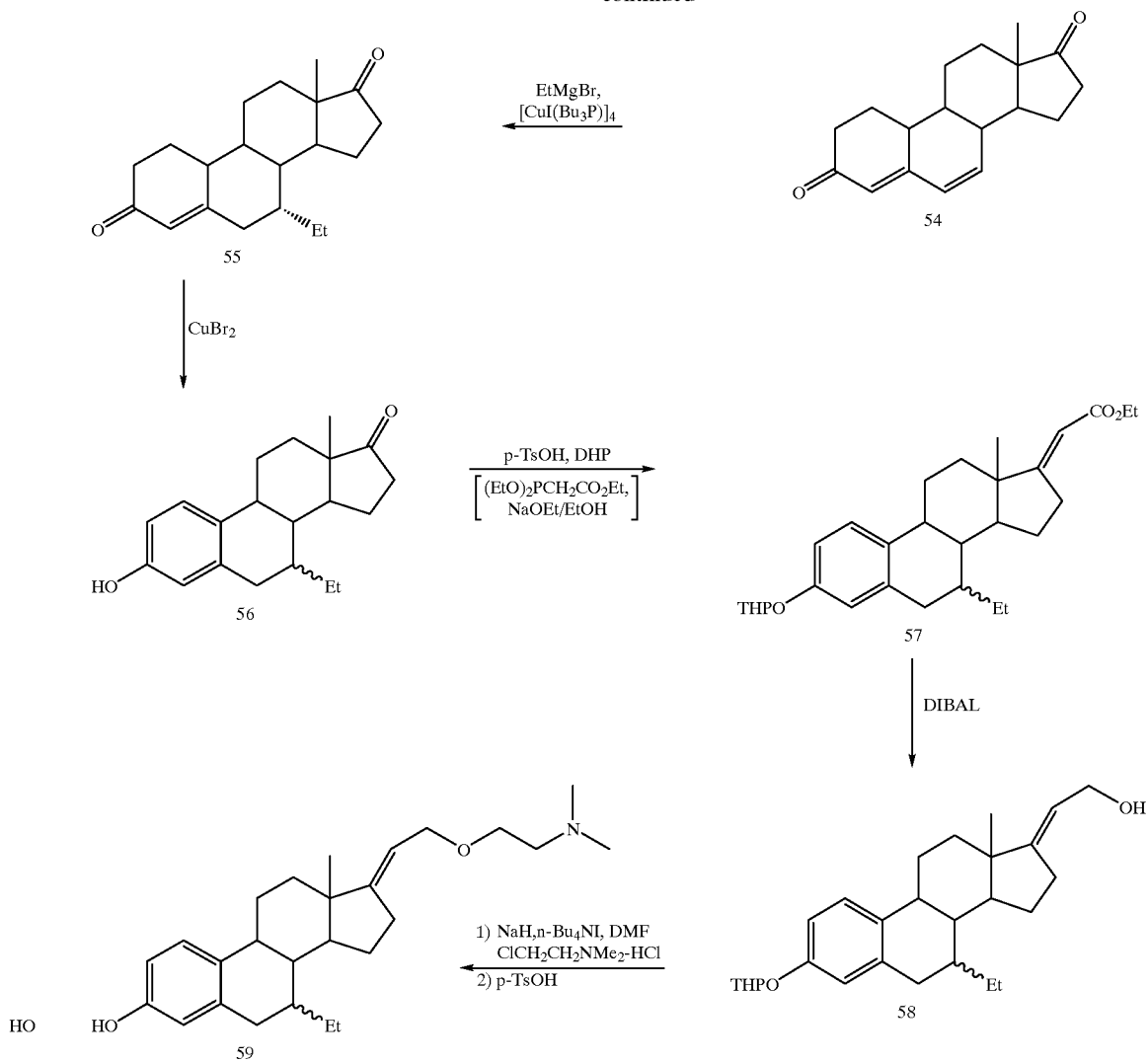

EXAMPLE 25

Preparation of (E)-3-hydroxy-7α- and 7β-ethyl-21-[2'-(N,N-diethylamino)ethoxy]-19-norpregna-1,3,5(10),17(20)-tetraene (59)

(a) Preparation of Estra-4-ene-3,17-dione (53)

To a solution of 19-nortestosterone 52 (26.85 g, 97.85 mmol) in acetic acid (200 mL) was added a CrO₃ (7.4 g, 74 mmol) in acetic acid (150 mL) and stirred for 1 h at room temperature. The reaction mixture was concentrated under reduced pressure to half of its initial volume, poured into 1 M hydrochloric acid (500 mL) and extracted with EtOAc. The combined organic layers were washed with saturated aqueous NaHCO₃, dried over anhydrous MgSO₄, filtered, and then concentrated to afford dione 53 as a white solid (25.3 g, 95%): ¹H NMR (300 MHz, CDCl₃) δ0.94 (s, 3, CH₃), 5.85 (s, 1).

(b) Preparation of Estra-4,6-diene-3,17-dione (54)

A solution of dione 53 (5.0 g, 18.36 mmol) and chloranil (5.4 g, 22 mmol) in dry ethanol (500 mL) was stirred at 60–65° C. for 2 h. The reaction mixture was concentrated under reduced pressure, and the residue was triturated with dichloromethane. The solid was removed by filtration, and the filtrate was concentrated to give a brown gum. Chromatography (20% EtOAc/hexane) yielded crude dione 54 as a yellow solid (2.3 g, 46%): ¹H NMR (300 MHz, CDCl₃) δ0.94 (s, 3, CH₃), 5.78 (s, 1), 6.25 (m, 2).

(c) Preparation of a mixture of 7α-and 7β-ethyl-estr-4-ene-3,17-dione (55)

To a mixture of CuI(Bu₃P)₄ (15.7 g, 40 mmol) in THF (50 mL) was added a 1.0 M solution of EtMgBr in THF (40 mL, 40 mmol) at −30° C., and stirred for 20 min. The reaction mixture was cooled to −78° C. and dione 54 (3.5 g, 12.94 mmol) was added. The reaction mixture was warmed to −30° C. for 0.5 h, and poured into saturated aqueous NH₄Cl. The mixture was extracted with EtOAc. The combined organic layers were dried over anhydrous MgSO₄, filtered, and then concentrated to afford a solid. Chromatography (20% EtOAc/hexane) yielded dione 55 as a yellow solid (1.5 g, 39%). The major 7α-ethyl isomer of 55: ¹H NMR (300 MHz, CDCl₃) δ0.89 (T, J=7.0 Hz, 3, CH₂CH₃), 0.93 (s, 3, CH₃), 2.60 (dd, J=2.4, 14.3 Hz, 1), 5.85 (s, 1).

(d) Preparation of a mixture of 3-tetrahydropyranyloxy-7α- and 7β-ethyl-estra-1,3,5(10)-trien-17-one (56)

To a solution of enone 55 (0.35 g, 1.17 mmol) in acetonitrile (10 mL) was added a CuBr$_2$ (0.31 g, 1.4 mmol) and stirred overnight at room temperature. Water was added until disappearance of the green color, and the acetonitrile was removed under reduced pressure. The residue was extracted with EtOAc. The combined organic layers were dried over anhydrous MgSO$_4$, filtered, and the combined organic layers were washed with water; brine, dried over anhydrous MgSO$_4$, filtered, and concentrated to afford a gum. Chromatography (20% EtOAc/hexane) yielded estrone 56 as a yellow solid (0.28 g, 80%): The major 7α-ethyl isomer of 56: $^1$H NMR (300 MHz, CDCl$_3$) δ0.91 (s, 3, CH$_3$), 0.95 (t, J=7.3 Hz, 3, CH$_2$CH$_3$), 6.59 (d, J=2.5 Hz, 1, ArH), 6.65 (dd, J=2.5, 8.4 Hz, 1, ArH), 7.13 (d, J=8.4 Hz, 1, ArH).

(e) Preparation of a mixture of ethyl (E)-3-tetrahydropyranaloxy-7α- and 7β-ethyl-19-norpregna-1,3,5(10), 17(20)-tetraen-21-oate (57)

The corresponding THP ether of 56, which was prepared from estrone 56 (0.28 g, 0.94 mmol) and DHP (0.2 mL, 2.2 mmol) using the same procedure as described for the ether, was obtained as a crude gum (0.4 g).

The ester 57, which was prepared from crude THP ether of 56 (0.4 g) and triethyl phosphonoacetate (1.12 g, 5.0 mmol), using the same procedure as described for compound 47a, was obtained as a solid (0.34 g, 81% for two steps). The major 7α-ethyl isomer of 57: $^1$H NMR (300 MHz, CDCl$_3$) δ0.87 (s, 3, CH$_3$), 0.93 (t, J=6.6 Hz, 3, CH$_2$CH$_3$), 1.30 (t, J=7.1 Hz, 3, CO$_2$CH$_2$CH$_3$), 2.40 (m, 2), 2.88 (m, 3), 3.60 (m, 1), 3.95 (m, 1), 4.17 (q, J=7.1 Hz, 2, CO$_2$CH$_2$CH$_3$), 5.39 (m, 1), 5.59 (m, 1), 6.79 (d, J=2.5 Hz, 1, ArH), 6.85 (dd, J=2.5, 8.8 Hz, 1, ArH), 7.19 (d, J=8.8 Hz, 1, ArH).

(f) Preparation of a mixture of (E)-3-tetrahydropyranaloxy-7α- and 7β-ethyl-21-hydroxy-19-norpregna-1,3,5 (10),17(20)-tetraene (58)

The allylic alcohol 58, which was prepared from ester 57 (0.34 g, 0.76 mmol) and DIBAL (2.0 g, 2.0 mmol) using the same procedure as described for compound 46, was obtained as a white solid (0.28 g, 89%). The major 7α-ethyl isomer of 58: $^1$H NMR (300 MHz, CDCl$_3$) δ0.81 (s, 3, CH$_3$), 0.93 (t, J=7.1 Hz, 3, CH$_2$CH$_3$), 2.39 (m, 4), 2.85 (m, 3), 3.60 (m, 1), 3.95 (m, 1), 4.15 (m, 2), 5.30 (m, 1), 5.39 (m, 1), 6.79 (d, J=2.5 Hz, 1, ArH), 6.85 (dd, J=2.5, 8.7 Hz, 1, ArH), 7.21 (d, J=8.7 Hz, 1, ArH).

(g) Preparation of a mixture of (E)-3-hydroxy-7α- and 7β-ethyl-21-[2'-(N,N-dimethylamino)ethoxy]-19-norpregna-1,3,5 (10),17(20)-tetraene (59)

The amine 59, which was prepared from alcohol 58 (0.28 g, 0.698 mmol) and 2-dimethylaminoethyl chloride hydrochloride (0.3 g, 2.1 mmol), and deprotected using the same prodedure as described for amine 25, was obtained as the 7α-ethyl and 7β-ethyl isomeric mixture (10:1) as a solid (0.21 g, 78% for two steps). The major 7α-ethyl isomer of 59: $^1$H NMR (300 MHz, CDCl$_3$) δ0.77 (s, 3, CH$_3$), 0.84–1.02 (m, 4), 2.42 (s, 6, N(CH$_3$)$_2$), 3.61 (m, 2), 3.99 (m, 2), 5.19 (m, 1), 6.55 (d, J=2.6 Hz, 1, ArH), 6.62 (dd, J=2.6, 8.5 Hz, 1, ArH), 7.12 (d, J=8.5 Hz, 1, ArH).

The following scheme illustrates the preparation of compounds 67 and 68 as described in Example 26.

Scheme 12

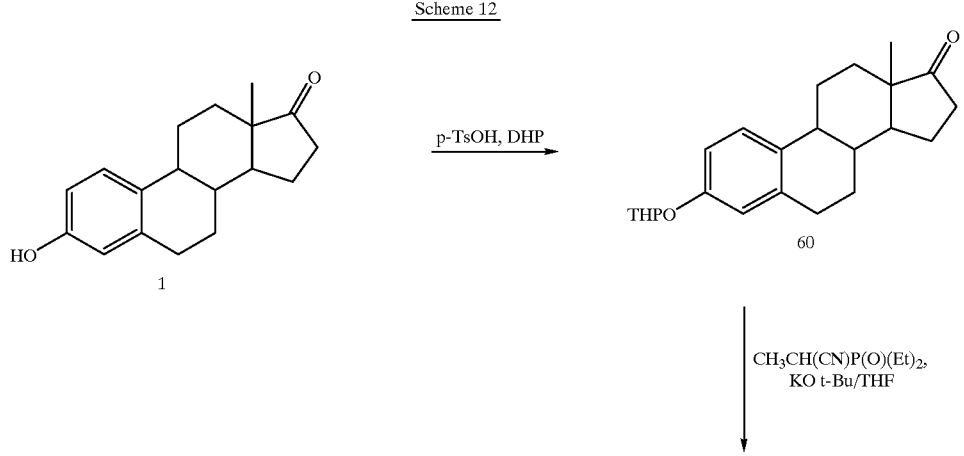

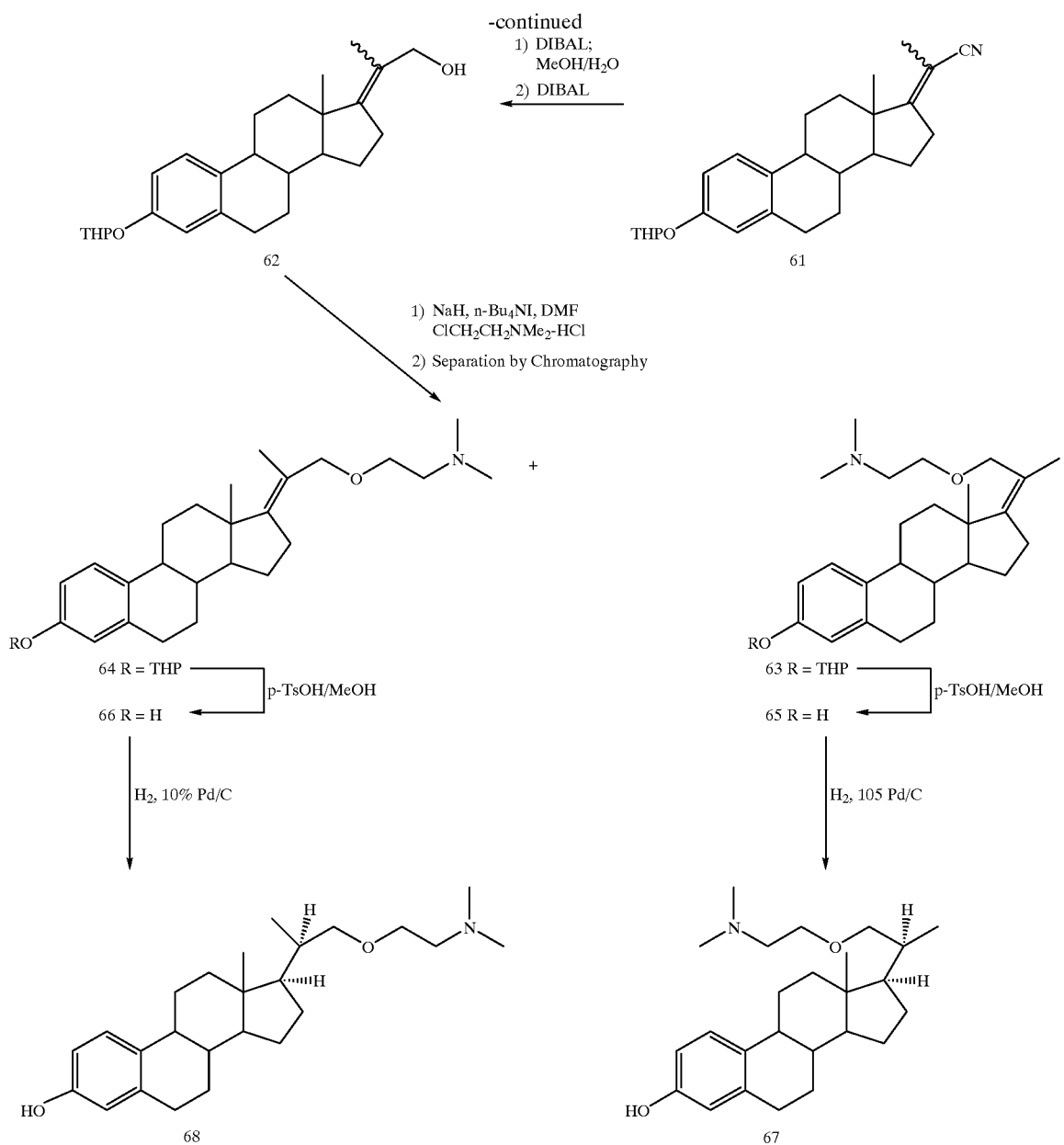

EXAMPLE 26
Preparation of (R) and (S)-3-Hydroxy-20-methyl-21-[2'-(N,N-diethylamino)ethoxy]-19-pregna-1,3,5(10)-triene (68)

(a) Preparation of 3-Tetrahydropyranyloxyestra-1,3,5(10)-trien-17-one (60)

The THP ether 60, which was prepared from estrone 1 (6.3 g, 23.3 mmol) and DHP (3.0 g, 33 mmol) using the same procedure as described for compound 35, was obtained as a white solid (7.5 g, 91%): $^1$H NMR (300 MHz, CDCl$_3$) δ 0.91 (s, 3, CH$_3$), 2.89 (m, 2), 3.60 (m. 1), 3.92 (m, 1), 5.40 (m, 1), 6.81 (d, J=2.5 Hz, 1, ArH), 6.86 (dd, J=2.5, 8.5 Hz, 1, ArH), 7.20 (d, J=8.5 Hz, 1, ArH).

(b) Preparation of (E,Z)-3-tetrahydropyranyloxy-20-methyl-21-hydroxy-19-norpregna-1,3,5(10),17(20)-tetraene (62)

To a solution of diethyl (1-cyanoethyl)phosphonate (3.98 g, 20.81 mmol) in THF under argon at room temperature was added a 1.0 M solution of potassium t-butaoxide in THF (20 mL, 20 mmol), and stirred for 1.0 h. A solution of estrone 1 (3.0 g, 8.46 mmol) in THF (10 mL) was added, and the solution was heated to reflux overnight. The reaction mixture was poured into saturated aqueous NaHCO$_3$ and extracted with 40% ethyl acetate/hexane. The combined organic layers were dried over anhydrous MgSO$_4$, filtered, and concentrated to afford the E and Z isomeric mixture as a yellow gum. Flash chromatography (10% EtOAc/hexane) yielded mixture of (Z)- and (E)-20-carbonitrile-3-tetrahydropyranaloxy-19-norpregna-1,3,5 (10),17(20)-tetraene 61. (0.83 g, 25%).

To a solution of nitrile 61 (0.83 g, 2.12 mmol) in toluene/TRF was added a 1.0 M solution of DIBAL in heptane (2.5 mL, 2.5 mmol) at −78° C. under argon, and the reaction mixture was warmed to room temperature and stirred for 3 h. Methanol (0.5 mL) and water (0.5 mL) were added, and the solution was stirred for 40 min. The cloudy solution was extracted with EtOAc. The combined organic layers were dried over anhydrous MgSO₄, filtered, and concentrated to afford the corresponding aldehyde as a gum. To a solution of crude aldehyde (0.85 g) in THF was added a 1.0 M solution of DIBAL in heptane (3.0 mL, 3.0 mmol) at −78° C. under argon, and the reaction mixture was warmed to 0° C. and stirred for 1 h. Methanol (0.5 mL) and water (0.5 mL) were added, and the solution was stirred for 20 min at room temperature. The cloudy solution was extracted with EtOAc. The combined organic layers were dried over anhydrous MgSO₄, filtered, and concentrated to afford the E and Z mixture of allylic alcohol 62 as a solid (0.45 g, 53% for two steps).

(c) Preparation of (Z)-3-tetrahydropyranyloxy-20-methyl-21-[2'-(N,N-diethylamino)ethoxy]-19-norpregna-1,3,5(10),17(20)-tetraene (63) and (E)-3-tetrahydropyranyloxy-20-methyl-21-[2'-(N,N-diethylamino)ethoxy]-19-norpregna-1,3,5(10),17(20)-tetraene (64)

Amines 63 and 64, which were prepared from alcohol 62 (0.45 g, 1. 13 mmol) and 2-dimethylaminoethyl chloride hydrochloride (0.5 g, 3.5 mmol) using the same prodedure as described for amine 25, was obtained as a solid. Flash chromatography (5% methanol/chloroform) gave the Z isomer 63 as a major product (0.34 g, 65%), and the desired E isomer 64 as a minor product (0.13 g, 25%). Z isomer 63: $^1$H NMR (300 MHz, CDCl₃) δ0.90 (s, 3, CH₃), 1.65 (s, 3, CH₃), 2.30 (s, 6, N(CH₃)₂), 2.55 (t, J=6.0 Hz, 2), 2.85 (m, 2), 3.51 (t, J=6.0 Hz, 2), 3.60 (m, 1), 3.91 (m, 1), 3.98 (d, J=11.0 Hz, 1), 3.98 (d,J=11.0 Hz, 1), 4.20 (d, J=11.0 Hz, 1), 5.39 (m, 1), 6.79 (d, J=2.5 Hz, 1, ArH), 6.85 (dd, J=2.5, 8.4 Hz, 1, ArH), 7.19 (d, J=8.4 Hz, 1, ArH). E isomer 64: $^1$H NMR (300 MHz, CDCl₃) δ(0.90 (s, 3, CH₃), 1.79 (s, 3, CH₃), 2.32 (s, 6, N(CH₃)₂), 2.57 (t, J=6.0 Hz, 2), 2.86 (m, 2), 3.49 (m, 2), 3.60 (m, 1), 3.59 (m, 1), 3.92 (m, 3), 5.39 (m, 1) 6.79 (d, J=2.5 Hz, 1, ArH), 6.85 (dd, J=2.5, 8.4 Hz, 1, ArH), 7.19 (d, J=8.4 Hz, 1, ArH).

(d) Preparation of (Z)-3-Hydroxy-20-methyl-21-[2'-(N,N-diethylamino)-ethoxy]-19-norpregna-1,3,5(10),17(20)-tetraene (65)

The amine 65, which was prepared from ether 63 (0.34 g, 0.73 mmol) and p-TsOH (0.15 g, 0.8 mmol) using the same procedure as described for amine 25, was obtained as a white solid (0.27 g, 95%): $^1$H NMR (300 MHz, CDCl₃) δ0.84 (s, 3, CH₃), 1.64 (s, 3, CH₃), 2.39 (s, 6, N(CH₃)₂), 2.67 (t, J=6.0 Hz, 2), 2.81 (m, 2), 3.58 (t, J=6.0 Hz, 2), 3.90 (d, J=11.0 Hz, 1), 4.19 (d, J=11.0 Hz, 1), 6.54 (d, J=2.5 Hz, 1, ArH), 6.61 (dd, J=2.5, 8.2 Hz, 1, ArH), 7.11 (d, J=8.2 Hz, 1, ArH).

(e) Preparation of (E)-3-Hydroxy-20-methyl-21-[2'-(N,N-diethylamino)ethoxy]-19-norpregna-1,3,5(10),17(20)-tetraene (66)

The amine 66, which was prepared from ether 64 (0.13 g, 0.28 mmol) and p-TsOH (0.06 g, 0.31 mmol) using the same procedure as described for amine 25, was obtained as a white solid (0.1 g, 93%): $^1$H NMR (300 MHz, CDCl₃) δ0.84 (s, 3, CH₃), 1.77 (s, 3, CH₃), 2.39 (s, 6, N(CH₃)₂), 2.64 (t, J=5.7 Hz, 2), 2.82 (m, 2), 3.53 (m, 2), ), 3.86 (d, J=11.2 Hz, 1), 3.95 (d, J=11.2 Hz, 1), 6.54 (d, J=2.7 Hz, 1, ArH), 6.59 (dd, J=2.7, 8.2 Hz, 1, ArH), 7.12 (d, J=8.2 Hz, 1, ArH).

(f) Preparation of (17R,20S)-20-[(4'-N,N-Dimethyl)-2'-oxabutyl]-19-norpregna-1,3,5(10)-trien-3-ol (67)

The olefin 65 (35 mg, 0.09 mmol) was hydrogenated over 10% palladium on charcoal (10 mg) in 5 mL of ethanol at room temperature under atmospheric pressure overnight. The catalyst was removed by filtration, and washed with ethanol. The solvent was removed in vacuo to give a white solid. Flash chromatography (5% methanol/chloroform) yielded amine 67 as a white solid (30 mg, 86%): $^1$H NMR (300 MHz, CDCl₃) δ0.68 (s, 3, CH₃), 1.04 (d, J=6.6 Hz, 3, CH₃), 2.37 (s, 6, N(CH₃)₂), 2.64 (m, 2), 2.79 (m, 2), 3.14 (dd, J=7.6, 8.8 Hz, 1), 3.40 (dd, J=3.3, 9.3 Hz, 1), 3.56 (m, 2), 6.54 (d, J=2.6 Hz, 1, ArH), 6.61 (dd, J=2.6, 8.5 Hz, 1, ArH), 7.12 (d, J 8.5 Hz, 1, ArH).

(g) Preparation of (17R,20R)-20-[(4'-N,N-Dimethyl)-2'-oxabutyl]-19-norpregna-1,3,5(10)-trien-3-ol (68)

The olefin 66 (25 mg, 0.065 mmol) was hydrogenated over 10% palladium on charcoal (10 mg) in 5 mL of ethanol at room temperature under atmospheric pressure overnight. The catalyst was removed by filtration, and washed with ethanol. The solvent was removed in vacuo to give a white solid. Chromatography (5% methanol/chloroform) yielded amine 68 as a white solid (22 mg, 88%): $^1$H NMR (300 MHz, CDCl₃) δ0.68 (s, 3, CH₃), 0.94 (d, J=6.6 Hz, 3, CH₃), 2.36 (s, 6, N(CH₃)₂), 2.62 (m, 2), 2.80 (m, 2), 3.21 (dd, J=7.8, 9.0 Hz, 1), 3.55 (m, 3), 6.54 (d, J 2.6 Hz, 1, ArH), 6.60 (dd, J=2.6, 8.5 Hz, 1, ArH), 7.12 (d, J=8.5 Hz, 1, ArH).

The following scheme illustrates the preparation of compounds 69, 70 and 71 as described in Examples 27, 28 and 29:

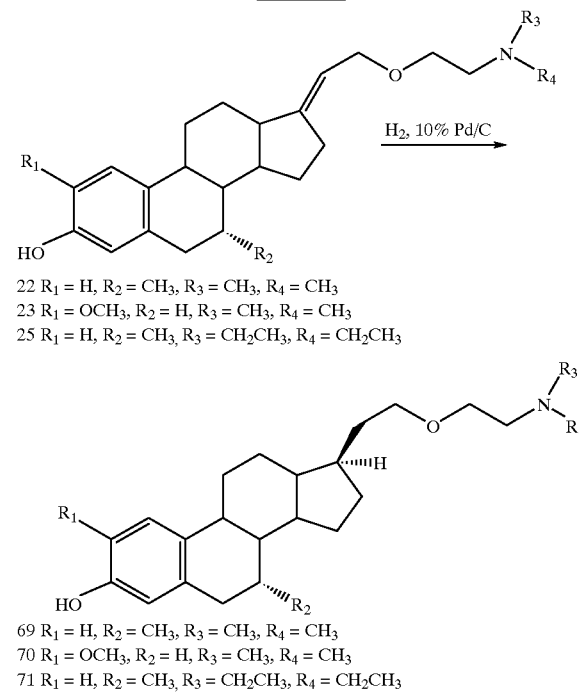

Scheme 13

22 R₁ = H, R₂ = CH₃, R₃ = CH₃, R₄ = CH₃
23 R₁ = OCH₃, R₂ = H, R₃ = CH₃, R₄ = CH₃
25 R₁ = H, R₂ = CH₃, R₃ = CH₂CH₃, R₄ = CH₂CH₃

69 R₁ = H, R₂ = CH₃, R₃ = CH₃, R₄ = CH₃
70 R₁ = OCH₃, R₂ = H, R₃ = CH₃, R₄ = CH₃
71 R₁ = H, R₂ = CH₃, R₃ = CH₂CH₃, R₄ = CH₂CH₃

EXAMPLE 27

Preparation of 3-Hydroxy-7α-methyl-21-[2'-(N,N-dimethylamino)ethoxy]-19-norpregna-1,3,5(10)-triene (69)

The olefin 22 (35 mg, 0.09 mmol) was hydrogenated over 10% palladium on charcoal (10 mg) in 5 mL of ethanol at room temperature under atmospheric pressure overnight. The catalyst was removed by filtration and washed with ethanol. The solvent was removed in vacuo to give a white solid. Flash chromatography (5% methanol/chloroform) yielded amine 69 as a white solid (0.030 g, 86%):mp 162–165° C.; $^1$H NMR (300 MHz CDCl$_3$): δ0.62 (s, 3, CH$_3$), 0.84 (d, J=7.1 Hz, 3, CH$_3$), 2.32 (s, 6, N(CH$_3$)$_2$), 2.49 (dd, J=1.2, 16.2 Hz, 1), 2.57 (t, J=5.8 Hz, 2), 3.04 (m, 1), 3.44 (m, 2), 3.56 (t, J=5.8 Hz, 2), 6.54,(d, J=2.7 Hz, 1, ArH), 6.62 (dd, J=2.7, 8.0 Hz, 1, ArH), 7.16 (d, J=8.0 Hz, 1, ArH). HRMS for CH$_{25}$H$_{39}$NO$_2$ (M$^+$): calcd. 385.2981, found 385.2976.

EXAMPLE 28

Preparation of 3-Hydroxy-2-methoxy-21-[2'-(N,N-dimethylamino)ethoxy]-19-norpregna-1,3,5(10)-triene (70)

The olefin 23 (50 mg, 0.125 mmol) was hydrogenated over 10% palladium on charcoal (15 mg) in 5 mL of ethanol at room temperature under atmospheric pressure overnight. The catalyst was removed by filtration and washed with ethanol. The solvent was removed in vacuo to give a white solid. Flash chromatography (5% methanol/chloroform) yielded amine 70 as a white solid (0.041 g, 82%): $^1$H NMR (300 MHz, CDCl$_3$): δ0.63 (s, 3, CH$_3$), 2.31 (s, 6, N(CH$_3$)$_2$), 2.54 (t, J=5.8 Hz, 2), 2.77 (m, 2), 3.46 (m, 2), 3.55 (m, 2) 3.85 (s, 3, OCH$_3$), 6.63 (s, 1, ArH), 6.80 (s, 1, ArH), HRMS for C$_{25}$H$_{39}$NO$_3$ (M$^+$): calcd. 401.2930, found 401.2940.

EXAMPLE 29

Preparation of 3-Hydroxy-7α-methyl-21-[2'-(N,N-dimethylamino)ethoxy]-19-norpregna-1,3,5(10)-triene (71)

The olefin 25 (1.01 mg, 2.68 mmol) was hydrogenated over 10% palladium on charcoal (380 mg) in 50 mL of ethanol at room temperature under atmospheric pressure overnight. The catalyst was removed by filtration and washed with ethanol. The solvent was removed in vacuo to give a white solid. Flash chromatography (10% ethanol/chloroform) yielded amine 71 as a white solid (0.90 g, 81%): $^1$H NMR (300 MHz, CDCl$_3$): δ0.62 (s, 3, CH$_3$), 0.84 (d, J=7.1 Hz, 3, CH$_3$), 1.09 (t, J=7.1 Hz, 6, N(CH$_2$CH$_3$), 2.69 (m, 6), 3.02 (m, 1) 3.47 (m, 2), 6.52 (d, J=2.7 Hz, 1 ArH), 6.62 (dd, J=2.7, 8.0 Hz, 1, ArH), 7.16 (d, J=8.0 Hz, 1, ArH).

EXAMPLE 30

Preparation of 21-(2'-N,N-Dimethylaminoethoxy)-[17(20)E]-19-norpregna-1,3,5(10),18(20)-tetraene-3-O-sulfamate (72)

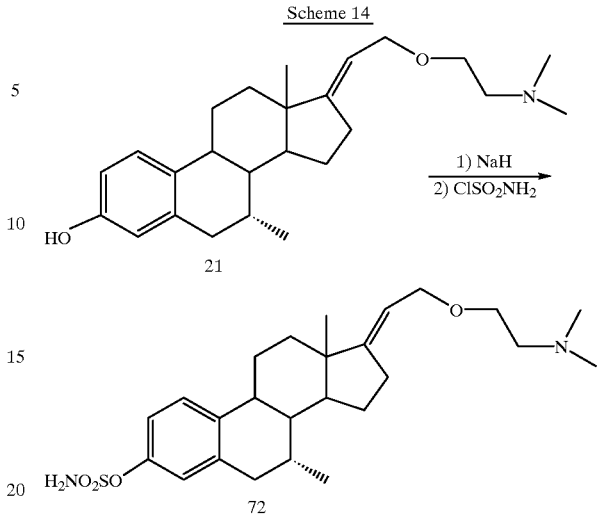

Scheme 14

To a solution of chlorosulfonyl isocyanate (0.14 mL, 1.5 mmol) in CH$_2$Cl$_2$ (0.6 mL) was added formic acid (0.3 mL of a CH$_2$Cl$_2$ solution, 5.0 M, 1.5 mmol) at 0° C. The reaction mixture was warmed to room temperature and stirred for 1 h. To a solution of 21-(2'-N,N-dimethylaminoethoxy)-[17(20)E]-19-norpregna-1,3,5(10),17(20)-tetraen-3-ol (21, 0.111 g, 0.3 mmol) in DMF (2.0 mL) was added sodium hydride (0.060 g of a mineral oil dispersion, 60%, 1.5 mmol) at 0° C. The reaction mixture was stirred for 1 h, and the chlorosulfonyl isocyanate in formic acid was added, and stirring continued for 2 h. The reaction mixture was quenched with saturated aqueous NaHCO$_3$ at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using CHCl$_3$:MeOH (10:1–5:1, v/v) to afford 0.121 g of 72 (90% yield) mp: 147–148° C.

$^1$H NMR: δ7.30 (d, 1H, aromatic), 7.13–7.00 (m, 2H, aromatic), 5.30–5.18 (m, 1H, =CH—CH$_2$O—), 4.05–3.90 (m, 2H, =CH—CH$_2$O—), 3.53 (t, 2H, —OCH$_2$CH$_2$N—), 2.55 (t, 2H, —OCH$_2$CH$_2$N—), 2.30 (s, 6H, —N(CH$_3$)$_2$), 0.78 (s, 3H, 18-CH$_3$); MS (DCI): m/z 449 (M$^+$+H).

EXAMPLE 31

Compound 75, an anti-estrogenic agent of the invention, was prepared using the individual reaction steps illustrated in Scheme 15, and analogous reagents and reaction conditions for the synthesis described in Example 32.

Scheme 15

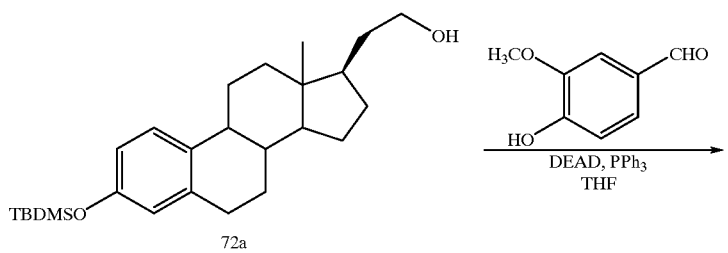

-continued

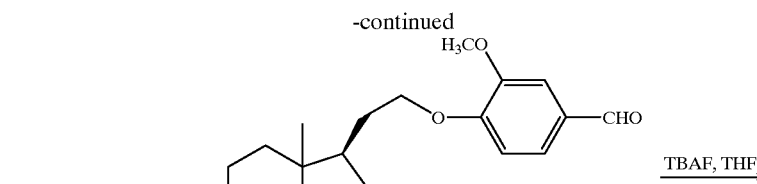

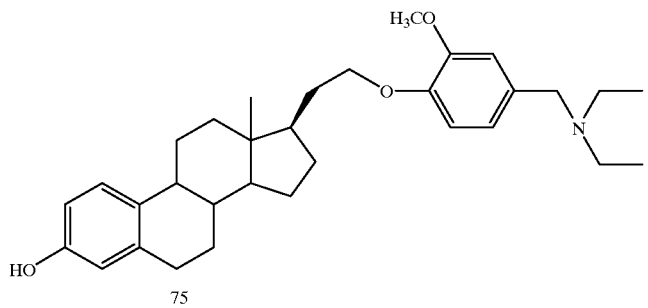

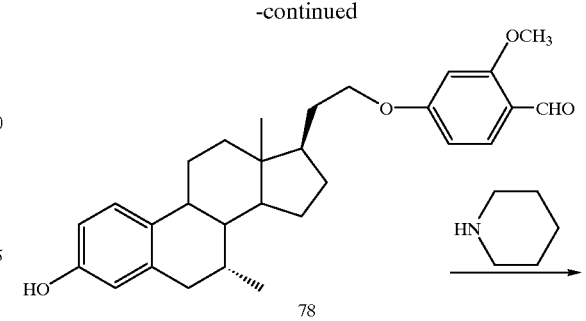

EXAMPLE 32

This example describes synthesis of compound 80, citric acid salt of 79, as illustrated in Scheme 16:

Scheme 16

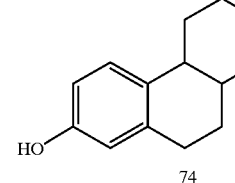

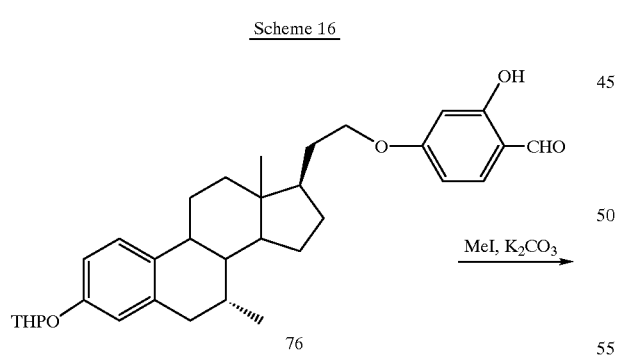

-continued

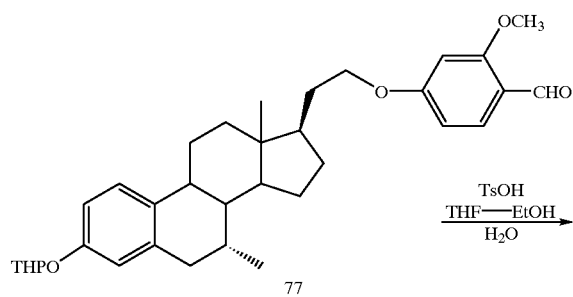

(a) Synthesis of 2-Hydroxy-4-[3'-tetrahydropyranyloxy-7'α-methyl-19'-norpregna-1',3',5'(10')trien-21'-yloxy] benzaldehyde (76): Aldehyde 76 was prepared from the corresponding alcohol (1.20 g, 3.02 mmol) and 2,4-dihydroxy-benzaldehyde (0.417 g, 3.02 mmol), and was obtained as an amorphous solid (1.01 g, 65%): $^1$H NMR δ0.67 (s, 3H), 0.85 (d, 3H, J=7.1 Hz), 4.05 (m, 2H), 5.38 (m, 1H), 6.42 (d, 1H, J=2.3 Hz, ArH), 6.53 (dd, 1H, J=8.7 Hz, 2.3 Hz, ArH), 6.78 (d, 1H, J=2.4 Hz, ArH), 6.85 (dd, 1H, J=8.8 Hz, 2.4 Hz, ArH), 7.21 (d, 1H, J=8.7 Hz), 7.43 (d, 1H, J=8.8 Hz), 9.7 (s, 1H).

(b) Synthesis of 2-Methoxy-4-[3'-tetrahydropyranaloxy-7'α-methyl-19'-norpregna-1',3',5'(10')-trien-21'-yloxy] benzaldehyde (77): To a solution of 76 (1.01 g, 1.95 mmol) in acetone (20 mL) was added anhydrous $K_2CO_3$ (690 mg, 5.0 mmol) and iodomethane (1.03 g, 7.25 mmol), and the mixture was stirred continuously for 2 days at room temperature. The reaction mixture was quenched with $H_2O$, extracted with ethyl acetate, washed with brine, dried over anhydrous $MgSO_4$, filtered, concentrated, and purified by chromatography (14% ethyl acetate/hexanes) to afford the benzaldehyde (77) as an amorphous solid (780 mg, 75%): $^1$H NMR δ0.67 (s, 3H), 0.85 (d, 3H, J=6.2 Hz), 3.90 (s, 3H), 4.05 (m, 2H), 5.38 (m, 1H), 6.42 (d, 1H, J=2.2 Hz, ArH), 6.53 (dd, 1H, J=8.6 Hz, 2.2 Hz, ArH), 6.78 (d, 1H, J=2.5 Hz, ArH), 6.85 (dd, 1H, J=8.6 Hz, 2.5 Hz, ArH), 7.21 (d, 1H, J=8.6 Hz), 7.43 (d, 1H, J=8.6 Hz), 10.29 (s, 1H).

(c) Synthesis of 2-Methoxy-4-[3'-hydroxy-7'α-methyl-19'-norpregna-1',3',5'(10')-trien-21'-yloxy]benzaldehyde (78): Benzaldehyde 78 was prepared from ether 77 (770 mg, 1.45 mmol); recrystallization from ethyl acetate-hexanes gave 78 as a crystalline solid (555 mg, 85%): m.p. 160–161° C.; $^1$H NMR δ0.68 (s, 3H), 0.85 (d, 3H, J=7.1 Hz), 2.50 (d, 1H, J=16.5 Hz), 3.05 (dd, 1H, J=16.5 Hz, 5.5 Hz), 3.90 (s, 3H), 4.00–4.13 (m, 2H), 4.95 (br, 1H, OH), 6.43 (d, 1H, J=2.1 Hz, ArH), 6.53 (dd, 1H, J=8.4 Hz, 2.1 Hz, Arh), 6.55 (d, 1H, J=2.7 Hz, ArH), 6.63 (1H, J=8.7 Hz, 2.7 Hz, ArH), 7.16 (d, 1H, J=8.4 Hz, ArH), 7.82 (d, 1H, J=8.7 Hz, ArH), 10.28 (s, 1H).

(d) Synthesis of 3-Hydroxy-7α-methyl-21-[3'-methoxy-4'-(piperidinomethyl)-phenoxy]-19-norpregna-1,3,5(10)-triene (79): Amine 79 was prepared from benzaldehyde 78 (550 mg, 1.23 mmol) and piperidine (136 mg, 1.60 mmol); recrystallization from MeOH gave 79 as a crystalline solid (560 mg, 88%): m.p. 200–202° C.; $^1$H NMR δ0.67 (s, 3H), 0.85 (d, 3H, J=7.0 Hz), 2.50 (br, 4H), 3.04 (dd, 1H, J=16.6 Hz, 5.5 Hz), 3.53 (s, 2H), 3.74 (s, 3H), 3.90–4.02 (m, 2H), 6.40–6.55 (m, 4H, ArH), 7.12 (d, 1H, J=8.3 Hz, ArH), 7.22 (d, 1H, J=8.8 Hz, ArH).

(e) Preparation of the citrate salt of 3-Hydroxy-7α-methyl-21-[3'-methoxy4'-(piperidinomethyl)phenoxy]-19-norpregna-1,3,5(10)-triene (80): To a solution of amine 79 (517 mg, 1.0 mmol) in 15 mL of MeOH at room temperature under argon was added citric acid (192 mg 1.0 mmol) and the reaction stirred for 10 min. The solvent was evaporated under reduced pressure and dried under vacuum to afford the citrate salt (80) as an amorphous solid in quantitative yield: $^1$H NMR δ0.68 (s, 3H), 0.82 (d, 3H, J=7.1 Hz), 2.45 (d, 1H, J=16.5 Hz), 2.73 (d, 2H, J=15.4 Hz), 2.83 (d, 2H, J=15.4 Hz), 3.00 (dd, 1H, J=16.5 Hz, 5.5 Hz), 3.86 (s,3H), 3.98–4.12 (m, 2H), 4.18 (s, 2H), 6.47 (d, 1H, J=2.5 Hz, ArH), 6.52–6.62 (m, 3H, ArH), 7.07 (d, 1H, J=8.3 Hz, ArH), 7.33 (d, 1H, J=8.2 Hz, ArH).

EXAMPLES 33–36

In this example, synthesis of compounds 81, 82, 83 and 84 is described. The synthesis is illustrated in Scheme 17, as follows:

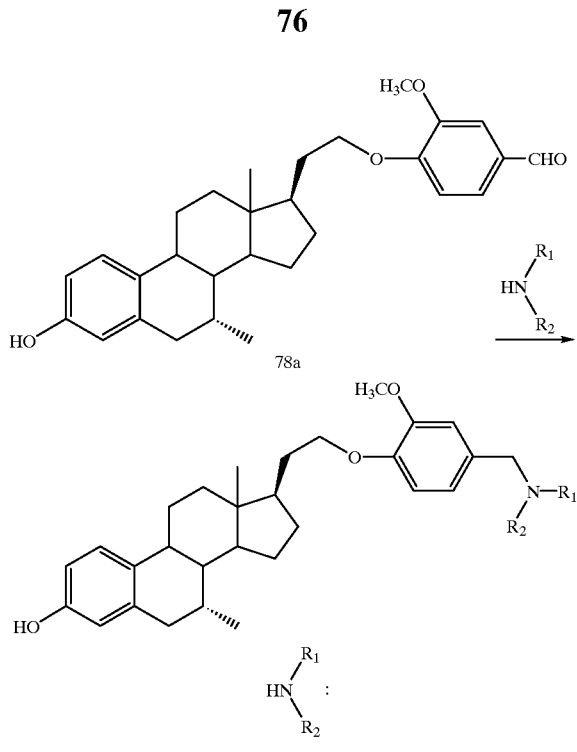

EXAMPLE 33

Compound 81:

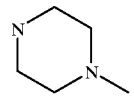

EXAMPLE 34

Compound 82:

EXAMPLE 35

Compound 83:

EXAMPLE 36

Compound 84:

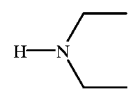

Scheme 17

Compounds 81, 82, 83 and 84 were prepared in a manner analogous to that described with respect to preparation of compound 79 from compound 78 in the preceding example. Briefly, the compounds were synthesized and characterized as follows:

4-[3'-Hydroxy-7'α-methyl-19'-norpregna-1',3',5'(10')-trien-21'-yloxy]-3-methoxy-benzaldehyde (78a): Ether 78a was prepared from the corresponding alcohol (2-hydroxyethyl substituent at the 17β-position) and vanillin (382 mg, 2.51 mmol), and was obtained as a crystalline solid (785 mg 66%). Recrystallization gave pure 78a: m.p. 163–164° C.; $^1$H NMR δ0.67 (s, 3H, 0.84 (d, 3H, J=7.0 Hz), 2.50 (d, 1H, J=16.5 Hz), 3.05 (dd, 1H, J=16.5 Hz, 5.5 Hz), 3.93 (s, 3H), 4.06–4.20 (m, 2H), 5.12 (br, 1H, OH), 6.55 (d, 1H, J=2.5 Hz, ArH), 6.63 (dd, 1H, J=8.4 Hz, 2.5 Hz, ArH), 6.98 (d, 1H, J=8.0 Hz, ArH), 7.15 (d, 1H, J=8.4 Hz, ArH), 7.42–7.48 (m, 2H), 9.85 (s, 1H); MS (DCI) 449 (M+H). HRMS for $C_{29}H_{36}O_4$(M+H)$^+$ calcd., 449.2692; found, 449.2689. (M+NH$_4$)$^+$ calcd., 466.2957; found, 466.2976.

3-Hydroxy-7α-methyl-21-[2'-methoxy-4'-(4"-methylpiperazinomethyl)phenoxy]-19-norpregna-1,3,5(10)-triene (81): Amine 81 was prepared from benzaldehyde 78a (50 mg, 0.112 mmol) and 1-methylpiperazine (0.018 mL, 0.16 mmol); recrystallization from MeOH gave 81 as a crystalline solid (22 mg 37%): m.p. 214–215° C.; $^1$H NMR δ0.66 (s, 3H), 0.84 (d, 3H, J=7.0 Hz), 2.29 (s, 3H), 2.45–2.56 (m, 9H), 3.05 (dd, 1H, J=17.0 Hz, 6.0 Hz), 3.45 (s, 2H), 3.85 (s, 3H), 3.95–4.08 (m, 2H), 6.52 (d, 1H, J=2.6 Hz, ArH), 6.60 (dd, 1H, J=8.6 Hz, 2.6 Hz, ArH), 6.80 (s, 2H, ArH), 6.89 (s, 1H, ArH), 7.16 (d, 1H, J=8.6 Hz, ArH).

3-Hydroxy-7α-methyl-21-[2'-methoxy-4'-(pyrrolidinomethyl)phenoxy]-19-norpregna-1,3,5(10)-triene (82): Amine 82 was prepared from benzaldehyde 78a (600 mg, 1.34 mmol) and pyrrolidine (0.15 mL, 1.8 mmol); recrystallization from MeOH gave 82 as a crystalline solid (450 mg, 67%): m.p. 192–193° C.; $^1$H NMR δ0.65 (s, 3H), 0.84 (d, 3H, J=7.1 Hz), 2.45 (d, 1H, J=16.5 Hz), 2.57 (m, 4H), 3.02 (dd, 1H, J=16.5 Hz, 6.0 Hz), 3.58 (s, 2H), 3.77 (s, 3H), 3.92–4.06 (m, 2H), 6.47 (d, 1H, J=2.6 Hz, ArH), 6.52 (dd, 1H, J=8.4 Hz, 2.6 Hz, ArH), 6.77–6.83 (m, 2H, ArH), 6.90 (d, 1H, J=1.6 Hz), 7.11 (d, 1H, J=8.4 Hz, ArH).

3-Hydroxy-7α-methyl-21-[2'-methoxy-4'-(N,N-dimethylaminomethyl)phenoxy]-19-norpregna-1,3,5(10)-triene (83): Amine 83 was prepared from benzaldehyde 78 (60 mg, 0.134 mmol) and N,N-dimethylamine (0.08 mL, 0.16 mmol); recrystallization from MeOH gave 83 as a crystalline solid (40 mg, 62%): m.p. 186–187° C.; $^1$H NMR δ0.65 (s, 3H), 0.84 (d, 3H, J=7.0 Hz), 2.26 (s, 6H, N(C$\underline{H}_3$)$_2$), 2.46 (d, 1H, J=16.5 Hz,), 3.02 (dd, 1H, J=16.5 Hz, 6.0 Hz), 3.40 (s, 2H), 3.80 (s, 3H), 3.93–4.08 (m, 2H), 6.49 (d, 1H, J=2.6 Hz, ArH), 6.56 (dd, 1H, J=8.4 Hz, 2.6 Hz, ArH), 6.80 (s, 2H, ArH), 6.89 (s, 1H, ArH), 7.13 (d, 1H, J=8.4 Hz, ArH).

3-Hydroxy-7α-methyl-21-[2'-methoxy-4'-(N,N-diethylaminomethyl)phenyloxy]-19-norpregna-1,3,5(10)-triene (84): To a solution of the methoxybenzaldehyde analog 78a (0.500 g, 1.12 mmol) and diethylamine (155 μL, 1.5 mmol) in dry 1,2-dichloroethane (10 mL) under argon was added sodium triacetoxyborohydride (0.403 g 1.9 mmol). The cloudy solution was stirred for 18 h at room temperature. To the cloudy mixture was added saturated NaHCO$_3$ followed by extraction with ethyl acetate. The ethyl acetate was washed with saturated NaCl solution, dried over magnesium sulfate, filtered, and evaporated. The residue was crystallized from MeOH to afford 350 mg of 84 (62% yield): mp 123–124° C.; $^1$H NMR δ0.65 (s, 3H), 0.84 (d, 3H, J=7.0 Hz), 1.07 (t, 6H, J=7.1 Hz), 2.46 (d, 1H, J=16 Hz), 2.57 (q, 4H, J=7.1 Hz), 3.02 (dd, 1H, J=16.5 Hz), 3.55 (s, 3H), 3.81 (s, 3H), 3.92–4.08 (m, 2H), 6.48 (d, 1H, J=2.6 Hz, ArH) 6.56 (dd, 1H, J=8.4 Hz), 6.7–7.12 (m, 6H).

EXAMPLE 37

This example describes preparation of the citric acid salt 85 from the free base analog 84, as illustrated in Scheme 18:

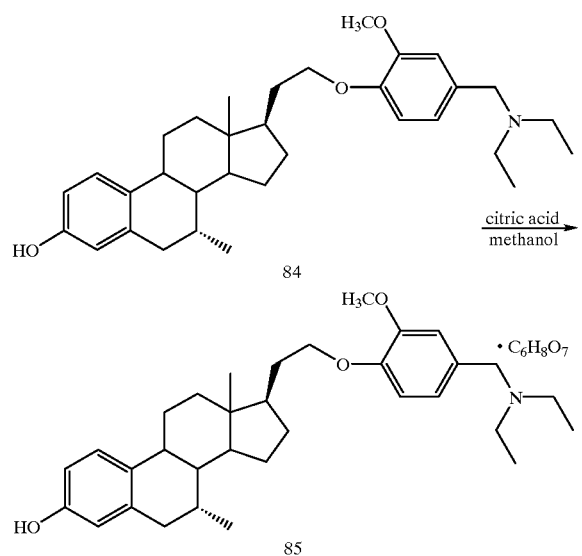

Citrate Salt of 3-Hydroxy-7α-methyl-21-[2'-methoxy-4'-(N,N-diethylaminomethyl)phenoxy]-19-norpregna-1,3,5 (10)-triene (85): To a solution of amine 84 (100 mg, 0.198 mmol) in 1 mL of hot EtOH under argon was added citric acid (38 mg, 0.188 mmol) and the reaction stirred for 10 min. Cooling gave a white crystalline solid that was filtered and dried to afford 120 mg (87% yield) of 85: mp 166° C. (decomposed); $^1$H NMR (CD$_3$OD) δ0.69 (s, 3H), 0.82 (d, 3H, J=7.0 Hz), 1.36 (t, 6H, J=7.2 Hz), 2.46 (d, 1H, J=16.5 Hz), 2.77 (q, 4H, J=7.2 Hz), 3.86 (s, 3H), 4.24 (s, 2H), 6.40–6.60 (m, 2H, ArH), 6.98–7.16 (m, 4H, ArH).

EXAMPLE 8

Compound 90 was synthesized as illustrated in Scheme 19.

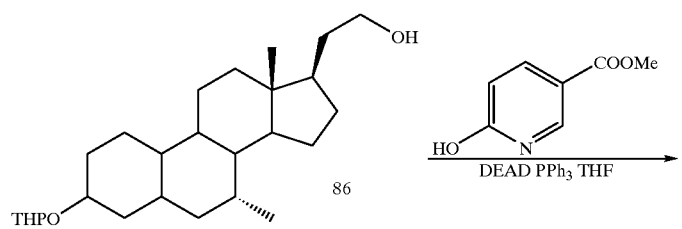

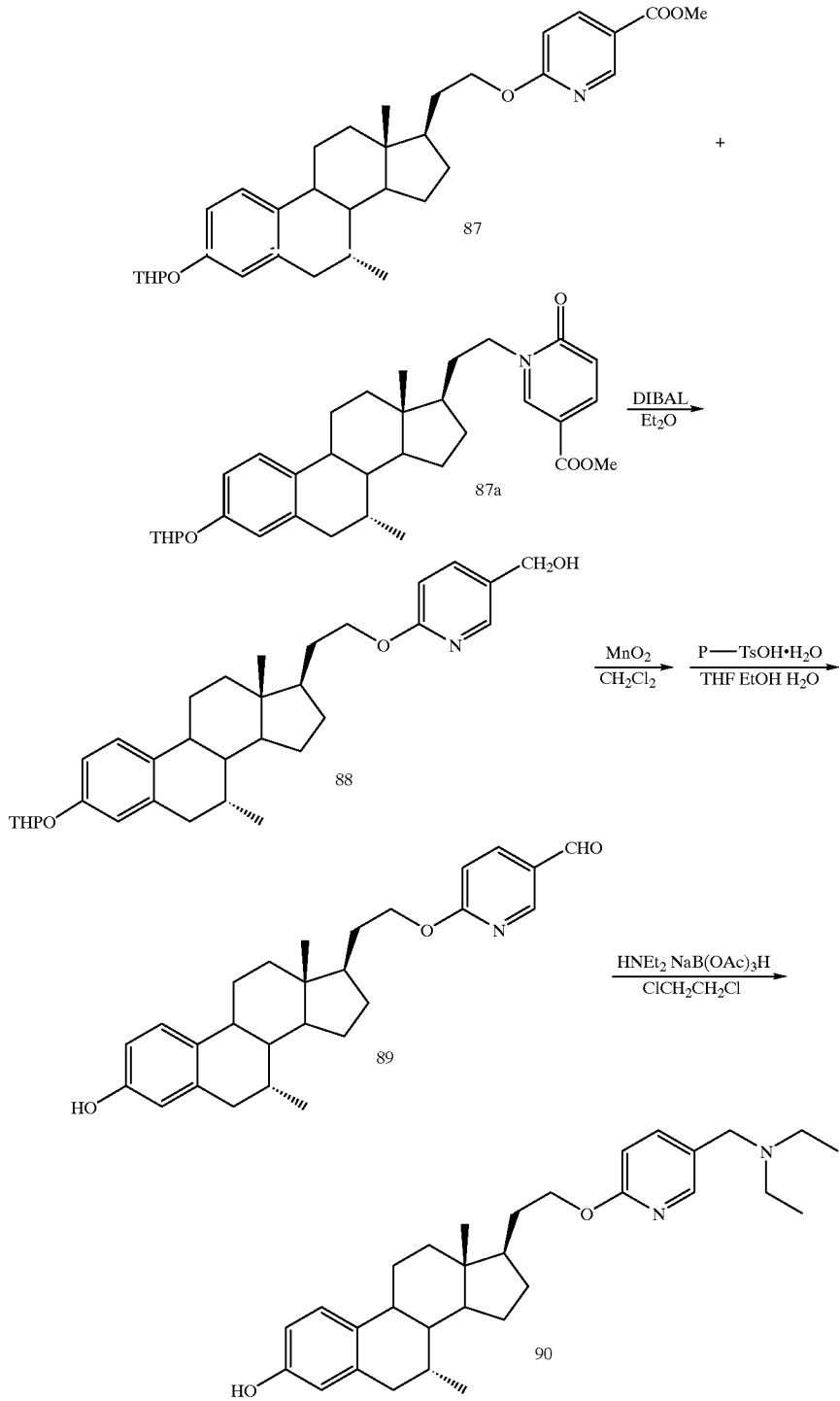

Preparation of (E)-3-Tetrahydropyranyloxy-7α-methyl-21-hydroxy-19-norpregna-1,3,5(10)-triene (86): To a solution of 33.5 g of 47b in 500 mL of THF at −78° C. was added 185 mL of 1.0 M diisobutylaluminum hydride in heptane. The reaction mixture was warmed to 0° C. and stirred at that temperature for 1.5 h. Methanol (15 mL) and H$_2$O (15 mL) were added at 0° C. and the solution was warmed to room temperature and stirred for 0.5 h. The cloudy suspension was poured into H$_2$O (1.4 L) and extracted with EtOAc (3×300 mL). The combined organic layers were washed with sat. NaCl, dried over MgSO$_4$, filtered, and evaporated to dryness to afford 29.31 g (97%) of 86 as a white solid. The remaining reaction steps, reagents and reaction conditions are analogous to those used in the preceding examples, Examples 31–37.

EXAMPLE 39

This example describes synthesis of compound 92 as illustrated in Scheme 20:

Scheme 20

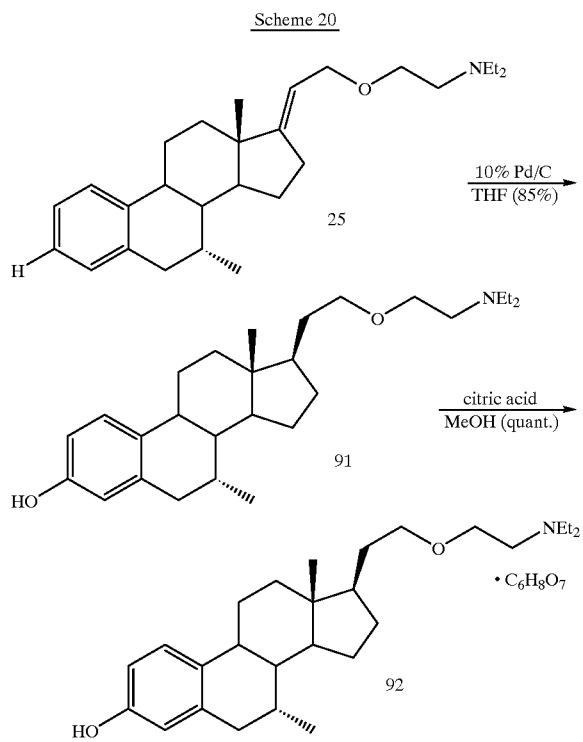

(a) Synthesis of 3-Hydroxy-7α-methyl-21-(2'-N,N-diethylaminoethoxy)-19-norpregna-1,3,5(10)-triene (91). Olefin 25 (18.88 g, 45.94 mmol) was hydrogenated over 10% Pd—C (7 g) in 300 mL of ethanol at room temperature under atmospheric pressure overnight. The catalyst was removed by filtration and washed with ethanol. The solvent was removed under vacuum. The residue was recrystallized from isopropyl ether to afford amine 91 as a crystalline solid (16.13 g, 85%): m.p. 106–107° C.; $^1$H NMR δ0.62 (s, 3H), 0.84 (d, 3H, J=7.1 Hz), 1.09 (t, 6H, N(CH$_2$CH$_3$)$_2$, J=7.2 Hz), 2.48 (d, 1H, J=16.5 Hz), 2.68 (q, 4H, N(CH$_2$CH$_3$)$_2$, J=7.2 Hz), 2.74 (t, 2H, J=6.3 Hz), 3.03 (dd, 1H, J=16.5 Hz, 6.1 Hz), 3.36–3.54 (m, 2H), 3.57 (t, 2H, J=6.3 Hz), 6.54 (d, 1H, J=2.6 Hz, ArH), 6.62 (dd, 1H, J=8.6 Hz, 2.6 Hz, ArH), 7.16 (d, 1H, J=8.6 Hz, ArH); MS (DCI) 414 (M+H).

(b) Citrate of 3-Hydroxy-7α-methyl-21-(2'-N,N-diethylaminoethoxy)-19-norpregna-1,3,5(10)-triene (92). To a solution of amine 91 (0.85 g, 2.06 mmol) in 40 mL of MeOH at room temperature under argon was added citric acid (0.395 g, 2.06 mmol), and stirring continued for 15 min. The solvent was evaporated under reduced pressure and dried under vacuum to afford the citrate salt 92 as an amorphous solid in quantitative yield. Analytical sample was prepared by crystallizing from EtOH: m.p. 106–107° C. (decomposed); $^1$H NMR (CD$_3$OD) δ0.65 (s, 3H), 0.82 (d, 3H, J=7.0 Hz), 1.31 (t, 6H, N(CH$_2$CH$_3$)$_2$, J=7.3 Hz), 2.43 (d, 1H, J=16.6 Hz), 2.67 (d, 2H, J=15.4 Hz), 2.82 (d, 2H, J=15.4 Hz), 2.99 (dd, 1H, J=16.6 Hz, 5.0 Hz), 3.26 (q, 4H, N(CH$_2$CH$_3$)$_2$, J=7.3 Hz), 3.31–3.35 (m, 2H), 3.50 (m, 2H), 3.73 (m, 2H), 6.46 (d, 1H, J=2.2 Hz, ArH), 6.53 (dd, 1H, J=8.7 Hz, 2.2 Hz, ArH), 7.16 (d, 1H, J=8.7 Hz, ArH); MS (DCI) 414 (M+H).

EXAMPLE 40

Bioassay for Measuring Estrogenic and Anti-estrogenic Activity of Test Compounds Using Human Ishikawa Cells A. Procedures Human Ishikawa cells are very sensitive to estrogens, and compounds with estrogenic activity induce alkaline phosphatase (AlkP) in these cells at levels as low as $10^{-12}$M. Therefore, the estrogenic activity of any target compound can be measured by quantifying AlkP activity induced by the compound.

Reagents: Human Ishikawa cells were provided by Dr. Erlio Gurpide (Mount Sinai School of Medicine, N.Y.). Eagle's minimum essential medium (MEM), fetal calf serum (FCS) and p-nitrophenyl phosphate were purchased from Sigma Chemical Company (St. Louis, Mo.).

Cell Culture: Human Ishikawa cells were routinely maintained in MEM containing 10% FCS and supplemented with 2 mM glutamine and 1 mM sodium pyruvate. Cells were seeded at a density of 1.5×10$^6$ cells/75 cm$^2$ and passaged twice weekly. Twenty-four h before starting an experiment, the medium in the near-confluent cell cultures was changed to phenol red-free MEM containing 5% FCS stripped of endogenous estrogens with dextran-coated charcoal plus the above-listed supplements.

Drug Treatment: On the day of the experiment, cells were harvested with 0.25% trypsin and plated in 96-well flat-bottomed microtiter plates in phenol red-free MEM at a density of 1.5×10$^4$ cells/well. Test compounds were dissolved in DMSO at $10^{-2}$ M, diluted appropriately with phenol red-free MEM (final DMSO concentration, 0.1%). The diluted test compounds were added to the culture wells either alone or in combination with $10^{-9}$M estradiol. Each experiment included a blank control (vehicle only) and a positive control ($10^{-9}$M) culture well. The final volume of medium in each culture well was 200 μL. After all additions, the cells were incubated at 37° C. in a humidified atmosphere containing 5% CO$_2$ for 72 h. At the end of the 72 h incubation period, the AlkP assay was performed.

AlkP Assay: The assay was performed by inverting microtiter plates and removing growth medium with a brisk shake of the wrist. The plates were rinsed by gently immersing and swirling them in 2L of PBS (0.15 M NaCl, 10 mM sodium phosphate, pH 7.4) in a 27 cm×10 cm×9.5 cm plastic container. The plates were removed from the container leaving the residual saline in each well, and the wash procedure was repeated once. Afterwards, the buffered saline was shaken from the plates and the plates were inverted and gently blotted on a paper towel. The plates were then placed on ice and 50 μL of ice-cold solution containing p-nitrophenyl phosphate (5 mM), MgCl$_2$ (0.24 mM) and diethanolamine (1M, pH 9.8) was added to each well. The plates were then warmed to room temperature and the yellow color from the production of p-nitrophenol was allowed to develop. Plates were monitored periodically at 405 nm in an enzyme-linked immunosorbent assay (ELISA) plate reader until such time as maximally-stimulated cells showed an absorbance of 1.2 at 405 nm. The estrogenic activity of a test compound is calculated as the percentage stimulation of AlkP activity (i.e., absorbance at 405 nm) by the test compound normalized to $10^{-9}$ M estradiol-stimulated activity (where absorbance of 1.2 at 405 nm=100% stimulation). The anti-estrogenic activity of a test compound is defined as the percent inhibition of $10^{-9}$ M estradiol-stimulated AlkP activity by the test compound.

B. Results

Representative anti-estrogenic compounds of this invention were evaluated for in vitro anti-estrogenic and estrogenic activity as described above. The results obtained with the test compounds are shown in Table 1 below. The results obtained with tamoxifen, 4-hydroxy-tamoxifen, DP-TAT-59, TAT-59 and ICI 164384 are also included.

TABLE 1

| Compound No. | Concentration | Estrogenic Activity Exp1 | Exp2 | Exp3 | Anti-Estrogenic Activity Exp1 | Exp2 | Exp3 |
|---|---|---|---|---|---|---|---|
| 6 | 10 nM | 3 | | | 0 | | |
|  | 100 nM | 1 | | | 4 | | |
|  | 1 μM | 10 | | | 19 | | |
| 7 | 10 nM | 15 | | | 19 | | |
|  | 100 nM | 0 | | | 5 | | |
|  | 1 μM | 0 | | | 64 | | |
| 8 | 10 nM | 15 | | | 12 | | |
|  | 100 nM | 10 | | | 31 | | |
|  | 1 μM | 5 | | | 57 | | |
| 9 | 10 nM | 6 | | | 18 | | |
|  | 100 nM | 16 | | | 25 | | |
|  | 1 μM | 13 | | | 58 | | |
| 10 | 10 nM | 4 | | | 0 | | |
|  | 100 nM | 14 | | | 0 | | |
|  | 1 μM | 4 | | | 49 | | |
| 11 | 10 nM | 32 | | | 0 | | |
|  | 100 nM | 27 | | | 17 | | |
|  | 1 μM | 23 | | | 38 | | |
| 12 | 10 nM | 3 | | | 0 | | |
|  | 100 nM | 6 | | | 2 | | |
|  | 1 μM | 12 | | | 24 | | |
|  | 10 μM | 0 | | | 100 | | |
| 21 | 1 nM | | 0 | 0 | | 9 | 7 |
|  | 10 nM | 0 | 0 | 0 | 38 | 22 | 23 |
|  | 100 nM | 0 | 0 | 1 | 40 | 28 | 30 |
|  | 1 μM | 0 | 0 | 0 | 63 | 68 | 55 |
|  | 10 μM | | 0 | 0 | | 100 | 100 |
| 22 | 10 nM | 0 | | | 0 | | |
|  | 100 nM | 0 | | | 76 | | |
|  | 1 μM | 0 | | | 100 | | |
| 23 | 10 nM | 1 | | | 4 | | |
|  | 100 nM | 1 | | | 15 | | |
|  | 1 μM | 0 | | | 30 | | |
| 24 | 10 nM | 0 | | | 10 | | |
|  | 100 nM | 0 | | | 3 | | |
|  | 1 μM | 0 | | | 51 | | |
| 25 | 10 nM | 0 | 0 | | 2 | 0 | |
|  | 100 nM | 0 | 0 | | 39 | 50 | |
|  | 250 μM | | 0 | | | 70 | |
|  | 500 μM | | 0 | | | 87 | |
|  | 1 μM | 0 | 0 | | 100 | 100 | |
| 27 | 10 nM | 0 | 1 | 0 | 35 | 0 | 1 |
|  | 100 nM | 0 | 4 | 0 | 65 | 0 | 17 |
|  | 1 μM | 0 | 0 | 0 | 95 | 56 | 81 |
| 32 | 1 nM | 0 | | | 14 | | |
|  | 10 nM | 0 | | | 9 | | |
|  | 100 nM | 2.5 | | | 9 | | |
|  | 1 μM | 1 | | | 56 | | |
| 35 | 10 nM | 2 | | | 0 | | |
|  | 100 nM | 1 | | | 0 | | |
|  | 1 μM | 0 | | | 48 | | |
| 36 | 10 nM | 3 | | | 0 | | |
|  | 100 nM | 5 | | | 0 | | |
|  | 1 μM | 20 | 0 | | 45 | 56 | |
| 48 | 10 nM | 0 | | | 0 | | |
|  | 100 nM | 0 | | | 66 | | |
|  | 1 μM | 0 | | | 100 | | |
| 50 | 10 nM | 0 | 0 | | 30 | 33 | |
|  | 100 nM | 0 | 0 | | 100 | 68 | |
|  | 1 μM | 0 | 0 | | 100 | 100 | |
|  | 5 μM | 0 | 0 | | 100 | 100 | |
| 51 | 10 nM | 0 | | | 5 | | |
|  | 100 nM | 0 | | | 46 | | |
|  | 1 μM | 0 | | | 100 | | |
|  | 5 μM | 0 | | | 100 | | |
|  | 10 μM | 0 | | | 100 | | |
| 59 | 10 nM | 0 | | | 24 | | |
|  | 100 nM | 0 | | | 47 | | |
|  | 500 nM | 0 | | | 76 | | |
| 65 | 1 μM | 0 | | | 100 | | |
|  | 10 nM | 0 | | | 29 | | |
|  | 100 nM | 0 | | | 14 | | |
| 66 | 1 nM | 0 | | | 49 | | |
|  | 10 nM | 0 | | | 30 | 7 | |
|  | 100 nM | 0 | 0 | | 21 | 7 | |
|  | 1 μM | 0 | 0 | | 78 | 81 | |
|  | 2 μM | | 0 | | | 89 | |
|  | 5 μM | | 0 | | | 100 | |
| 67 | 10 nM | 11 | | | 0 | | |
|  | 100 nM | 25 | | | 0 | | |
|  | 500 nM | 7 | | | 48 | | |
|  | 1 μM | 7 | | | 67 | | |
| 68 | 10 nM | 6 | | | 0 | | |
|  | 100 nM | 16 | | | 0 | | |
|  | 500 nM | 3 | | | 31 | | |
|  | 1 μM | 6 | | | 59 | | |
| 70 | 1 nM | 0 | | | 10 | | |
|  | 10 nM | 0 | | | 18 | | |
|  | 100 μM | 0 | | | 3 | | |
|  | 1 μM | 9 | | | 32 | | |
| 71 | 1 nM | 0 | | | 1 | | |
|  | 10 nM | 0 | | | 9 | | |
|  | 100 nM | 0 | | | 79 | | |
|  | 1 μM | 0 | | | 100 | | |
| 72 | 10 nM | 40 | | | 0 | | |
|  | 100 nM | 62 | | | 0 | | |
|  | 1 μM | 40 | | | 54 | | |
| 79 | 10 nM | 0 | | | 0 | | |
|  | 100 nM | 0 | | | 35 | | |
|  | 1 μM | 0 | | | 100 | | |
| 83 | 1 nM | 0 | | | 3 | | |
|  | 10 nM | 0 | | | 40 | | |
|  | 100 nM | 0 | | | 100 | | |
|  | 1 μM | 0 | | | 100 | | |
| 84 | 1 nM | 0 | | | 23 | | |
|  | 10 nM | 0 | | | 64 | | |
|  | 100 nM | 0 | | | 100 | | |
|  | 1 μM | 0 | | | 100 | | |
| 85 | 1 nM | 0 | | | 41 | | |
|  | 10 nM | 0 | | | 70 | | |
|  | 100 nM | 0 | | | 100 | | |
|  | 1 μM | 0 | | | 100 | | |
| 91 | 1 nM | 0 | | | 1 | | |
|  | 10 nM | 0 | | | 9 | | |
|  | 100 nM | 0 | | | 79 | | |
|  | 1 μM | 0 | | | 100 | | |
| 92 | 1 nM | 0 | | | 0 | | |
|  | 10 nM | 0 | | | 2 | | |
|  | 100 nM | 0 | | | 91 | | |
|  | 1 μM | 0 | | | 100 | | |
| 96 | 10 nM | 0 | | | 0 | | |
|  | 100 nM | 7 | | | 0 | | |
|  | 1 μM | 8 | | | 42 | | |
| 102 | 1 nM | 0 | | | 0 | | |
|  | 10 nM | 0 | | | 2 | | |
|  | 100 nM | 0 | | | 48 | | |
|  | 1 μM | 0 | | | 100 | | |
| 103 | 1 nM | 0 | | | 0 | | |
|  | 10 nM | 0 | | | 0 | | |
|  | 100 nM | 0 | | | 66 | | |
|  | 1 μM | 0 | | | 100 | | |
| 104 | 1 nM | 0 | | | 0 | | |
|  | 10 nM | 0 | | | 0 | | |
|  | 100 nM | 0 | | | 16 | | |
|  | 1 μM | 0 | | | 100 | | |
|  | 10 μM | 0 | | | 100 | | |
| 105 | 10 nM | 1 | | | 5 | | |
|  | 100 nM | 3 | | | 73 | | |
|  | 1 μM | 0 | | | 100 | | |
| Tamoxifen | 10 nM | 15 | | | 0 | | |
|  | 100 nM | 23 | | | 0 | | |
|  | 1 μM | 15 | | | 31 | | |
| 4-OH- | 10 nM | 7 | | | 31 | | |

TABLE 1-continued

| Compound | | Estrogenic Activity | | | Anti-Estrogenic Activity | | |
|---|---|---|---|---|---|---|---|
| No. | Concentration | Exp1 | Exp2 | Exp3 | Exp1 | Exp2 | Exp3 |
| Tamoxifen | 100 nM | 9 | | | 85 | | |
| | 1 µM | 10 | | | 90 | | |

EXAMPLE 41

Uterotrophic and Antiuterotrophic Assay

Assay Procedure: Female Sprague Dawley rats (obtained from Simmonsen Laboratories (Gilroy, Calif.) weighing 40–50 g were used for the experiment. To start the experiment, the rats were weighed and randomly divided into groups of 5 animals. For the uterotrophic assay, various doses of test compounds in sterile saline (0.1 ml for subcutaneous injection, 1.0 ml for oral gavage) were administered to the animals once a day. The same procedure was used for the antiuterotrophic assay, but a suspension of 0.5 µg estradiol benzoate (obtained from the Sigma Chemical Co., St. Louis, Mo.) in vehicle was also administered orally to each of the test animals. Each experiment included two control groups, one for receiving a vehicle alone and the other for receiving estradiol benzoate alone.

The treatments were carried out for 3 days. On day 4, the animals were weighed and then sacrificed. The uteri were immediately removed from the animals, trimmed of fat, and then weighed.

Estrogenic activity was determined from the uterine weights in groups receiving test compound alone compared with those of the vehicle control group. Anti-estrogenic activity was determined from the uterine weights in groups receiving test compound plus estradiol compared with those of the estradiol control group.

TABLE 2

ANTIUTEROTROPHIC ACTIVITY OF ANTIESTROGENS

| Compound | Route | Dose (mg/kg) | Uterotrophic Activity (%) | Antiuterotrophic Activity (%) |
|---|---|---|---|---|
| 21 | oral | 0.02 | 1 | |
| | oral | 0.2 | 0 | |
| | oral | 2.0 | 0 | |
| 21, citric salt | s.c.* | 0.02 | | 60 |
| | s.c. | 2 | | 60 |
| | oral | 0.02 | | 58 |
| | oral | 2 | | 91 |
| 72 | s.c. | 0.02 | | 47 |
| | s.c. | 2 | | 70 |
| | oral | 0.02 | | 37 |
| | oral | 2 | | 25 |
| 85 | oral | 50 | −3.5 | 102.9 |
| | oral | 5 | −2.9 | 95.2 |
| | oral | 0.5 | 4.2 | 87.8 |
| | oral | 0.05 | −3.5 | 61.2 |
| | oral | 0.005 | −11.5 | 26.9 |
| 92 | oral | 50 | 18.7 | 85.2 |
| | oral | 5 | 6.8 | 87.6 |
| | oral | 0.5 | −0.5 | 61.2 |
| | oral | 0.05 | 3.2 | 24.5 |
| | oral | 0.005 | −10.7 | −6.8 |
| ICI 164,384 | s.c. | 0.02 | | 100 |
| | s.c. | 2 | | 100 |
| | oral | 0.02 | | 72 |
| | oral | 2 | | 45 |

*s.c. = subcutaneous.

EXAMPLE 42

Evaluation of Tissue Selectivity

The tissue-specific estrogenicity of compounds 85 and 92 was evaluated in comparison with tamoxifen and raloxifene. Sprague-Dawley rats (seven weeks old) purchased from SLC Inc. (Shizuoka) and fed with TD89222 were used for this experiment. Two weeks after purchase, the rats were ovariectomized or sham-operated under light ether anesthesia. One week after ovariectomy, the rats were randomly divided into 21 groups of 9 animals (day 0) and treated orally with the selected drug from day 0 to day 28. On the day following the final dose, the rats were sacrificed and their femurs, uteri, blood and urine were collected.

The dissected right femurs were weighed and their volumes were determined by Archimides' principle. The dry weights were determined after treatment of femurs at 110° C. for 5 days and the ash was weighed after treatment at 900° C. for 5 hrs. Gross bone density was calculated by dividing femur weight by volume and mineral content was estimated by dividing ash weight by dry weight.

The left femurs were subjected for determination of trabecular density and polar strength using peripheral quantitative computed tomography (XCT-906A, Norland, N.Y.). A 3-mm to 5.5-mm section distal to the growth plate of femur was analyzed.

Pyridinium cross-links levels in urine samples were determined by Pyrilinks (Metra Bosystems Inc., CA) and adjusted by creatinine levels.

Serum alkaline phosphatase levels were analyzed by ALP-HA (Wako, Osaka). Serum cholesterol levels were determined by HDL-CIL/PM (Wako pur chemicals, Osaka) and cholestest LDL (Daiichi pure chemicals, Tokyo).

Results:

All compounds prevented the loss of trabecular bone density of ovariectomized rats (FIG. 1). After 4 weeks treatment, the trabecular bone density of the ovariectomized rats was significantly deceased in comparison with the sham-operated rat ($p<0.01$) and that of compound 92-, tamoxifen- or raloxifene-treated rats was significantly higher than that of ovariectomized rats ($p<0.05$). Urinary pyridinium-cross-links levels, as a marker of absorption of bone, in the rats treated with antiestrogens were significantly lower than that in the ovariectomized rats, after 4 weeks treatment, suggesting the suppression of osteolysis by estrogenic activity of compounds (FIG. 2). Serum levels of both total and bone-derived alkaline phosphatase of the rats treated with compound 92 were significantly higher than that of control rats (FIG. 3).

Similar results are expected with structurally analogous compounds disclosed and claimed herein.

EXAMPLE 43

In vivo Antitumor Testing Against MCF-7 Human Mammary Tumor Xenograft and its Tamoxifen-Resistant Cell Line The antitumor activity of compounds 85 and 92 against tamoxifen-resistant human mammary carcinoma was evaluated as follows.

Compounds 85, 92, tamoxifen and raloxifene were suspended in 0.5% hydroxypropylmethyl-cellulose solution; faslodex was dissolved in arachis oil. MCF-7 human mammary carcinoma cells and its tamoxifen-resistant subline, FST-1 cells, were used. Eight $mm^3$ fragments of tumor were subcutaneously inoculated into the right flank of female BALB/c (nu/nu) mice (Japan Clea Inc.). The pellet containing 500 μg/pellet of estradiol was used for estrogen supplementation. When tumors reached a diameter of 6 to 7 mm (two to three weeks after inoculation), mice were given compounds 85 (some 10 mg/kg/day, some 30 mg/kg/day), 92 (doses of 1 mg/kg/day, 5 mg/kg/day, 25 mg/kg/day, 1 mg/kg/day), tamoxifen (10 mg/kg/day) or raloxifene (50 mg/kg/day) daily for 3 to 4 weeks, administered orally, or were given faslodex subcutaneously (5 mg/mouse/week), weekly, for 3 weeks. The size of tumors was recorded following palpation, using two perpendicular diameters.

Results:

With respect to the MCF-7 tumor, all compounds showed a significant growth-suppressive activity. Ten mg/kg/day of compound 85 and 25 mg/kg/day of compound 92 showed the strongest growth inhibitory activity, followed by 5 mg/body of faslodex, 10 mg/kg/day of tamoxifen, and 50 mg/kg/day of raloxifene.

With the FST-1 tumor, no growth suppression was observed with tamoxifen, indicating that FST-1 maintained its tamoxifen resistance. Ten mg/kg/day of compound 85 and 25 mg/kg/day of compound 92 showed a significant growth suppressive activity against the FST tumor. Complete suppression of tumor growth was in fact achieved with compound 92. In this system, 50 mg/kg/day of raloxifene failed to show growth-suppressive activity and faslodex was found to be less effective than compound 85.

EXAMPLE 44

Evaluation of Compounds of the Invention to Treat Women Suffering from Dysfunctional Uterine Bleeding At least five women are selected for the clinical study. The women suffer from dysfunctional uterine bleeding. Because of the idiosyncratic and subjective nature of these symptoms, the study has a placebo control group, i.e., the women are divided into two groups, one of which receives a compound of the invention such as compound 85 or 92, and the other of which receives a placebo. The patients are evaluated as to the character of their dysfunctional uterine bleeding (blood loss, timing, etc.) prior to the study's initiation. Evaluations may also include uterine biopsy "estrogenicity scores" by histological assessment, and ultrasonic, radio imaging, NMR, or CAT scan evaluations of endometrial thickness. Women in the test group receive between 30–600 mg of the drug per day by the oral route. They continue this therapy for 3–12 months. Accurate records are kept as to the status of their dysfunctional uterine bleeding in both groups and at the end of the study these results are compared. The results are compared both between members of each group and also the results for each patient are compared to the symptoms reported by each patient before the study began. Utility of the compounds of the invention is illustrated by the therapeutic effect they have on the patients' dysfunctional uterine bleeding.

EXAMPLE 45

Evaluation of the Compounds of the Invention to Inhibit Estrogen-Dependent CNS Disorders in Postmenopausal Women Five to fifty women are selected for the clinical study. The women are postmenopausal, i.e., have ceased menstruating for between 6 and 12 months prior to the study's initiation, are in good general health, and suffer from a CNS disorder, i.e., anxiety, depression, mood swings, tension, irritability, motivational defects, memory loss or a cognitive disorder. Because of the idiosyncratic and subjective nature of these disorders, the study has a placebo control group, i.e., the women are divided into two groups, one of which receives a compound of the invention such as compound 85 or 92, and the other of which receives a placebo. Women in the test group receive between 30–600 mg of the drug per day by the oral route. They continue this therapy for 3–12 months. Accurate records are kept as to the number and severity of the CNS disorders in both groups and at the end of the study these results are compared. Utility of the compounds of the invention is demonstrated by the therapeutic effect they have on patients suffering from CNS disorders as may be evaluated using this procedure.

EXAMPLE 46

Evaluation of the Compounds of the Invention to Inhibit Estrogen-Dependent Skin and Vaginal Atrophy in Postmenopausal Women Inhibition of Skin Atrophy: Three to twenty women, who are postmenopausal and in good health, are selected. The women are also selected on the basis of their presenting several signs of rapid dermal atrophy, such as a rapid increase in the number of facial wrinkles or crow's feet, rapid change in the pigmentation of the skin, i.e. "age spots", or other complaints of rapid dermal aging. As dermal atrophy may be the result of other factors such as UV damage from the sun or other environmental insults, such patients who are suffering from these effects would be excluded.

The first component of the study is qualitative and subjective one, i.e., an evaluation of improvement in the patient's appearance. Such an evaluation requires an initial benchmark for future comparison. Some initial benchmarks might be in the form of a standardized set of questions as to how the patient views her own appearance, photographs of the patient, or a psychological profile of the patient's self-image. The second component is quantitative; these include the measurement of urinary excretion of hydroxyproline, moisture content of the skin, glycosaminoglycans in the skin, and changes in resilience and pliability of the skin. Methods for determining these factors are found in "The Menopause", Ed. R. J. Beard, University Press, Chapter 7 (1977) and "Methods in Skin Research", Ed. Skerrow, D. and Skerrow, C. J. John Wiley & Sons Ltd., Chp. 22, "Analysis of Sebaceous Lipids", p. 587–608 (1985), and further references cited therein. Again, an initial benchmark of these quantitative factors is obtained.

The women, thus selected and initially evaluated, are placed in a clinical protocol of receiving 40–400 mg of an active compound of this invention by oral administration either as a single or split dose. Alternatively, these patients are placed in a protocol for topical administration to areas of the skin most effected by the atrophy. This topical protocol includes the use of a suitable formulation containing 5–50% (by weight) of an active compound of this invention applied to the affected area once or twice a day. Either of these protocols continues two to twelve months. Subsequent evaluations, both quantitative and qualitative, are made at appropriate intervals.

A positive result is an improvement in the overall qualitative index of the patient's appearance and/or an improvement in the quantitative parameters, e.g., an increase in the urinary excretion of hydroxyproline signing an increase in turnover and synthesis of collagen, an increase in moisture content glycosaminoglycans, pliability, or resilience of the skin.

Inhibition of Vaginal Atrophy: Three to twenty women suffering from vaginal atrophy associated with menopause are selected. These women are in general good health. Since the nature of this disorder is highly idiosyncratic and subjective, evaluation of the effectiveness of treatment is necessarily be subjective in nature. These patients are asked to keep a daily log noting such details as vaginal itching and scaling and the degree of comfort in sexual intercourse. These women are placed on a clinical protocol similar to that described above for atrophy of the skin. Particular emphasis is placed on the use of vaginal suppositories containing 5–25% of an active compound of this invention.

A positive result is an improvement in the comfort of sexual intercourse and/or a decrease in vaginal itching or scaling.

EXAMPLE 47

Evaluation of the Compounds of the Invention to Inhibit Estrogen-Dependent Pulmonary Hypertensive Disease Five to fifty women are selected for the clinical study. The women suffer from a pulmonary hypertensive disease. Because of the idiosyncratic and subjective nature of these disorders, the study has a placebo control group, i.e., the women are divided into two groups, one of which receives a compound of the invention such as compound 85 or 92, and the other of which receives a placebo. Women in the test group receive between 30–600 mg of the drug per day by the oral route. They continue this therapy for 3–12 months. Accurate records are kept as to the number and severity of the symptoms in both groups and at the end of the study these results are compared. The results are compared both between members of each group and also the results for each patient are compared to the symptoms reported by each patient before the study began. Utility of the compounds of the invention is illustrated by the positive impact they are expected to have on the patients evaluated using this procedure.

What is claimed is:

1. A 17-desoxy-1,3,5(10)-estratriene containing the molecular moiety $$-(CH_2)_{\overline{m}}-O-L-(CH_2)_{\overline{p}}-N\begin{matrix}R^{29}\\R^{30}\end{matrix}$$

at the C-17 position of the estratriene nucleus, wherein:
  m is an integer in the range of 1 to 6;
  p is an integer in the range of 0 to 6;
  $R^{29}$ and $R^{30}$ are independently hydrogen, lower alkyl, or halogenated lower alkyl, or are linked together to form a heterocycloalkyl ring; and
  L is a five- or six-membered cyclic moiety that may or may not be aromatic, optionally containing 1 to 4 heteroatoms selected from the group consisting of N, O and S and combinations thereof, and optionally substituted with one or more substituents selected from the group consisting of alkyl, alkenyl, alkoxy, halogenated alkyl, alkenyl, and alkoxy, carboxyl, hydroxy, amino, nitro, cyano, and halogen.

2. A 17-desoxy-1,3,5(10)-estratriene containing the molecular moiety $$-(CH_2)_{\overline{m}}-O-\underset{Q^3\ Q^4}{\underset{||}{\overset{Q^1\ Q^2}{\overset{||}{\diagup\diagdown}}}}-(CH_2)_{\overline{p}}-N\begin{matrix}R^{29}\\R^{30}\end{matrix}$$

at the C-17 position of the estratriene nucleus, wherein:
  m is an integer in the range of 1 to 6;
  p is an integer in the range of 0 to 6;
  $R^{29}$ and $R^{30}$ are lower alkyl or are linked together to form a five- or six-membered heterocycloalkyl ring; and
  $Q^1$, $Q^2$, $Q^3$ and $Q^4$ are independently selected from the group consisting of hydrogen, hydroxyl, carboxyl, alkoxy, alkyl, halogen, amino, and alkyl-substituted amino.

3. A compound having the structure of formula (IIIa)

(IIIa)

[Chemical structure diagram showing an estratriene-based polycyclic structure with substituents $R^1$ through $R^{10}$, $R^{23}$, $R^{24}$, $R^{25}$, $R^{29}$, $R^{30}$, and $(CH_2)_{\overline{m}}-O-L-(CH_2)_{\overline{p}}-N$ group]

wherein:
  m is an integer in the range of 1 to 6 inclusive;
  n is 0 or 1;
  p is an integer in the range of 0 to 6 inclusive;
  r2 is an optional double bond, and when r2 is present, $R^1$ is $CR^{11}R^{12}$, wherein $R^{11}$ and $R^{12}$ are hydrogen or lower alkyl, and when r2 is absent, $R^1$ is hydrogen, alkyl or halogen;
  $R^2$ is selected from the group consisting of hydrogen, hydroxyl, alkyl, alkenyl, aryl, alkaryl, —$ONO_2$, —$OR^{13}$ and —$SR^{13}$ wherein $R^{13}$ is alkyl, acyl, or aryl;
  $R^3$ is selected from the group consisting of hydrogen, hydroxyl, alkyl, alkenyl, aryl, alkaryl, cyano, —$OR^{13}$ and —$SR^{13}$ wherein $R^{13}$ is as defined previously;
  $R^4$ is hydrogen or lower alkyl;
  $R^5$ is selected from the group consisting of hydrogen, lower alkoxy, halogen, cyano, —$CH_2CH=CH_2$, —CHO, —$NR^{14}R^{15}$ and —$(CH_2)NR^{14}R^{15}$ wherein $R^{14}$ and $R^{15}$ may be the same or different and are either hydrogen or alkyl, or together form a five- or six-membered cycloalkyl group optionally containing an additional nitrogen heteroatom;
  $R^6$ is selected from the group consisting of hydrogen, alkyl, acyl, —C(O)-aryl, —C(O)-alkyl and —$SO_2NH_2$;
  $R^7$ is selected from the group consisting of hydrogen, halogen, —$NO_2$, —CHO, —$CH_2CH=CH_2$, —$NR^{16}R^{17}$ and —$(CH_2)NR^{16}R^{17}$ wherein $R^{16}$ and $R^{17}$ may be the same or different and are either hydrogen, alkyl or acetyl;

R[8] is selected from the group consisting of hydrogen, hydroxyl, —OR[18] and —SR[18] wherein R[18] is lower alkyl, lower acyl or aryl;

R[10] is methyl or ethyl;

R[23] is hydrogen or lower alkyl; and

R[24] and R[25] are both hydrogen or are both methylene bound to each other through a single covalent bond, R[29] and R[30] are independently hydrogen, lower alkyl or halogenated lower alkyl, or are linked together to form a heterocycloalkyl ring; and L is a five- or six-membered cyclic moiety that may or may not be aromatic, optionally containing 1 to 4 heteroatoms selected from the group consisting of N, O and S and combinations thereof, and optionally substituted with one or more substituents selected from the group consisting of alkyl, alkenyl, alkoxy, halogenated alkyl, alkenyl, and alkoxy, carboxyl, hydroxy, amino, alkyl-substituted amino, nitro, cyano, and halogen.

4. The compound of claim 3, having the structure of formula (IIIb)

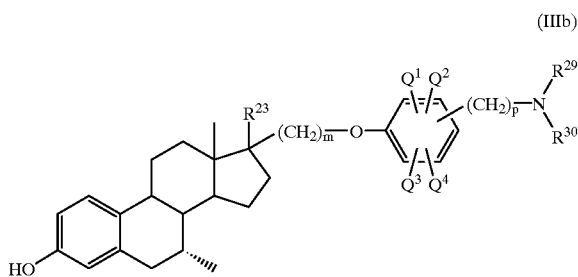

(IIIb)

wherein R[29] and R[30] are lower alkyl or are linked together to form a five- or six-membered heterocyclic ring, and Q[1], Q[2], Q[3], and Q[4] are independently selected from the group consisting of hydrogen, hydroxyl, carboxyl, alkoxy, alkyl, halogen, amino, and alkyl-substituted amino.

5. A pharmaceutical composition for administering an anti-estrogenic agent, comprising a therapeutically effective amount of the compound of any one of claims 1, 2, and 3 in combination with a pharmaceutically acceptable carrier.

6. A chemical compound selected from the group consisting of:

3-hydroxy-7α-methyl-21-[2'-methoxy-4'-(diethylaminomethyl)-phenoxy]-19-norpregna-1,3,5(10)-triene;

3-hydroxy-7α-methyl-21-[3'-methoxy-4'-(piperidinomethyl)-phenoxy]-19-norpregna-1,3,5(10)-triene;

3-hydroxy-7α-methyl-21-[2'-methoxy-4'-(4"-methylpiperazinomethyl)phenoxy]-19-norpregna-1,3,5(10)-triene;

3-hydroxy-7α-methyl-21-[2'-methoxy-4'-(pyrrolidinomethyl)phenoxy]-19-norpregna-1,3,5(10)-triene;

3-hydroxy-7α-methyl-21-[2'-methoxy-4'-(N,N-dimethylaminomethyl)phenoxy]-19-norpregna-1,3,5(10)-triene;

3-hydroxy-7α-methyl-21-[5'-(N,N-diethylaminomethyl)-2'-pyridinoxy]-19-norpregna-1,3,5(10)-triene;

3-hydroxy-7α-methyl-21-[4'-(2"-(N,N-diethylamino)ethoxy)phenoxy]-19-norpregna-1,3,5(10)-triene;

3-hydroxy-7α-methyl-21-[4'-(2"-piperidinoethoxy)phenoxy]-19-norpregna-1,3,5(10)-triene;

3-hydroxy-7α-methyl-21-[4'-(2"-(N,N-dimethylamino)ethoxy)phenoxy]-19-norpregna-1,3,5(10)-triene;

3-hydroxy-7α-methyl-21-[4'-(2"-piperidinomethyl)phenoxy]-19-norpregna-1,3,5(10)-triene;

and pharmaceutically acceptable salts thereof.

7. 3-Hydroxy-7α-methyl-21-[2'-methoxy-4'-(diethylaminomethyl)-phenoxy]-19-norpregna-1,3,5(10)-triene.

8. 3-Hydroxy-7α-methyl-21-[3'-methoxy-4'-(piperidinomethyl)-phenoxy]-19-norpregna-1,3,5(10)-triene.

9. 3-Hydroxy-7α-methyl-21-[2'-methoxy-4'-(4"-methylpiperazinomethyl)-phenoxy]-19-norpregna-1,3,5(10)-triene.

10. 3-Hydroxy-7α-methyl-21-[2'-methoxy-4'-(pyrrolidinomethyl)phenoxy]-19-norpregna-1,3,5(10)-triene.

11. 3-Hydroxy-7α-methyl-21-[2'-methoxy-4'-(N,N-dimethylaminomethyl)-phenoxy]-19-norpregna-1,3,5(10)-triene.

12. A pharmaceutical composition for administering a pharmaceutical agent, comprising a therapeutically effective amount of a compound of claim 6 in combination with a pharmaceutically acceptable carrier.

13. A pharmaceutical composition for administering a pharmaceutical agent, comprising a therapeutically effective amount of a compound of claim 7 in combination with a pharmaceutically acceptable carrier.

14. A pharmaceutical composition for administering a pharmaceutical agent, comprising a therapeutically effective amount of the compound of claim 8 in combination with a pharmaceutically acceptable carrier.

15. A pharmaceutical composition for administering a pharmaceutical agent, comprising a therapeutically effective amount of a compound of claim 9 in combination with a pharmaceutically acceptable carrier.

16. A pharmaceutical composition for administering a pharmaceutical agent, comprising a therapeutically effective amount of the compound of claim 10 in combination with a pharmaceutically acceptable carrier.

* * * * *